US012533362B2

(12) United States Patent
Saunier et al.

(10) Patent No.: US 12,533,362 B2
(45) Date of Patent: Jan. 27, 2026

(54) METHODS FOR TREATING DISEASES ASSOCIATED WITH CILIOPATHIES

(71) Applicants: ALEXION PHARMACEUTICALS, INC., New Haven, CT (US); INSTITUT NATIONAL DE LA SANTE ET DE LA RECHERCHE MEDICALE, Paris (FR)

(72) Inventors: Sophie Saunier, Paris (FR); Luis Briseno-Roa, Paris (FR); Soraya Sin-Monnot, Levallois-perret (FR); Jean-philippe Annereau, Antony (FR); Marion Delous, Lyons (FR); Hugo Garcia, Maisons-Alfort (FR); Guillermo Del Angel, Lexington, MA (US); Flora Legendre, Eaubonne (FR)

(73) Assignees: ALEXION PHARMACEUTICALS, INC., New Haven, CT (US); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 172 days.

(21) Appl. No.: 16/755,767

(22) PCT Filed: Oct. 12, 2018

(86) PCT No.: PCT/US2018/055670
§ 371 (c)(1),
(2) Date: Apr. 13, 2020

(87) PCT Pub. No.: WO2019/075369
PCT Pub. Date: Apr. 18, 2019

(65) Prior Publication Data

US 2021/0186985 A1 Jun. 24, 2021

Related U.S. Application Data

(60) Provisional application No. 62/572,051, filed on Oct. 13, 2017.

(51) Int. Cl.
*A61K 31/352* (2006.01)
*A61K 31/5575* (2006.01)
*A61K 31/559* (2006.01)
*A61K 49/00* (2006.01)
*A61P 13/12* (2006.01)
*A61P 43/00* (2006.01)

(52) U.S. Cl.
CPC ........ *A61K 31/559* (2013.01); *A61K 31/5575* (2013.01); *A61K 49/0008* (2013.01); *A61P 43/00* (2018.01)

(58) Field of Classification Search
CPC ................ A61K 31/352; A61K 31/559; A61K 31/5575; A61P 13/12; A61P 43/00
See application file for complete search history.

(56) References Cited

U.S. PATENT DOCUMENTS

2011/0081296 A1 4/2011 Barr et al.
2017/0016915 A1 1/2017 Katsanis et al.

OTHER PUBLICATIONS

Woodward, D., D. Pepperl, T. Burkey and J. Regan, "6-isopropoxy-9-oxoxanthene-2-carboxylic acid (AH 6809), A Human EP2 Receptor Antagonist", Biochemical Pharmacology (1995), 50(10), pp. 1731-1733. (Year: 1995).*

Abdela-Ali, Fatima, "The role of Prostaglandin E2 in the pathogenesis of Autosomal Dominant Polycystic Kidney Disease" University of Sheffield (2016), pp. i-244. (Year: 2016).*

Liu et al., "Prostaglandin E2 mediates proliferation and chloride secretion in ADPKD cystic renal epithelia", Am. J. Physiol. Renal Physio. (2012), 303 (10), pp. F1425-F1434. (Year: 2012).*

Ganesh, T., "Prostanoid Receptor EP2 as a Therapeutic Target", J Med Chem. (2015), pp. 1-28. (Year: 2015).*

Saunier, S., J. Calado, F. Benessy, F. Silbermann, R. Heilig, J. Weissenbach and C. Antignac, "Characterization of the NPHP1 Locus: Mutational Mechanism Involved in Deletions in Familial Juvenile Nephronophthisis", Am. J. Hum. Genet. (2000), 66: pp. 778-789. (Year: 2000).*

Hildebrandt, F., M. Attanasio and E. Otto, "Nephronophthisis: Disease Mechanisms of a Ciliopathy", J Am Soc Nephrol. (2010), HHMI Author manuscript, pp. 1-25. (Year: 2010).*

Niwa, S., "The nephronophthisis-related gene ift-139 is required for ciliogenesis in Caenorhabditis elegans", Sci Rep 6, 31544 (2016), https://doi.org/10.1038/srep31544, Accessed on Sep. 19, 2024. (Year: 2016).*

Jin, D., T. Ni, J. Sun, et al., "Prostaglandin signalling regulates ciliogenesis by modulating intraflagellar transport", Nat Cell Biol (2014), 16: pp. 841-851, https://doi.org/10.1038/ncb3029, Accessed on Sep. 19, 2024. (Year: 2014).*

(Continued)

*Primary Examiner* — Kamal A Saeed
*Assistant Examiner* — Sagar Patel
(74) *Attorney, Agent, or Firm* — McBee Moore & Vanik IP, LLC

(57) ABSTRACT

Methods of treating a ciliopathy-associated disease are disclosed, including administering to a subject in need thereof an effective amount of a compound that targets at least one G-protein coupled receptor. Methods for identifying therapeutic agents for treating a disease having a ciliopathy are provided, including providing an animal model system of the ciliopathy for testing a putative therapeutic agent; administering a disruptive agent to the animal, treating the administered animal with the putative therapeutic agent, comparing the measurable phenotype of the treated animal with that of the animal without treatment, and identifying the therapeutic target for treating a ciliopathy, when the measurable phenotype of the treated animal is reduced as compared with that of the animal without treatment.

18 Claims, 71 Drawing Sheets

(56) References Cited

OTHER PUBLICATIONS

Vukicevic, S., P. Simic, F. Borovecki, L. Grgurevic, D. Rogic, I. Orlic, WA Grasser, DD Thompson, and VM Paralkar, "Role of EP2 and EP4 receptor-selective agonists of prostaglandin E2 in acute and chronic kidney failure", Kidney International (2006), 70, pp. 1099-1106. (Year: 2006).*

Ganesh, T., "Prostanoid Receptor EP2 as a Therapeutic Target", J Med Chem. Author manuscript (2015), pp. 1-28. (Year: 2015).*

Fliser, D., M. Schroter, M. Neubeck, and E. Ritz, "Coadministration of thiazides increases the efficacy of loop diuretics even in patients with advanced renal failure", Kidney International (1994), 46: pp. 482-488. (Year: 1994).*

PCT International Search Report for PCT/US2018/055670, mailed Jan. 24, 2019.

Liu, et al., "Prostaglandin E2 mediates proliferation and chloride secretion in ADPKD cystic renal epithelia," Am. J. Physiol. Renal Physiol., (2012), vol. 303, No. 10: F1425-F1434.

Sang, et al., "Mapping the NPHP-JBTS-MKS Protein Network Reveals Ciliopathy Disease Genes and Pathways," Cell, (2011), vol. 145, No. 4: 513-528.

Bruechle, Nadia Ortiz, et al. "Uniparental disomy as an unexpected cause of Meckel-Gruber syndrome: report of a case" Pediatric Nephrology, vol. 32, No. 10, pp. 1989-1992, Oct. 2017.

Forsythe, Elizabeth, et al. "Bardet-Biedl syndrome" European Journal of Human Genetics, vol. 21, No. 1, pp. 8-13, Jan. 2013.

Sakai, Naohiko, et al. "Oral-facial-digital syndrome type II (Mohr syndrome): clinical and genetic manifestations" Journal Craniofac. Surgery, vol. 13, No. 2, pp. 321-326, Mar. 2002 (Abstract Only).

Tsang, Stephen H., et al. "Ciliopathy: Senior-Løken Syndrome" Adv. Exp. Med. Biology, vol. 1085, pp. 175-178, 2018 (Astract Only).

Sun, JianJian, et al. "Cilia Function in Cell Signaling and Organ Development" Scientia Sinica Vitae, vol. 46, No. 4, pp. 354-362, 2016 (Translation of Abstract Only—at the end of the document).

Bergmann, Carston. "Genetics of Autosomal Recessive Polycystic Kidney Disease and its Differential Diagnoses" Frontiers in Pediatrics, vol. 5, Article 221, Feb. 2018.

Garcia, Hugo, et al. "Agonists of prostaglandin E2 receptors as potential first in class treatment for nephronophthisis and related ciliopathies" PNAS, vol. 119, No. 18, 2022.

Hildebrandt, Friedhelm, et al. "Ciliopathies" New England Journal of Medicine, vol. 364, No. 16, pp. 1533-1543, Apr. 21, 2011.

Markovic, Tijana, et al. "Structural features of subtype-selective EP receptor modulators" Drug Discovery Today, vol. 22, No. 1, pp. 57-71, Jan. 2017.

Raina, Rupesh, et al. "Clinical utility and tolerability of tolvaptan in the treatment of autosomal dominant polycystic kidney disease (ADPKD)" Drug, Healthcare and Patient Safety, vol. 14, pp. 147-159, 2022.

Reiter, Jeremy F., et al. "Genes and molecular pathways underpinning ciliopathies" National Review of Molecular Cell Biology, vol. 18, No. 9, pp. 533-547, Sep. 2017.

Sun, JianJian, et al. "Cilia Function in Cell Signaling and Organ Development" Scientia Sinica Vitae, vol. 46, No. 4, pp. 354-362, 2016 (Partial English Translation provided at the end of the document).

Vleeshouwers, Ward, et al. "Characterization of the Signaling Modalities of Prostaglandin E2 Receptors EP2 and EP4 Reveals Crosstalk and a Role for Microtubules" Frontiers in Immunology, vol. 11, Article 613286, Feb. 2021.

Young, Robert N., et al. "Discovery and Synthesis of a Potent, Selective and Orally Bioavailable EP4 Receptor Agonist" Heterocycles, vol. 64, No. 1, pp. 437-446, Dec. 2004.

McKusick, Victor A., "Senior-Loken Syndrome 1; SLSN1", Entry—#266900, retrieved from https://www.omim.org/entry/266900 (4 p), last updated Apr. 8, 2024. Downloaded Sep. 4, 2024.

Malglaive, France de, et al., "Pharmacological cAMP stimulation via prostaglandin receptors rescues ciliary defects in CEP290-deficient human and mouse models", bioRxiv, Oct. 6, 2023. doi: https://doi.org/10.1101/2023.10.06.561156.

* cited by examiner

| Mann Whitney test | |
|---|---|
| P value | <0.0001 |
| Exact or approximate P value? | Exact |
| P value summary | **** |

*Mann-Whitney test

| Mann Whitney test | |
|---|---|
| P value | 0.3823 |
| Exact or approximate P value? | Exact |
| P value summary | ns |

| Mann Whitney test | |
|---|---|
| P value | <0.0001 |
| Exact or approximate P value? | Exact |
| P value summary | **** |

| Mann Whitney test | |
|---|---|
| P value | <0.0001 |
| Exact or approximate P value? | Exact |
| P value summary | **** |

$\Delta Ct = C_T$ gene of interest - $C_T$ internal control (HPRT1)

| | Agonists | Antagonists |
|---|---|---|
| | | |
| COX1 | - | SC-560 |
| COX2 | - | Celecoxib |
| COX1& 2 | - | Keterolac |
| | | |
| EP1 | Iloprost | GW 848687X |
| EP2 | CP-544326 | PF-04418948 |
| EP3 | Sulprostone | L-798,106 |
| EP4 | L-902, 688 | BGC 20-1531 |
| EP1-4 | Dinoprostone | - |
| | 16,16-dimethyl-PGE2 | |

FIG. 15

| Sample ID | Replicate | Extraction | Condition | Sample ID | Replicate | Extraction | Condition |
|---|---|---|---|---|---|---|---|
| 072 | 1 | RLT | 10 µM | 114 | 1 | QIAZOL | 10 µM |
| 073 | 1 | RLT | 2 µM | 115 | 1 | QIAZOL | 2 µM |
| 074 | 1 | RLT | 0.2 µM | 116 | 1 | QIAZOL | 0.2 µM |
| 076 | 1 | RLT | DMSO 0.04% | 118 | 1 | QIAZOL | DMSO 0.04% |
| 077 | 1 | RLT | Media | 119 | 1 | QIAZOL | Media |
| 191 | 2 | RLT | 10 µM | 233 | 2 | QIAZOL | 10 µM |
| 192 | 2 | RLT | 2 µM | 234 | 2 | QIAZOL | 2 µM |
| 193 | 2 | RLT | 0.2 µM | 235 | 2 | QIAZOL | 0.2 µM |
| 195 | 2 | RLT | DMSO 0.04% | 237 | 2 | QIAZOL | DMSO 0.04% |
| 196 | 2 | RLT | Media | 238 | 2 | QIAZOL | Media |
| 310 | 3 | RLT | 10 µM | 352 | 3 | QIAZOL | 10 µM |
| 311 | 3 | RLT | 2 µM | 353 | 3 | QIAZOL | 2 µM |
| 312 | 3 | RLT | 0.2 µM | 354 | 3 | QIAZOL | 0.2 µM |
| 314 | 3 | RLT | DMSO 0.04% | 356 | 3 | QIAZOL | DMSO 0.04% |
| 315 | 3 | RLT | Media | 357 | 3 | QIAZOL | Media |
| 450 | 4 | RLT | 10 µM | 492 | 4 | QIAZOL | 10 µM |
| 451 | 4 | RLT | 2 µM | 493 | 4 | QIAZOL | 2 µM |
| 452 | 4 | RLT | 0.2 µM | 494 | 4 | QIAZOL | 0.2 µM |
| 454 | 4 | RLT | DMSO 0.04% | 496 | 4 | QIAZOL | DMSO 0.04% |
| 455 | 4 | RLT | Media | 497 | 4 | QIAZOL | Media |
| 576 | 5 | RLT | 10 µM | 618 | 5 | QIAZOL | 10 µM |
| 577 | 5 | RLT | 2 µM | 619 | 5 | QIAZOL | 2 µM |
| 578 | 5 | RLT | 0.2 µM | 620 | 5 | QIAZOL | 0.2 µM |
| 580 | 5 | RLT | DMSO 0.04% | 622 | 5 | QIAZOL | DMSO 0.04% |
| 581 | 5 | RLT | Media | 623 | 5 | QIAZOL | Media |

FIG. 18

RLT EXTRACTION

| | 10 µM vs. DMSO | | 2 µM vs. DMSO | | 0.2 µM vs. DMSO | |
|---|---|---|---|---|---|---|
| # Analyzed genes | 75,641 | | 75,641 | | 75,641 | |
| # Expressed genes | 27,282 | | 27,428 | | 27,645 | |
| # Regulated genes | 460 | | 546 | | 462 | |
| | 244 up | 216 down | 183 up | 363 down | 185 up | 277 down |
| Most regulated genes | 1. PCSK1<br>2. PDK4<br>3. RBP4 | 1. TAGLN<br>2. JD058756<br>3. ANKRD1 | 1. PCSK1<br>2. PDK4<br>3. RBP4 | 1. TAGLN<br>2. ANKRD1<br>3. GREM2 | 1. PCSK1<br>2. PDK4<br>3. RBP4 | 1. TAGLN<br>2. KRT19P2<br>3. ANKRD1 |
| Most significant pathway(s) | Cell adhesion and extracellular matrix (down) | | Cell adhesion and extracellular matrix (down) | | Cell adhesion and extracellular matrix (down) | |

FIG. 22

QIAZOL EXTRACTION

| | 10 μM vs. DMSO | | 2 μM vs. DMSO | | 0.2 μM vs. DMSO | |
|---|---|---|---|---|---|---|
| **# Analyzed genes** | 75,641 | | 75,641 | | 75,641 | |
| **# Expressed genes** | 27,647 | | 28,155 | | 28,047 | |
| **# Regulated genes** | 615 | | 638 | | 550 | |
| | 302 up | 313 down | 397 up | 241 down | 355 up | 195 down |
| **Most regulated genes** | 1. RBP4<br>2. IGFBP3<br>3. PCSK1 | 1. TAGLN<br>2. U88892<br>3. ANKRD1 | 1. RBP4<br>2. IGFBP3<br>3. PCSK1 | 1. TAGLN<br>2. ANKRD1<br>3. GREM1 | 1. RBP4<br>2. PDK4<br>3. IGFBP3 | 1. TAGLN<br>2. ANKRD1<br>3. U88892 |
| **Most significant pathway(s)** | Cell adhesion and extracellular matrix (down)<br>Response to virus infection /interferon signaling (up) | | Cell adhesion and extracellular matrix (down)<br>Response to virus infection /interferon signaling (up) | | Cell adhesion and extracellular matrix (down)<br>Response to virus infection /interferon signaling (up) | |

FIG. 23

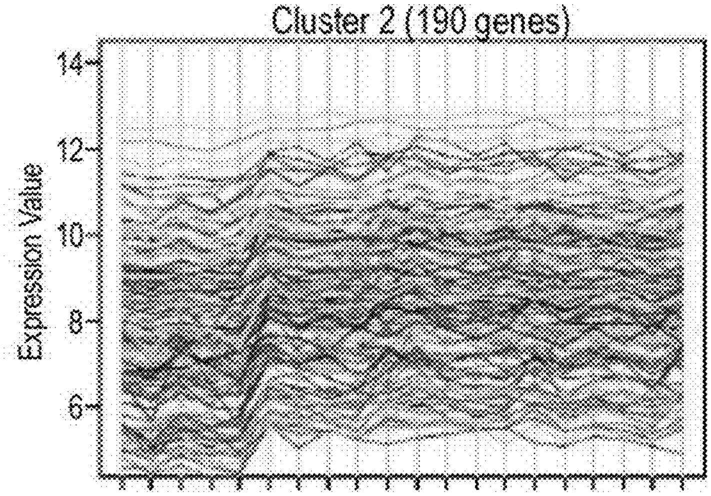
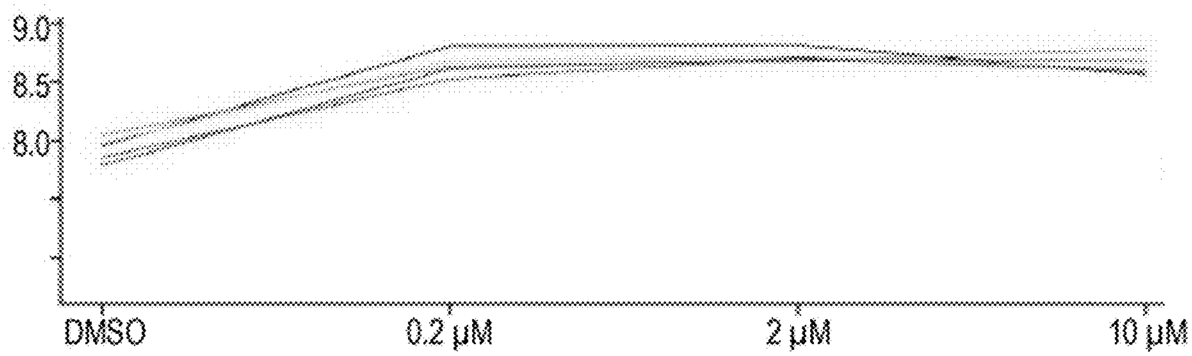
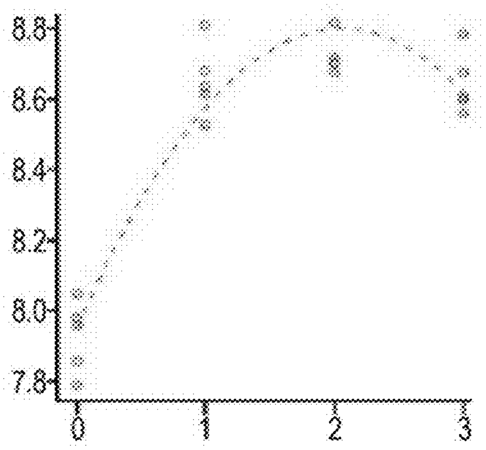
FIG. 24B

| Category | Number |
|---|---|
| Total WY p<0.05 | 31 |
| Drugged | 9 |
| Druggable | 1 |
| Biopharm | 4 |

- IMPDH1
- CCL2
- MICA
- TYMS
- C1R
- CXCL10
- PLAT
- FGF1
- IL1R1

FIG. 27

IPA Network constructed with mRNA (316), Protein (29), miRNA (7), metabolites (11)

Target opportunities

| gene | category | no. drugs |
|---|---|---|
| ADRB2 | DRUGGED | 87 |
| KCNMA1 | DRUGGED | 17 |
| KCNN4 | DRUGGED | 11 |
| KCNK2 | DRUGGED | 9 |
| ABCC4 | DRUGGED | 3 |
| CXCL10 | DRUGGED | 1 |
| SPP1 | DRUGGED | 1 |
| ADCY8 | DRUGGABLE | |
| AMPD3 | DRUGGABLE | |
| CAPN2 | DRUGGABLE | |
| GPRC5B | DRUGGABLE | |
| TGM2 | DRUGGABLE | |
| ANXA2 | BIOPHARM | |
| CD9 | BIOPHARM | |

IPA Network constructed with mRNA (316), Protein (29), miRNA (7), metabolites (11)

Target opportunities

| gene | category | no. drugs |
|---|---|---|
| KCNMA1 | DRUGGED | 17 |
| TUBA4A | DRUGGED | 4 |
| PLAT | DRUGGED | 3 |
| TUBA1B | DRUGGED | 3 |
| PCK1 | DRUGGED | 2 |
| ACTR3 | DRUGGED | 1 |
| ARPC2 | DRUGGED | 1 |
| BCL2L1 | DRUGGED | 1 |
| ANXA2 | BIOPHARM | |
| ANXA4 | BIOPHARM | |
| CTGF | BIOPHARM | |
| CD109 | DRUGGABLE | |
| CIT | DRUGGABLE | |
| KSR1 | DRUGGABLE | |
| PRSS23 | DRUGGABLE | |
| TNC | DRUGGABLE | |
| CAPN2 | DRUGGABLE | |

IPA Network constructed with mRNA (316), Protein (29), miRNA (7), metabolites (11)

Target opportunities

| gene | category | no. drugs |
|---|---|---|
| TYMS | DRUGGED | 19 |
| KCNMA1 | DRUGGED | 17 |
| IMPDH1 | DRUGGED | 4 |
| TUBA4A | DRUGGED | 4 |
| TUBA1B | DRUGGED | 3 |
| CXCL10 | DRUGGED | 1 |
| HAL | DRUGGED | 1 |
| ANXA2 | BIOPHARM | |
| CTGF | BIOPHARM | |
| ITGA11 | DRUGGABLE | |
| OSR1 | DRUGGABLE | |

A
| Drug/Concentration | Lethality 24 hpf) | Lethality 48 hpf (n/total) | Lethality 5 dpf (n/total) | Curly 48 hpf | Cyst(s) 48 hpf |
|---|---|---|---|---|---|
| DMSO $10^{-6}$ | 0/10 | 0/10 | 0/10 | 0 | 0 |
| DMSO $5.10^{-6}$ | 0/11 | 0/11 | 0/11 | 0 | 0 |
| DMSO $10^{-5}$ | 0/12 | 0/12 | 0/12 | 0 | 0 |
| DMSO $10^{-4}$ | 0/10 | 0/10 | 0/10 | 0 | 0 |
| DMSO 1% | 0/10 | 0/10 | 0/10 | 0 | 0 |
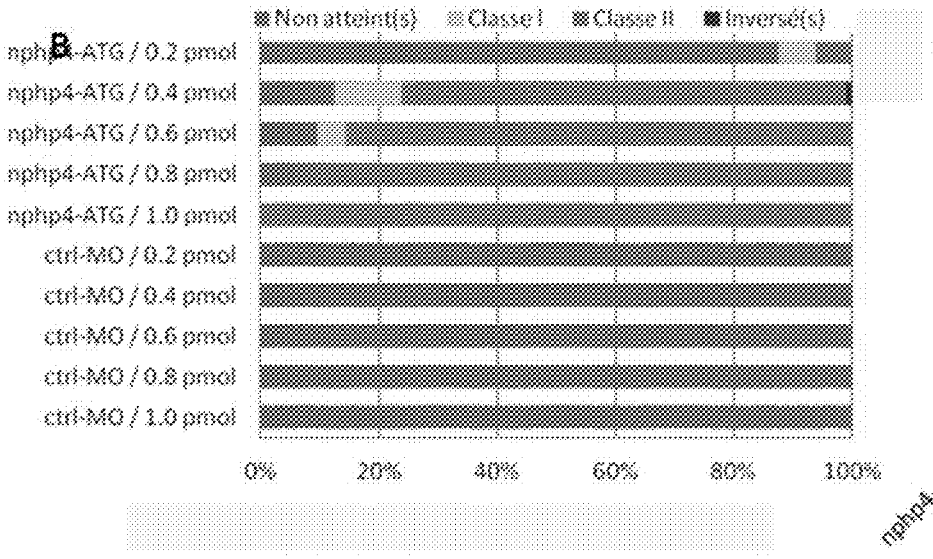
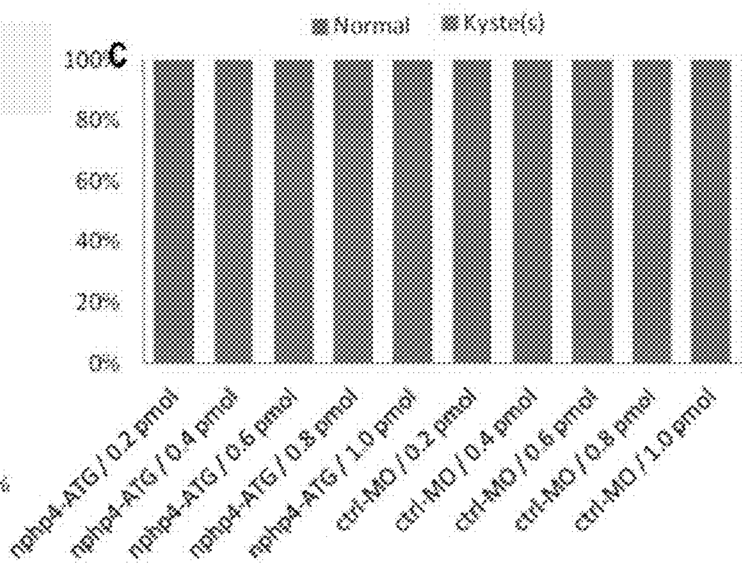
FIG. 31

C (N=5 n=237), p= ,009371 Fischer exact test

| Group n° | Treatment | Dose regimen | Number of animals / time-points after intraperitoneal injection | | | | | | | |
|---|---|---|---|---|---|---|---|---|---|---|
| | | | 0.5h ± 3 min (a) | 1h ± 6 min (c) | 2h ± 12 min (b) | 4h ± 24 min (a) | 8h ± 50 min (b) | 24h ± 2h (c) | 72h ± 7 h (a) | 168h ± 16h (b) |
| 1 | Taprenepag isopropyl | **1** mg/kg on Day 0 | 1, 2, 3, 4 | 5, 6, 7, 8 | 9, 10, 11, 12 | 13, 14, 15, 16 | 17, 18, 19, 20 | 21, 22, 23, 24 | 25, 26, 27, 28 | 29, 30, 31, 32 |
| 2 | Taprenepag isopropyl | **8** mg/kg on Day 0 | 33, 34, 35, 36 | 37, 38, 39, 40 | 41, 42, 43, 44 | 45, 46, 47, 48 | 49, 50, 51,52 | 53, 54, 55, 56 | 57, 58, 59, 60 | 61, 62, 63, 64 |
| 3 | Taprenepag | **8** mg/kg on Day 0 | 65, 66, 67, 68 | 69, 70, 71, 72 | 73, 74, 75, 76 | 77, 78, 79, 80 | 81, 82, 83, 84 | 85, 86, 87,88 | 89, 90, 91, 92 | 93, 94, 95, 96 |

(a) = set 1 / (b) = set 2 / (c) = set 3

FIG. 36

| | wt solutol 2 | nphp1 KO solutol 2/3-4 days | nphp1 KO F00718 mg/kg/3-4 days |
|---|---|---|---|
| Number of values | 5 | 8 | 9 |
| | | | |
| Minimum | 3.223 | 1.045 | 1.381 |
| 25% Percentile | 3.406 | 1.272 | 1.568 |
| Median | 3.603 | 1.467 | 1.639 |
| 75% Percentile | 3.666 | 1.555 | 2.004 |
| Maximum | 3.684 | 2.568 | 3.096 |
| | | | |
| 10% Percentile | 3.223 | 1.045 | 1.381 |
| 90% Percentile | 3.684 | 2.568 | 3.096 |
| | | | |
| Mean | 3.549 | 1.53 | 1.844 |
| Std. Deviation | 0.1862 | 0.4525 | 0.5228 |
| Std. Error of Mean | 0.08327 | 0.16 | 0.1743 |
| | | | |
| Lower 95% CI of mean | 3.318 | 1.152 | 1.442 |
| Upper 95% CI of mean | 3.78 | 1.908 | 2.246 |
| | | | |
| Sum | 17.75 | 12.24 | 16.6 |
| | | | |
| Shapiro-Wilk normality test | | | |
| W | 0.7417 | 0.7736 | 0.743 |
| P value | 0.0249 | 0.0148 | 0.0045 |
| Passed normality test (alpha=0.05)? | No | No | No |
| P value summary | * | * | ** |

METHODS FOR TREATING DISEASES ASSOCIATED WITH CILIOPATHIES

CROSS REFERENCE TO RELATED APPLICATIONS

This application is the National Stage entry of International Application No. PCT/US2018/055670, filed 12 Oct. 2018, which claims priority to United States No. 62/572,051, filed 13 Oct. 2017.

BACKGROUND

A cilium is a microtubule-based cell surface projection that emanate from basal bodies, membrane-docked centrioles. Primary cilia are non-motile sensory organelles present in a single copy on the surface of most growth-arrested or differentiated mammalian cells. Cilia sense flow changes and mediates signalling pathways essential during development and tissue homeostasis, such as Hedgehog, Wnt/PCP and cAMP/PKA signaling. Intraflagellar transport (IFT) selects cargoes at the base of the cilium and transports axonemal components required for cilia assembly, and proteins involved in ciliary signalling. Once the cilium is formed, control of ciliary membrane composition relies on discrete molecular machines, including a barrier to membrane proteins entering the cilium at a specialized region of the base of the cilium called the transition zone and a trafficking adaptor that controls G protein-coupled receptor (GPCR) localization to the cilium called the BBSome (a complex of Bardet-Biedl syndrome (BBS) proteins and other proteins that is a component of the basal body and is involved in trafficking cargos to the primary cilium). Ciliogenesis requires the coordination of many processes. An intricate concert of cell cycle regulation, vesicular trafficking, and ciliary extension must occur with accurate timing to produce a cilium. The importance of producing and maintaining properly differentiated cilia during embryonic development and in adult physiology is best underscored by the large number of human diseases associated with ciliopathies.

Ciliopathies are a group of human disorders that are directly caused by defects in cilia formation or function. Defective primary cilia cause pleiotropic and highly variable abnormalities, consistent with the extensive tissue distribution of primary cilia and their wide ranging functions. Individuals suffering from primary ciliopathies exhibit combinations of kidney and retinal anomalies, central nervous system defects that can lead to mental retardation, liver defects (including cysts), obesity, as well as a variety of skeletal defects, including abnormalities in limb length, digit number (polydactyly), left/right axis organization (*Situs inversus*) and craniofacial patterning. Abnormalities specific to the photoreceptor connecting cilium can also lead to retinal degeneration and blindness. Examples of primary ciliopathies include nephronophthisis (NPHP), Senior Loken syndrome (SLS), Joubert syndrome (JBTS), Bardet Biedl syndrome (BBS), Meckel Gruber syndrome (MKS), orofacialdigital syndrome (OFD) and Jeune syndrome (JATD).

Nephronophthisis (NPHP) is an autosomal recessive nephropathy characterized by massive interstitial fibrosis, tubular basement membrane thickening and cyst formation, leading to end-stage renal disease (ESRD) during childhood. NPHP can be either isolated or associated with different extra-renal manifestations (e.g., retinal dystrophy, liver fibrosis, skeleton dysplasia, etc.) in syndromic forms referred to hereafter as nephronophthisis-related ciliopathies (NPHP-RCs).

NPHP is driven by 21 NPHP genes, known so far accounting for 60% of the cases. It remains clear that given the high genetic heterogeneity of NPHP and the numerous mechanistic pathways discussed that there is not one unifying pathology leading toward NPHP. The renal histology of NPHP points to a common endpoint of tubular damage and fibrosis, which may have multiple triggers. With each new gene discovery paper, there seems to be better clarity toward molecular diagnosis but more confusion regarding the signaling pathways underlying disease.

There remains a great need for characterization of the poorly-understood molecular basis of diseases having ciliopathies including NPHP and for improved diagnostics and treatments for these diseases.

SUMMARY

In one embodiment, the disclosure is directed to a method of treating at least one ciliopathy-associated disease in a subject, comprising administering to the subject a therapeutically effective amount of at least one agent that targets at least one G-protein coupled receptor (GPCR). In an embodiment, the ciliopathy associated disease results from a homozygous deletion of the NPHP1 locus. In an embodiment, the ciliopathy associated disease results from a heterozygous deletion of the NPHP1 locus and a heterozygous or homozygous loss of function (LOF) at a second locus. In an embodiment, the ciliopathy-associated disease results from a heterozygous deletion in one allele of NPHP1 and a LOF mutation in the second allele. In an embodiment, the ciliopathy-associated disease results from a loss of function mutation in one allele of NPHP1 and different loss of function mutation in the second allele.

In a particular embodiment, the at least one agent is an agonist of the at least one GPCR. In a particular embodiment, the at least one agent is a prostaglandin. In a particular embodiment, the at least one agent is selected from the group consisting of: prostaglandin E1 (PGE1), prostaglandin E2 (PGE2), 16,16-dimethyl-PGE2 (dmPGE2), L902,688, CP-544326 (taprenepag), AGN-210669 (simenepag isopropyl), AGN-210961 (aganepag isopropyl), DE-117 (omidenepag isopropyl), CP-533536 (evatanepag), and combinations thereof. In a particular embodiment, the at least one GPCR is selected from the group consisting of: EP1, EP2, EP3 and EP4. In a particular embodiment, the at least one disease is selected from the group consisting of: nephronophthisis (NPHP), Senior-Loken syndrome (SLS), Joubert syndrome (JBTS) and related disorders disease (JSRD), which may include all the variant forms of JBTS having additional features such as polydactyly, coloboma, retinal dystrophy, renal cysts, oral frenulae, and hepatic fibrosis, Bardet-Biedl syndrome (BBS), Meckel-Gruber syndrome (MKS), orofacialdigital syndrome (OFD), end-stage renal disease driven by NPHP1 large homozygous deletion, and renal and retinal ciliopathies associated to NPHP1, NPHP4, NPHP6/CEP290 mutations, and any ciliopathies driven by an NPHP gene. In a particular embodiment, the at least one agent is CP-544326 (taprenepag) and the at least one GPCR is EP2. In a particular embodiment, the effective amount is between 100 pM and 5 μM. In a particular embodiment, the at least one disease is nephronophthisis.

In one embodiment, the disclosure is directed to a method for identifying a therapeutic agent for treating at least one ciliopathy-associated disease, the method comprising: (a)

administering a test agent to an animal or cellular model of the ciliopathy-associated disease, wherein the animal or cellular model exhibits a measurable phenotype of the ciliopathy-associated disease, (b) comparing the measurable phenotype of the treated animal or cellular model with that of the measurable phenotype of an untreated animal or cellular model, and (c) identifying the test agent as a therapeutic agent for treating a ciliopathy-associated disease when the measurable phenotype of the treated animal or cellular model is ameliorated compared to that of the untreated animal or cellular model. In a particular embodiment, the animal model may be *Danio rerio* (a zebrafish) or nphp1 knockout (KO) mouse model (nphp1−/−). In a particular embodiment, the animal model is generated by administering one or more disruptive agents. In a particular embodiment, the one or more disruptive agents includes a morpholino. In a particular embodiment, the morpholino inhibits the expression of at least one nephrocystin (NPHP), e.g., NPHP4. In a particular embodiment, the measurable phenotype is selected from the group consisting of: body curvature, pronephric cysts, laterality heart defects and dilations of cloaca. In a particular embodiment, the at least one disease is selected from the group consisting of: nephronophthisis (NPHP), Senior-Loken syndrome (SLS), Joubert syndrome (JBTS) and related disorders disease (JSRD), Bardet-Biedl syndrome (BBS), Meckel-Gruber syndrome (MKS) orofacialdigital syndrome (OFD), end-stage renal disease driven by NPHP1 large homozygous deletion, and renal and retinal ciliopathies associated to NPHP1, NPHP4, NPHP6/CEP290 mutations.

In one embodiment, the disclosure is directed to a GPCR agonist for use in the treatment of at least one ciliopathy-associated disease. In a particular embodiment, the GPCR agonist is selected from the group consisting of: prostaglandin E1 (PGE1), prostaglandin E2 (PGE2), 16,16-dimethyl-PGE2 (dmPGE2), CP-544326 (taprenepag), L902,688, AGN-210669 (simenepag isopropyl), AGN-210961 (aganepag isopropyl), DE-117 (omidenepag isopropyl), CP-533536 (evatanepag), and combinations thereof. In a particular embodiment, the GPCR is selected from the group consisting of: EP1, EP2, EP3 and EP4. In a particular embodiment, the at least one disease is selected from the group consisting of nephronophthisis (NPHP), Senior-Loken syndrome (SLS), Joubert syndrome (JBTS) and related disorders disease (JSRD), Bardet-Biedl syndrome (BBS), Meckel-Gruber syndrome (MKS), orofacialdigital syndrome (OFD), end-stage renal disease driven by NPHP1 large homozygous deletion, and renal and retinal ciliopathies associated to NPHP1, NPHP4, NPHP6/CEP290 mutations.

In a particular embodiment, the animal model is generated by administering one or more disruptive agents. In a particular embodiment, the one or more disruptive agents includes CRISPR/Cas9 system that mediates sgRNA-directed genetic deletion. In a particular embodiment, the CRISPR/Cas9 system inhibits the expression at least one nephrocystin (NPHP), e.g., NPHP1. In a particular embodiment, the measurable phenotype is selected from the group consisting of: retina photoreceptors layers thicknesses, electroretinograms and rhodopsin accumulation in the photoreceptors cell body. In a particular embodiment, the at least one disease is selected from the group consisting of: nephronophthisis (NPHP), Senior-Loken syndrome (SLS), Joubert syndrome (JBTS) and related disorders disease (JSRD), Bardet-Biedl syndrome (BBS), Meckel-Gruber syndrome (MKS) orofacialdigital syndrome (OFD), end-stage renal disease driven by NPHP1 large homozygous deletion, and renal and retinal ciliopathies associated to NPHP1, NPHP4, NPHP6/CEP290 mutations.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

FIG. 15 shows prostaglandin (PG) modulators (agonists and antagonists) tested for their effect on ciliogenesis.

FIG. 18 shows RNAs extracted by RLT or Qiazol method for microarray analysis.

FIG. 22 summarizes microarray data obtained from RLT extraction samples.

FIG. 23 summarizes microarray data obtained from Qiazol extraction samples.

FIGS. 24A and 24B show no significant difference between microarray data obtained from various doses.

FIG. 27 shows mRNA differential expression of drugged and druggable genes.

FIG. 31 summarizes (A-C) the effect of morpholino injection on zebrafish.

FIG. 36 shows pharmacokinetics study design.

DETAILED DESCRIPTION OF A PREFERRED EMBODIMENT

Figure 1A:
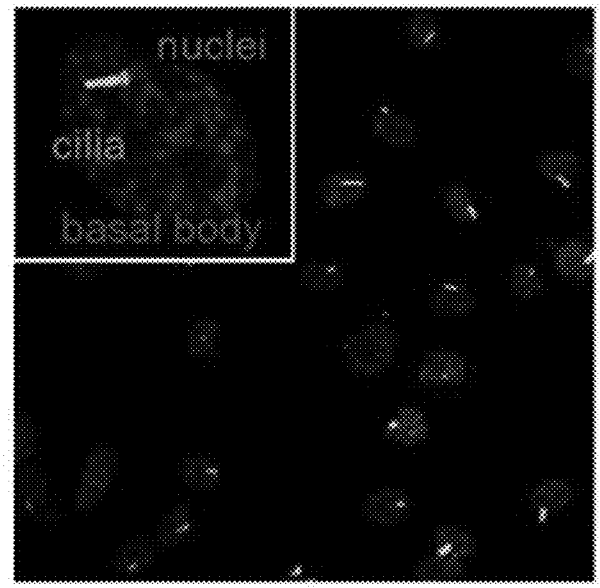
FIGS. 1A-1D show urine derived renal epithelial cells; 1A: normal control; 1B: NPHP patient harbouring an NPHP1 deletion (Pt1); 1C: RT-PCR comparison; 1D: immunoblot comparison.

It is to be understood that the disclosure is not limited to the particular embodiments described below, as variations of the particular embodiments may be made and still fall within the scope of the appended claims. It is also to be understood that the terminology employed is for the purpose of describing particular embodiments, and is not intended to be limiting.

In this specification and the appended claims, "a," "an" and "the" include plural reference unless the context clearly dictates otherwise. Unless defined otherwise, all technical and scientific terms used herein have the same meaning as commonly understood to one of ordinary skill in the art to which this disclosure belongs.

NPHP Patients

Nephronophthisis (NPHP) is a recessive tubulointerstitial ciliopathy that is characterised by a progressive destruction of the kidneys, leading to end stage renal disease (ESRD). The onset of NPHP-driven ESRD ranges from the first months of life (infantile NPHP) up to >60 years of age (adult NPHP), with >17% with ESRD after 20 years of age. Disease-causing mutations have been identified in more than 20 NPHP-associated genes (e.g., NPHP1-20, IFT140, TRAF3IP1/IFT54), accounting for about 60% of all cases presenting with NPHP. Full locus deletion of NPHP1 (NPHP1(del)) accounts for more than 20% of NPHP cases. Traditionally, the rare disease portal Orphanet reports an approximately world-wide frequency of 1 in 100,000 (Canada 1/50,000, USA 1/900,000, Finland 1/100,000; France 1/50,000). There is currently no treatment for NPHP.

Ciliopathies are often caused by mutations in genes encoding transition zone (TZ) proteins or intraflagellar transport (IFT) components (Reiter, J. & Leroux, M., *Nat. Rev. Mol. Cell Biol.,* 18:533-47, 2017; Hildebrandt, F. et al., *N. Engl. J. Med.,* 364:1533-43, 2011; Czarnecki, P. & Shah, J., *Trends Cell Biol.,* 22:201-10, 2012). Functionally, the TZ represents a compartment at the base of primary cilia at the proximal end of the axoneme controlling ciliary protein entry and exit (Betleja, E. & Cole, D., *Curr. Biol.,* 20:R928-31, 2010; Craige, B. et al., *J. Cell Biol.,* 190:927-40, 2010; Omran, H., *J. Cell Biol.,* 190:715-7, 2010; Benzing, T. & Schermer, B., *Nat. Genet.,* 43:723-4, 2011). Molecularly, the TZ consists of different multiprotein complexes, the NPHP1-4-8 module, the NPHP5-6 (Cep290) module, the MKS/B9 module and the Inversin (INVS; NPHP2) compartment (Sang, L. et al., *Cell,* 145:513-28, 2011). The NPHP1-4-8 module, the NPHP5-Cep290 module and the Inversin compartment are sometimes collectively referred to as the NPHP module.

Mutations and/or inactivation of one or more of the genes encoding NPHP module proteins may adversely affect ciliogenesis and/or epithelization, resulting in fibrosis and cysts development in NPHP patients. The IFT machinery selects cargoes at the base of the cilium and transports axonemal components required for cilia assembly, and proteins involved in ciliary signaling. The IFT-B complex, which consists of 16 different proteins, mediates anterograde transport by associating with kinesin II. Retrograde transport is mediated by dynein 2 and the six subunits of the IFT-A complex. Mutations in the six genes encoding the IFT-A subunits have been identified in NPHP-related ciliopathies, only three IFT-B subunits are associated with nephronophthisis (IFT172, IFT54) (Halbritter, J. et al., *Am. J. Hum. Genet.,* 93:915-25, 2013; Bizet, A. et al., *Nat. Commun.,* 6:8666, 2015). In addition to IFT and TZ, appendage proteins, and GPCRs are also essential factors for the ciliary function and maintenance.

Regarding the NPHP module, an Nphp4 mutant mouse developed retinal degeneration but not kidney cysts nor severe ciliogenesis defects; males were infertile and presented sperm with reduced motility (Won, J. et al., *Hum. Mol. Genet.,* 20:482-96, 2011). Similarly, targeted disruption of Nphp1 in the mouse (deletion of the last C-terminal exon 20) did not produce nephronophthisis, but exhibited rapid retinal degeneration starting at P14-P21 (Jiang, S. et al., *Hum. Mol. Genet.,* 17:3368-79, 2008) and caused male infertility (Jiang, S. et al., *Hum. Mol. Genet.,* 18:1566-77, 2009). Cep290 knock out mice lack connecting cilia in photoreceptors and fail to mature motile ependymal cilia, which is consistent with their retinal degeneration and hydrocepahalus phenotypes (Rachel, R. et al., *Hum. Mol. Genet.,* 24:3775-91, 2015).

Mutations in NPHP1 are the most common cause of NPHP. In a large cohort of patients with adult-onset ESRD (unselected for etiology), NPHP due to NPHP1 homozygous full gene deletions (NPHP(del)) has a prevalence of one in 200 patients (0.5%) in all adult-onset ESRD (Snoek, R. et al., *J. Am. Soc. Nephrol.,* 29:772-9, 2018). Although the incidence was clearly higher in patients with an ESRD onset between 18 and 50 years old (prevalence of 0.9%), NPHP can have an onset at up to 61 years of age. Because the method that they used underestimates the total number of causal mutations, they conclude that NPHP is a relatively frequent monogenic cause of adult-onset ESRD that is likely underdiagnosed in current daily practice.

In a cohort of renal transplantation recipients and (corresponding donor) controls from the International Genetics and Translational Research in Transplantation Network (iGenTRAiN) Consortium, an approximate relative frequency of 0.5% (26 out of 5606) patients homozygous for NPHP1 deletion were identified amongst ESRD (18 to 50 years old) adults. From these, only 13% (3 out of 26) were correctly diagnosed as NPHP, and approximatively half (11 of 26%) were diagnosed as CKD patients with unknown aetiology. These results showed that up to 1 in 200 (0.5%) of ESRD adults are NPHP1del genotype; that figure increases to 0.9% when the ESRD onset lies within 18- and 50-years of age (Abstract. ASN2017 & Nephr Dial Trans, Vol 32, 2017).

Described herein are findings generated using Genomics England's Research Environment—a secure workspace for approved researchers to carry out research on the 100,000 Genomes Project dataset, with the goal of identifying novel diseases and patient-related insights, thereby enabling scientific discovery and accelerating its translation into patient care. The 100,000 Genomes project dataset includes rare disease patients (and their relatives) along with cancer patients. Within this dataset, patients homozygous for NPHP1(del) were identified at an approximate relative frequency of 1 in 6,000 (10 out of 61,554)—none of which had been previously diagnosed with NPHP. Of the 10 identified patients, 7 have unequivocal NPHP clinical signs/symptoms, such as renal or ciliopathy signs/symptoms or were recruited as congenital anomalies of the kidney and urinary tract (CAKUT) patients. The remaining 3 patients have a more complex clinical picture-possibly bearing multiple rare diseases. In addition to the homozygotes, 193 NPHP1(del) heterozygous patients were identified in the full dataset (a proximate frequency of 1 in 200 within this dataset); these patients may be heterozygous carriers but may also include NPHP1 compound heterozygotes (NPHP1(del) with NPHP1 Loss-of-Function (LOF) mutation) and/or epistasis (NPHP1 (del) combined with LOF mutations at another locus). Moreover, patients may have additional NPHP1-LOF variants like splice-variants, frameshifts and nonsense mutations, which may also contribute to a clinical NPHP presentation.

NPHP(del) findings described herein resulted from research conducted using the Genomics England database. This research was made possible through access to the data and findings generated by Genomics England's Research Environment and by the patients who consented to the use of their data for research purposes and the NHS clinicians and healthcare teams that contributed to the data and results covered by this research. Genomics England's Research Environment is managed by Genomics England Limited (a wholly owned company of the Department of Health) and is funded by the National Institute for Health Research and NHS England, The Wellcome Trust, Cancer Research UK and the Medical Research Council.

Millions of individuals around the world suffer from ESRD and congenital conditions, for which the only treatment is the transplantation. In the US alone, over 600,000 transplants were performed over the last five decades, and the demand today is higher than ever. Unfortunately, the availability of donor organs has not been able to keep pace with transplant demand. Embodiments of the present disclosure include identifying and/or treating patients who are either homozygous or heterozygous for NPHPs (e.g., NPHP-driven ESRD) and/or NPHP-associated ciliopathies (e.g., NPHP1).

NPHP Patient-Derived Cells

Described herein are materials and methods for identifying therapeutic agents useful for treating a ciliopathy-related disease or disorder, e.g., NPHP, or NPHP1(del)-associated diseases or disorders. Such methods can include the use of cell lines derived from patients. Such cell lines, as developed, can also be used for other related methods, including, for example, monitoring the efficacy of a given treatment for a cliopathy-related disease or disorder or NPHP1(del)-associated diseases or disorders.

Figure 1B:
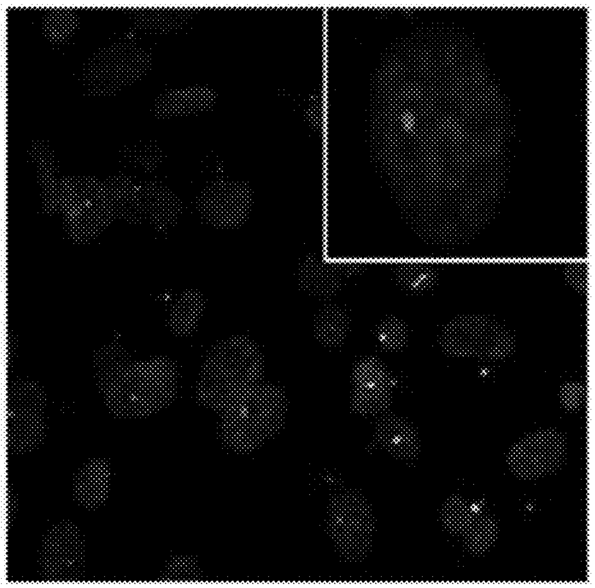
Figure 1C:
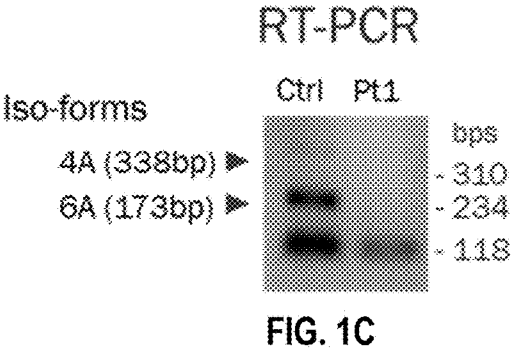
Figure 1D:
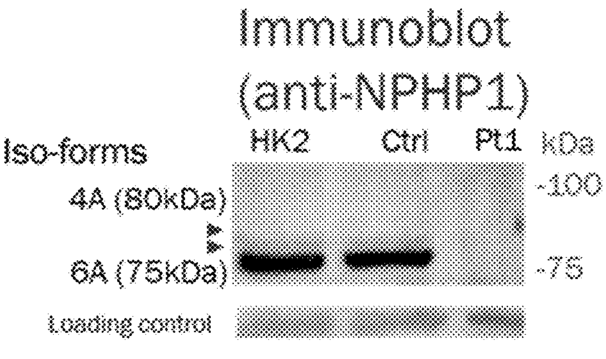

To identify compounds for treating diseases associated with ciliopathies such as, for example, NPHP, NPHP patient-derived cells were obtained and cell lines were established. Briefly, peeled renal epithelial cells, which are mostly proximal tubule cells (tbc) recovered from urine of NPHP1-deficient patients, were immortalized by retroviral gene transfer of SV40 T antigen. Cells were fixed and fluorescence-labeled with Hoechst (for nuclei staining), anti-γ-tubulin antibody (for basal bodies staining), and anti-ARL13B antibody (for cilia staining) for detection using immunofluorescence microscopy. In contrast to most normal urine-derived renal epithelial cells (URECs), which have single cilia on each cell (FIG. 1A), most NPHP patient-derived cells do not have cilia (FIG. 1B). Lack of NPHP expression in these NPHP patient-derived cells was further confirmed by RT-PCR (FIG. 1C) and immunoblot (FIG.

1D), which do not show, respectively, detectable level of NPHP RNAs and NPHP protein expression in NPHP patient-derived cells.

Figure 2:
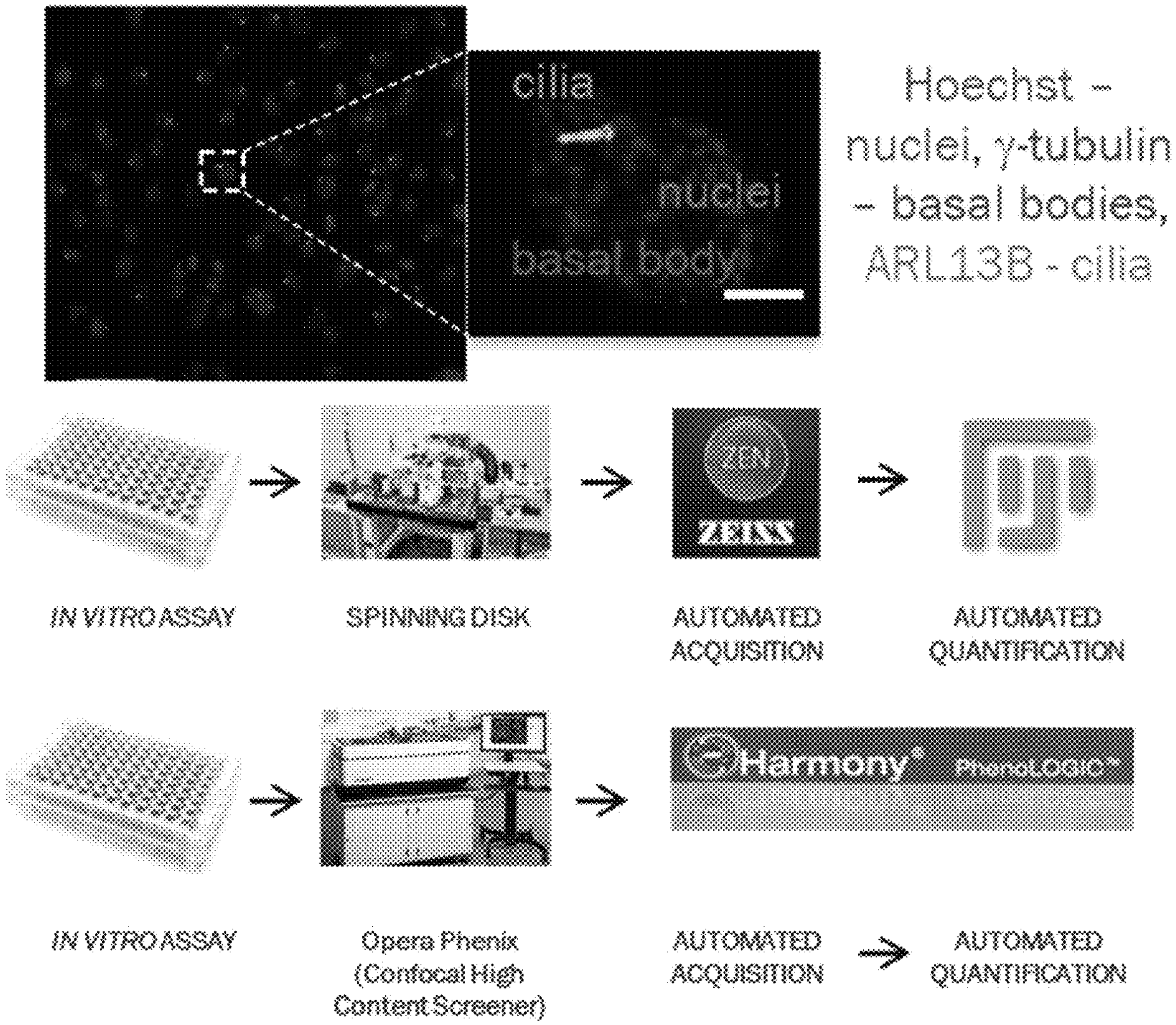
FIG. 2 shows an automated in vitro assay for quantifying ciliogenesis in cells of interest.
Figure 29:
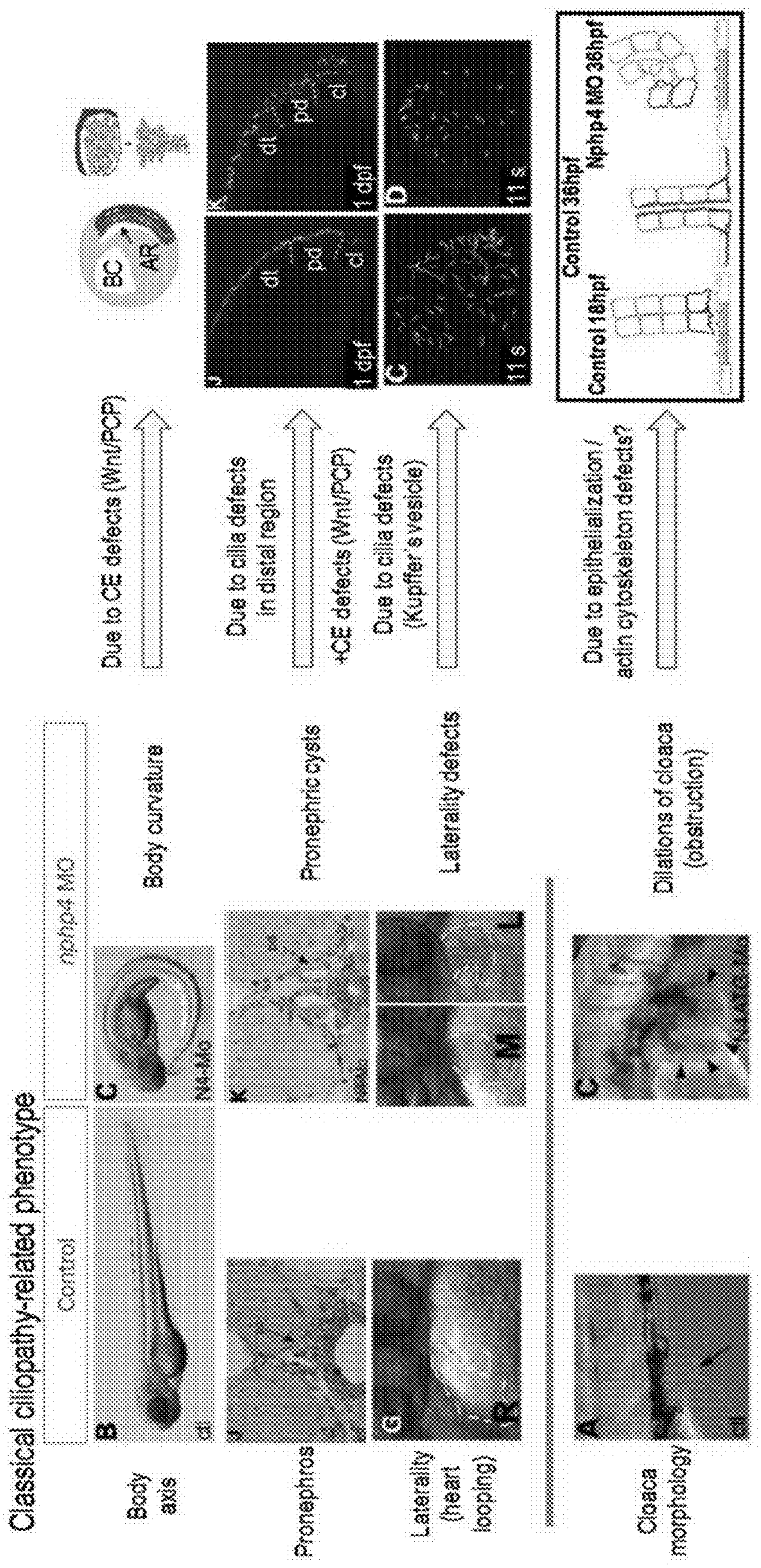
FIG. 29 shows zebrafish NPHP4 MO model.

FIG. 2 shows an automated in vitro assay that may be used to quantify ciliogenesis in cells of interest. Briefly, NPHP patient-derived cells and control cells were cultured in complete media, at 39C (non-permissive temperature for SV40 expression), followed by automatic cilia analysis using immunofluorescence microscopy to measure ciliogenesis, e.g., in terms of % cilia. A spinning disk platform may be used for drug screening (FIG. 5, A-J) and ciliogenesis analysis of G3 multi-OMICs dataset (FIG. 29, A-E). The Opera Phenix platform may be used for other phenotypic analysis (e.g., alprostadil and CP-544326 ciliogenesis titrations, other EP agonist screening based on ciliogenesis, ciliogenesis using other NPHP1 patient-derived cell lines, α-tubulin acetylation analysis).

Figure 3:
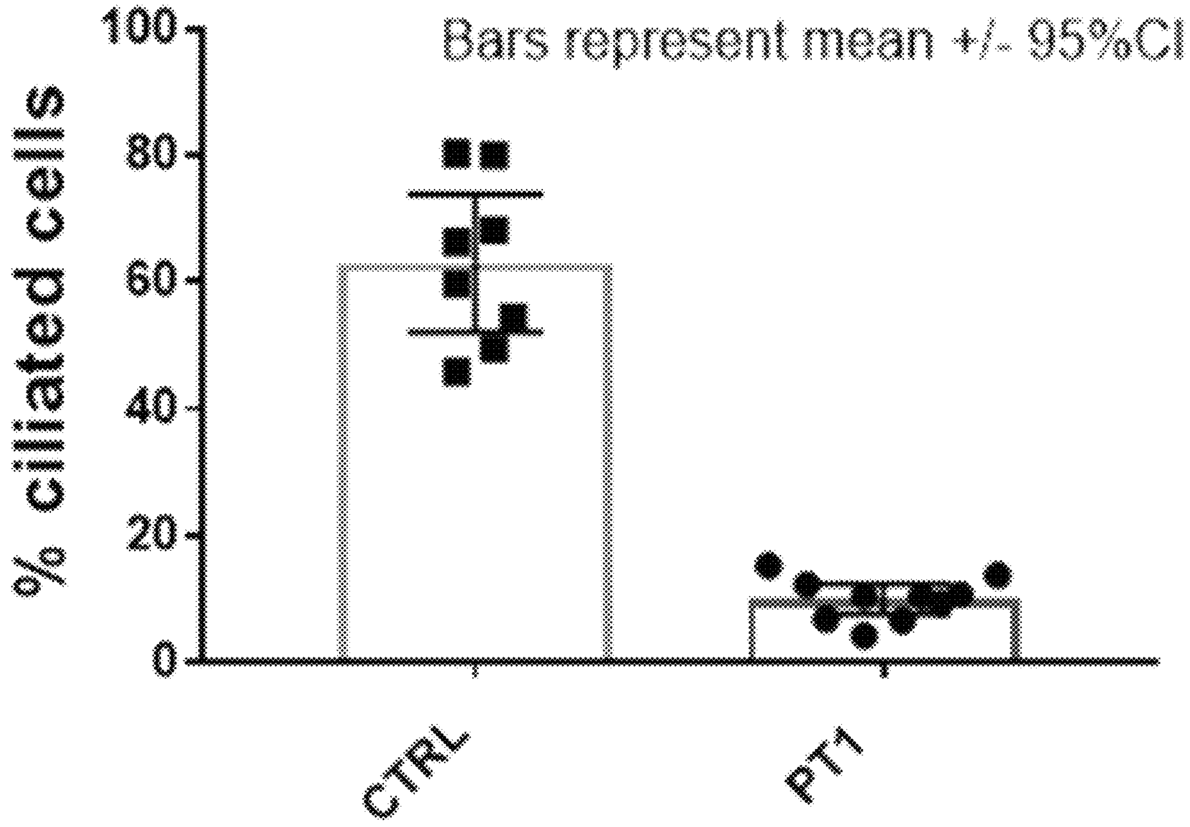
FIG. 3 shows that the percentage of ciliated cells from an NPHP patient (PT1) is significantly lower than that of the control cells (CTRL).

FIG. 3 shows that the percentage of ciliated cells from an NPHP patient (PT1) was significantly lower than found in control cells (CTRL) ($p=0.0065$).

Drug Screening

Figure 4:
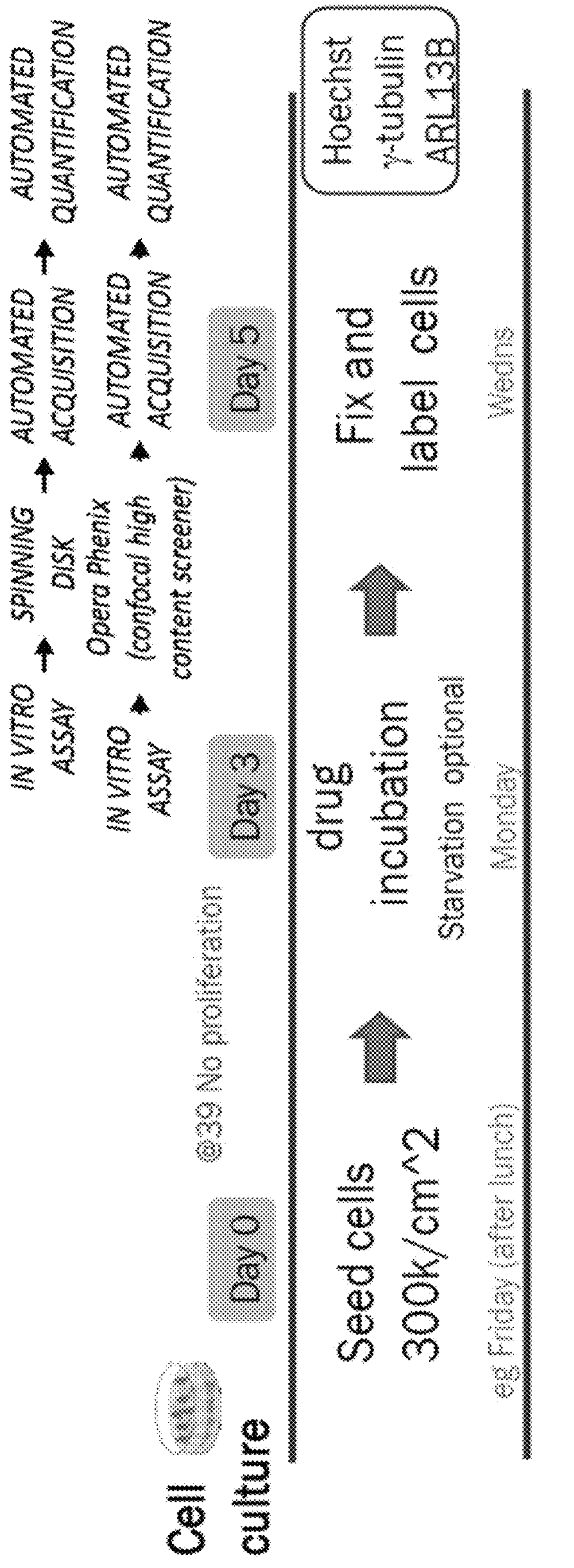
FIG. 4 is a schematic drawing showing the steps of a novel cilia-based assay.

The cilia-based assay described above may be used to identify compounds that restore ciliogenesis. FIG. 4 shows processes of cilia-based assay, in which cells may be seeded in cell culture (e.g., a 96-well plate) on Day 0, incubated with drug candidates on Day 3, and fixed and fluorescence-labeled with Hoechst, anti-γ-tubulin antibody, and anti-ARL13B antibody on Day 5, for example. Automated random acquisition of 35 images per well may be performed, for example. Each image may have z-stack of 10 images taken at <1 μm intervals. Consecutive imaging of nucleus (Hoechst at 461 nm), basal body (γ-tubulin at 555 nm) and cilia (ARL13b at 647 nm) may be obtained.

Figure 5:
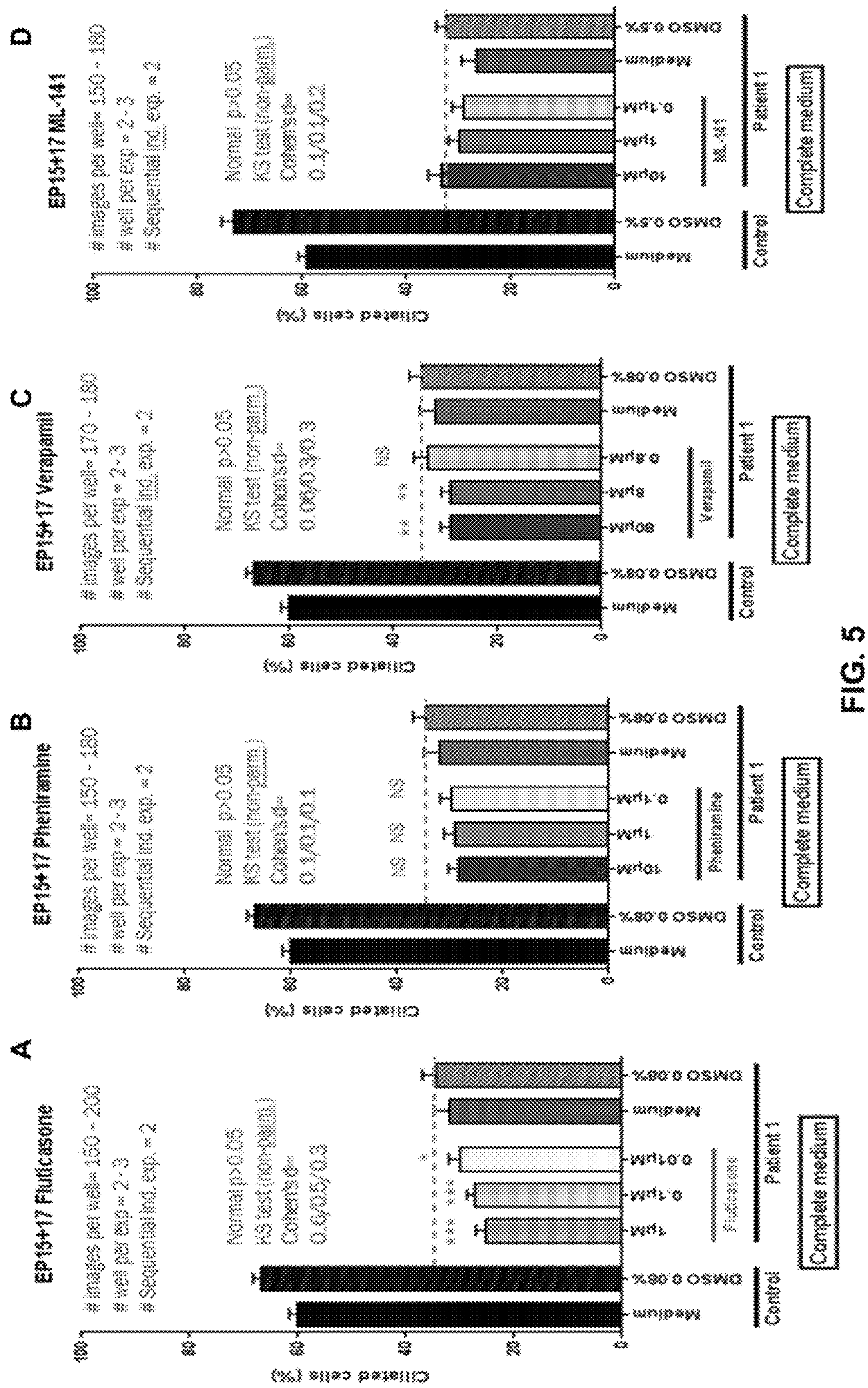
FIG. 5 shows the effects of: (A) fluticasone, (B) pheniramine, (C) verapamil, (D) ML-141, (E) mitoxantrone, (F) tropisetron, (G) ethopropazine, (H) cyproheptadine, (I) paclitaxel and (J) simvastatin on ciliogenesis, as compared with DMSO.
Figure 5:
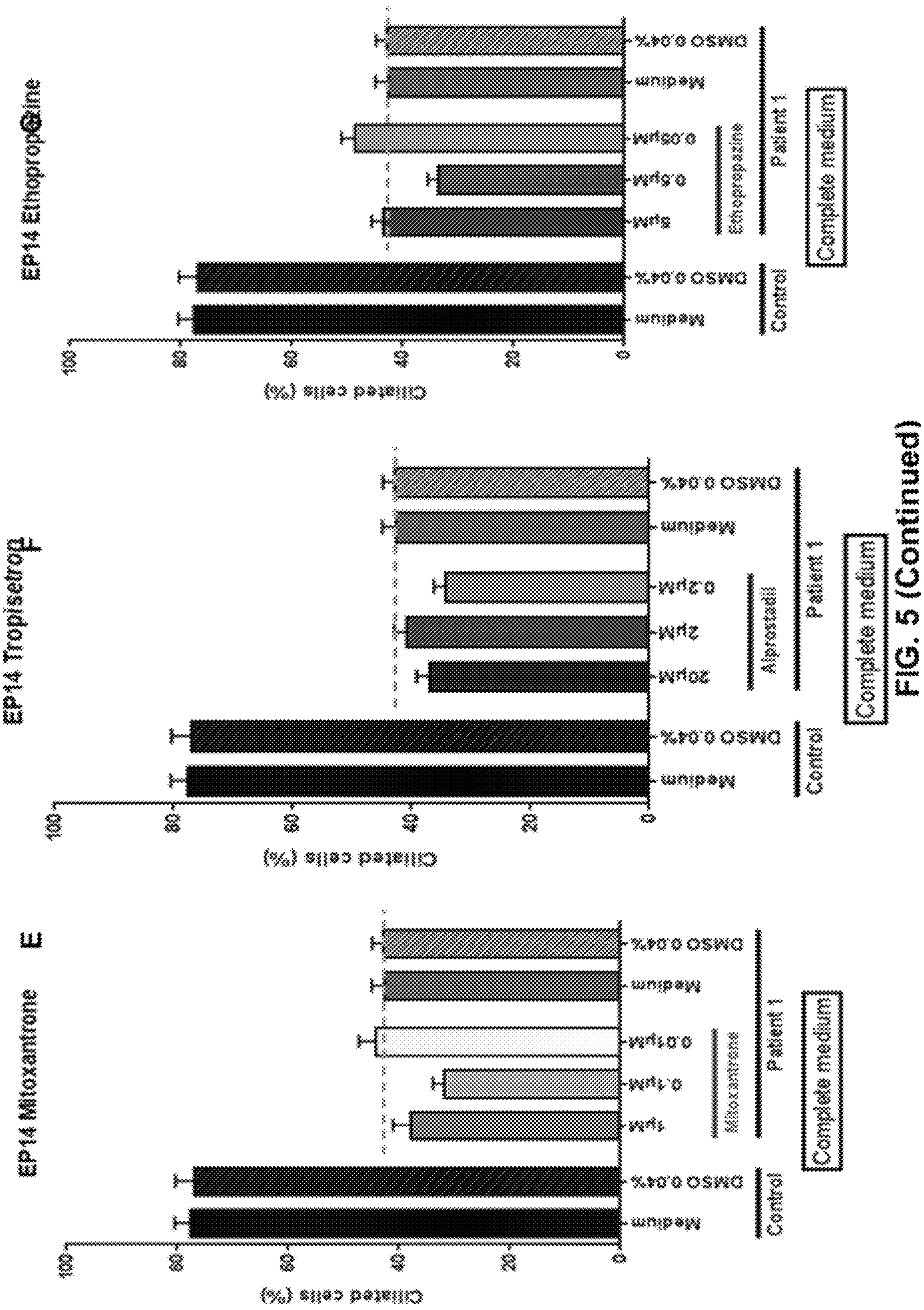
Figure 5:
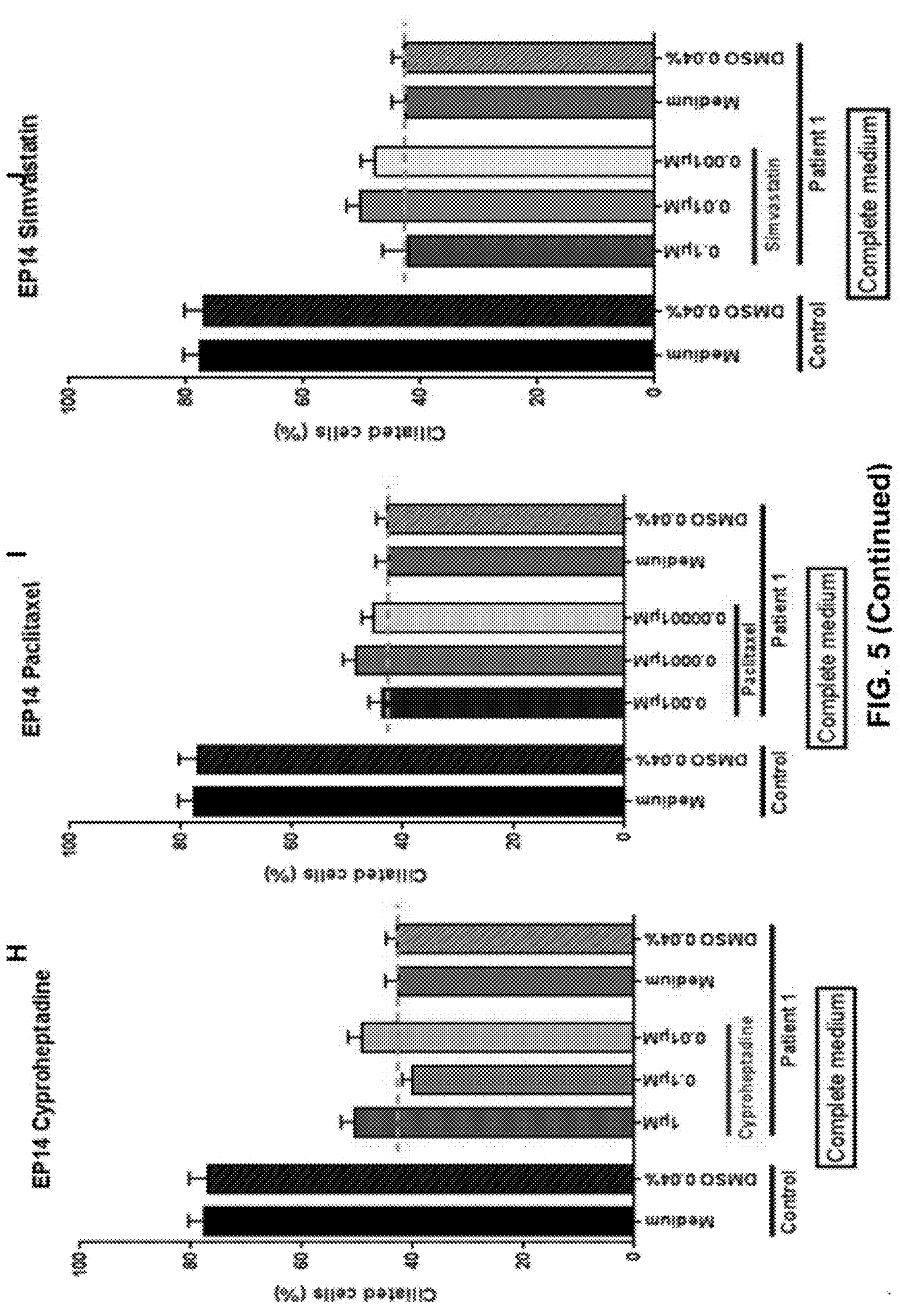
Figure 6:
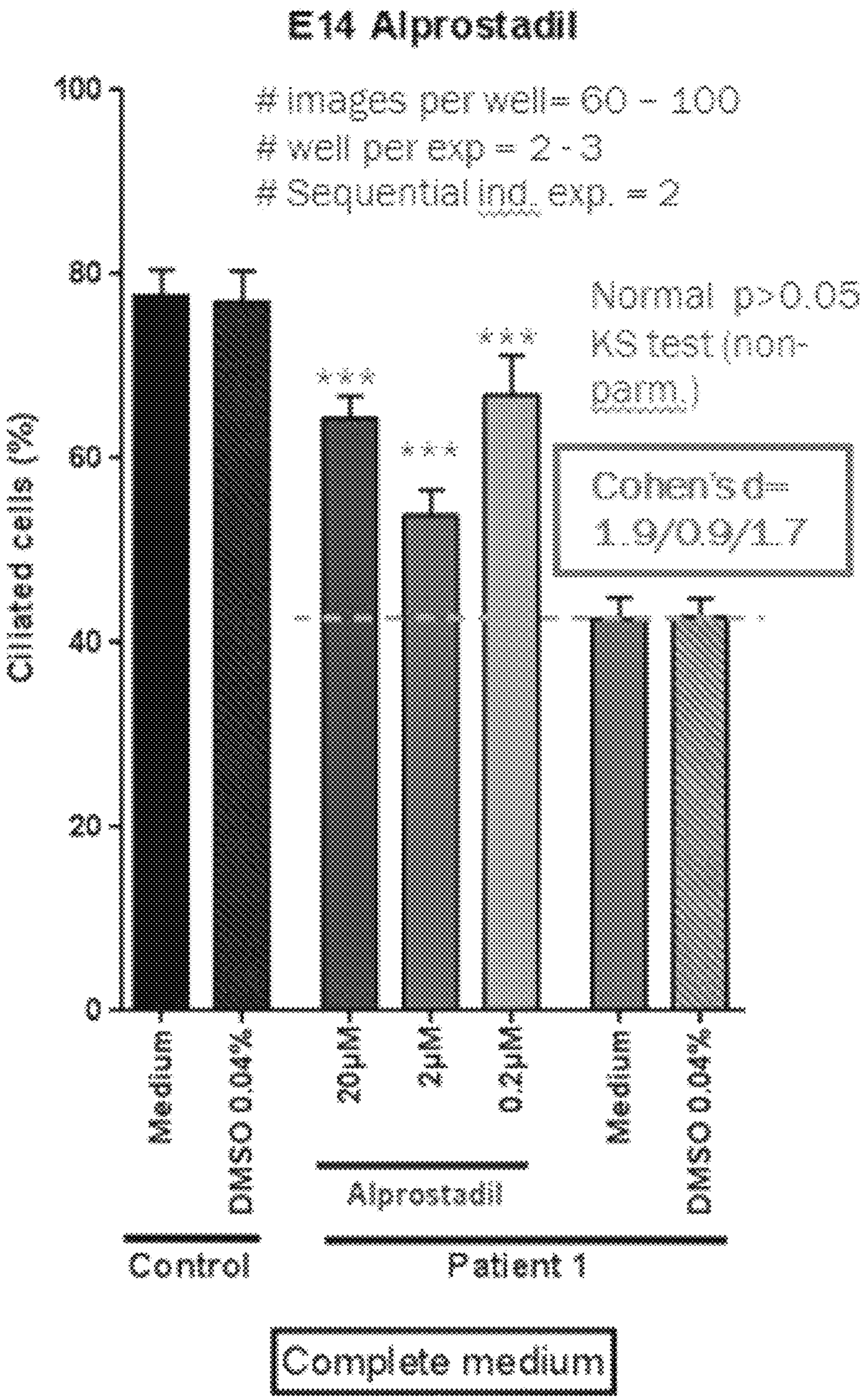
FIG. 6 shows the effects of alprostadil on ciliogenesis, as compared with DMSO.

Using processes shown in FIG. 4, NPHP patient-derived cells were treated with several drug candidates to identify drugs that could restore ciliogenesis. FIG. 5, panels A-J, show that fluticasone, pheniramine, verapamil, ML-141, mitoxantrone, tropisetron, ethopropazine, cyproheptadine, paclitaxel, and simvastatin, respectively, at various tested concentrations did not have a significant effect on ciliogenesis as compared with DMSO. Surprisingly, FIG. 6 shows that alprostadil, compared to DMSO, significantly restored ciliogenesis in NPHP patient-derived cells by increasing the percentage of ciliated cells.

Alprostadil, i.e., prostaglandin E1 (PGE1), has the chemical structure (PGE1)

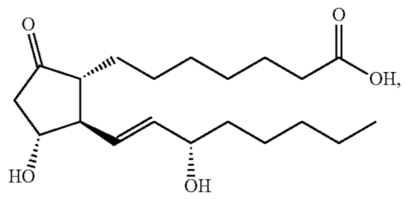

which exhibits activities for vasodilation, inhibition of platelet aggregation, and stimulation of intestinal and uterine smooth muscle for treating heart diseases and erectile dysfunction. Alprostadil may act as an agonist by binding E-type prostaglandin (EP) receptors, which are G protein-coupled receptors (GPCRs), with $IC_{50}$ values of 36, 10, 1.1 and 2.1 nM for EP1, EP2, EP3 and EP4, respectively. GPCRs stimulate adenylate cyclase and subsequently raise in intracellular cAMP.

As used herein, a "GPCR agonist" includes compositions that activate a GPCR to mimic the action of an endogenous signaling molecule specific to that receptor. A "GPCR antagonist" includes compositions that inhibit GPCR activity. GPCR activity may be measured by ability to bind to an effector signaling molecule such as G-protein. An "activated GPCR" is one that is capable of interacting with and activating a G-protein. An inhibited receptor may have a reduced ability to bind extracellular ligand and/or productively interact with, and activate a G-protein.

GPCR agonist treatment, e.g., with taprenepag isopropyl, may be carried out at a concentration of, e.g., from about 0.1 mg/kg to about 20 mg/kg, from about 0.5 mg/kg to about 20 mg/kg, from about 1 mg/kg to about 20 mg/kg, from about 2 mg/kg to about 20 mg/kg; from about 3 mg/kg to about 20 mg/kg; from about 4 mg/kg to about 20 mg/kg; from about 5 mg/kg to about 20 mg/kg; from about 6 mg/kg to about 20 mg/kg, from about 7 mg/kg to about 20 mg/kg, from about 8 mg/kg to about 20 mg/kg, from about 9 mg/kg to about 20 mg/kg, from about 10 mg/kg to about 20 mg/kg, from about 12 mg/kg to about 20 mg/kg, from about 14 mg/kg to about 20 mg/kg, from about 16 mg/kg to about 20 mg/kg, or from about 18 mg/kg to about 20 mg/kg, at a frequency of, e.g., every day, every 2 days, every 3 days, every 4 days, every 5 days, every 6 days, every 7 days, every 8 days, every 9 days, every 10 days, once a week, once every 2 weeks, once every 3 weeks, or once a month.

Figure 7A:
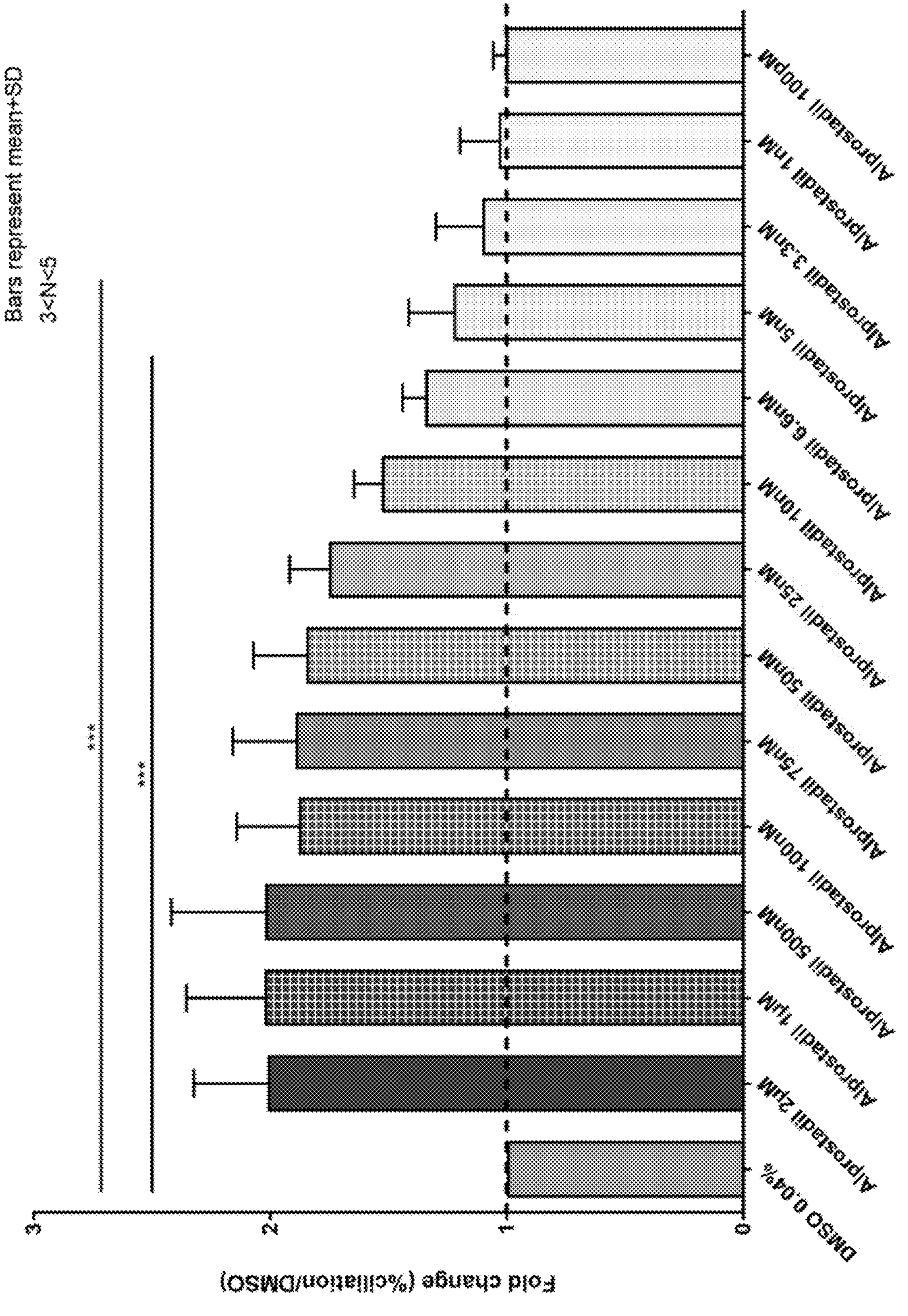
FIG. 7A shows the alprostadil dose response for ciliogenesis, as compared with DMSO.
Figure 7B:
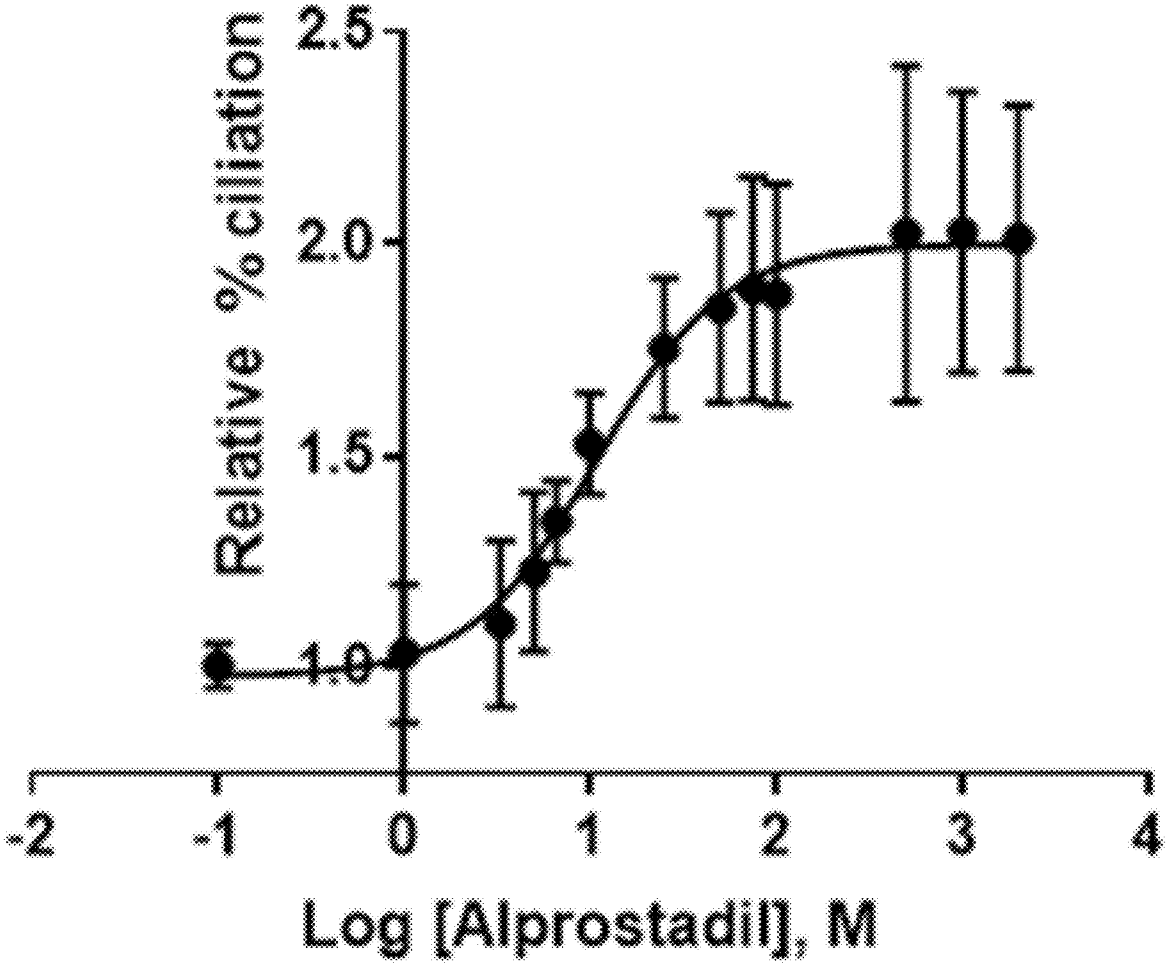
FIG. 7B shows the corresponding semi-log representation for $IC_{50}$ determination.

To determine effective concentration of alprostadil for restoring ciliogenesis, automatic cilia analysis was performed with alprostadil titration from 1 nM to 2 μM (FIG. 7A) and from 100 pM to 2 μM (FIG. 7B). Effective concentrations of GPCR agonists, e.g., alprostadil, may be from about 1 pM to about 10 μM, from about 10 pM to about 5 μM, from about 50 pM to about 5 pM μM, from about 100 pM to about 5 μM, from about 1 nM to about 5 μM, from about 1 nM to about 4 μM, from about 1 nM to about 3 μM, from about 1 nM to about 2.5 μM, from about 1 nM to about 2 μM, from about 10 nM to about 2 μM, from about 100 nM to about 2 μM, from about 500 nM to about 2 μM, or from about 1 μM to about 2 μM. FIG. 7C shows the corresponding semi-log representation for $IC_{50}$ determination, indicating that alprostadil significantly increases % ciliated cells in a dose-dependent manner in NPHP patient-derived cells.

Figure 8A:
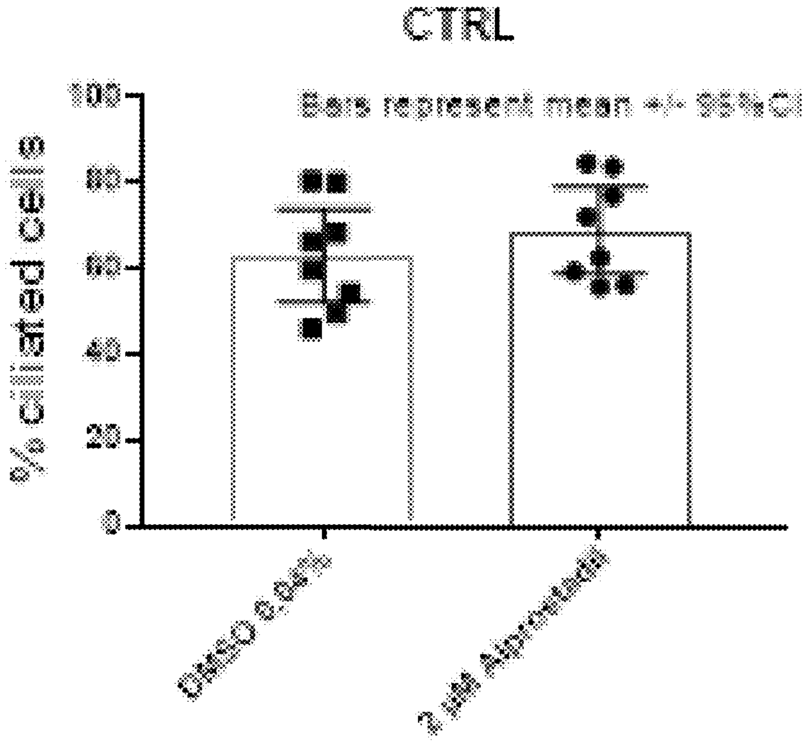
FIGS. 8A-8C show meta-analyses of results obtained in multiple ciliogenesis experiments upon treatment with alprostadil.
Figure 8B:
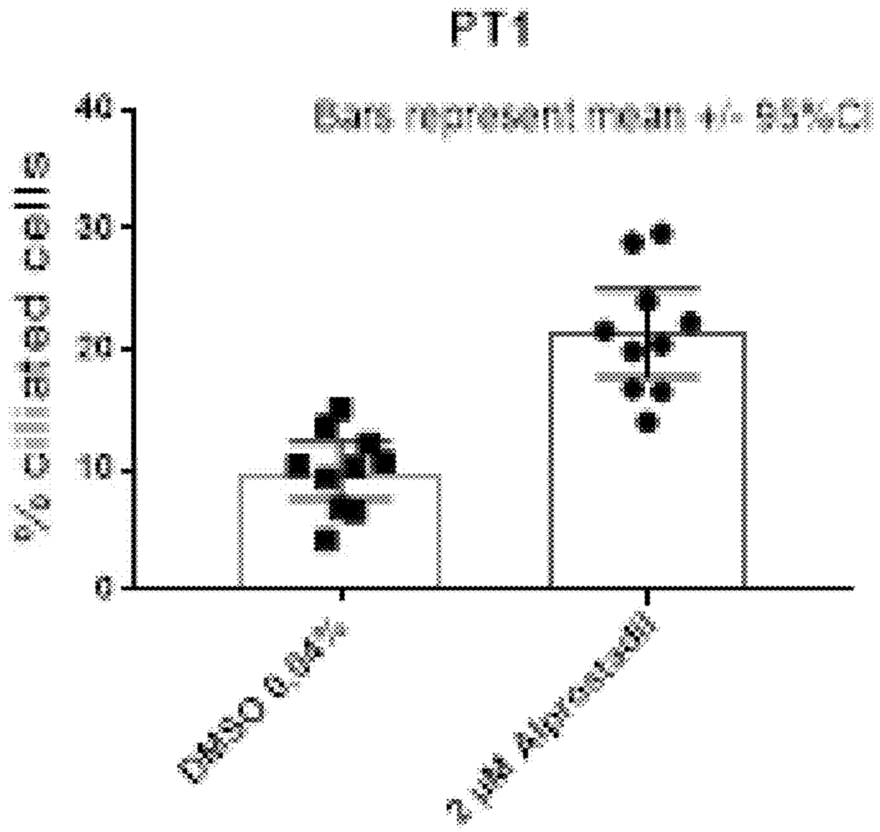
Figure 8C:
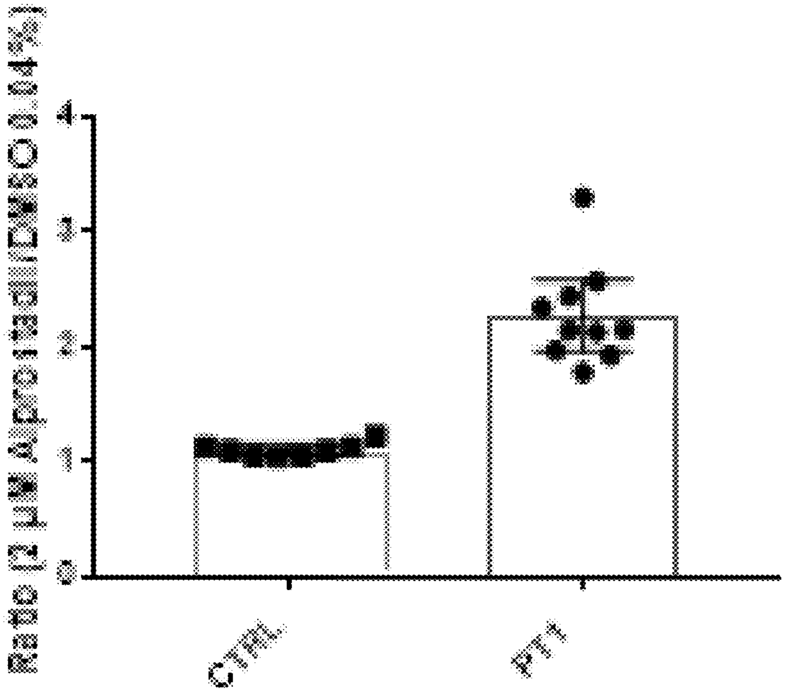

FIGS. 8A-8C and 9 (panels A-D) show a meta-analysis indicating that alprostadil treatment (2 μM) does not significantly affect ciliogenesis in control normal epithelial cells (CTRL), as compared with the control (DMSO 0.04%) (FIG. 8A). In contrast, alprostadil treatment significantly increases ciliogenesis in NPHP patient-derived cells (PT1), as compared with the control (DMSO 0.04%) (FIG. 8B). FIG. 8C shows about two-fold increase in the effect of alprostadil on ciliogenesis in NPHP patient-derived cells versus that in control cells receiving no alprostadil treatment, i.e., the control (DMSO 0.04%).

Figure 9:
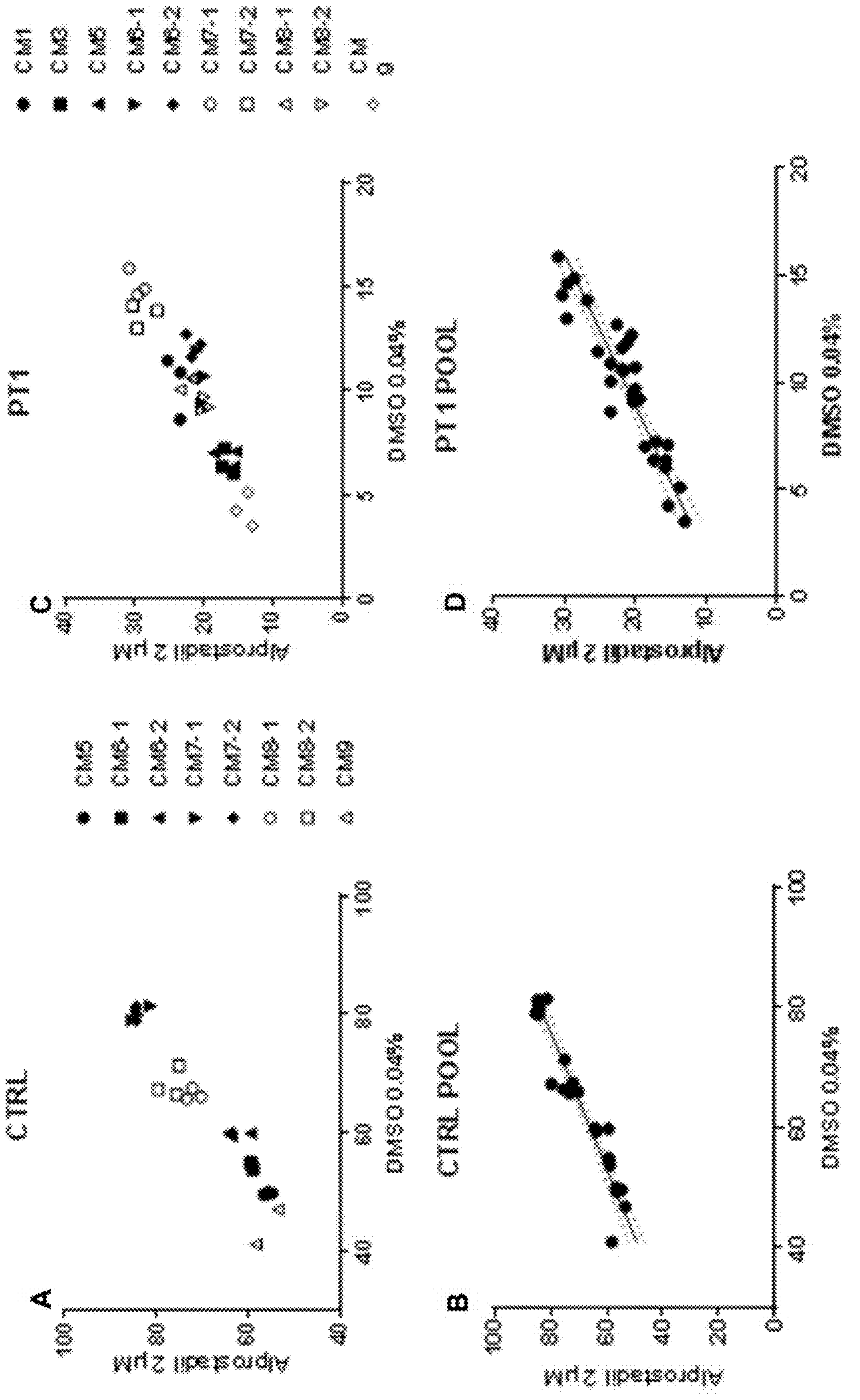
FIG. 9 shows (A-D) show meta-analyses of results obtained in multiple ciliogenesis experiments upon treatment with alprostadil, distinguishing data per experiment.

Meta-analysis also shows a near linear effect of alprostadil dose on ciliogenesis. FIG. 9 (panels A & B), for example, shows an $R^2$ value of 0.9194 regarding the effect of alprostadil on ciliogenesis in control normal epithelial cells. Similarly, FIG. 9 (panels C & D) shows an $R^2$ value of 0.8489 regarding the effect of alprostadil on ciliogenesis in NPHP patient-derived cells.

Figure 10:
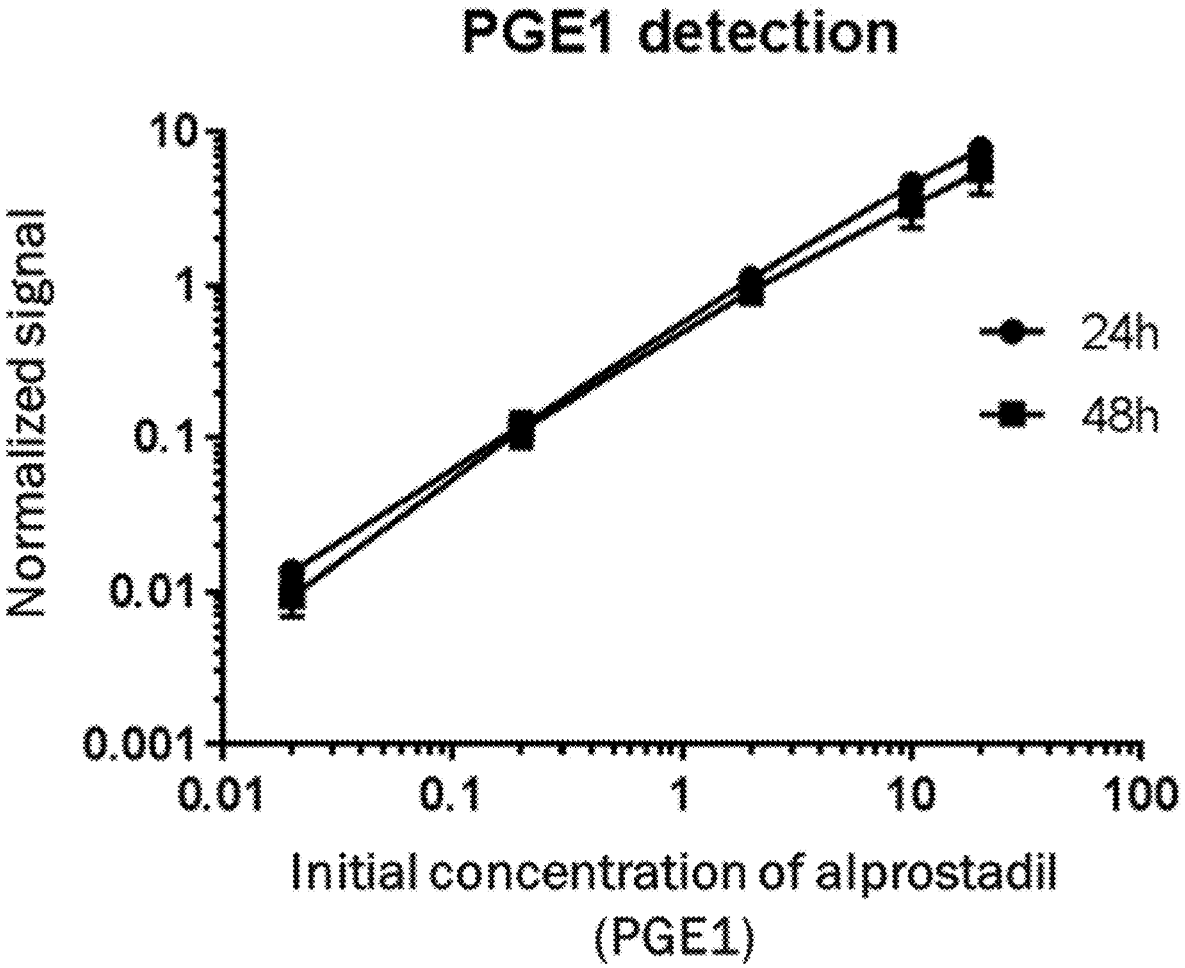
FIG. 10 shows the stability of PGE1 under experimental conditions.

To determine the stability of alprostadil (PGE1), supernatants were obtained from urine-derived renal epithelial cells (URECs) exposed to different concentrations of alprostadil after 24 and 48 hours of exposure. Samples were then extracted and split into equal parts for analysis on LC/MS/MS and Polar LC platforms. FIG. 10 shows that PGE1 is stable under the experimental conditions.

In addition to PGE1, other EP agonists, such as prostaglandin E2 (PGE2 or dinoprostone), having the chemical structure (PGE2)

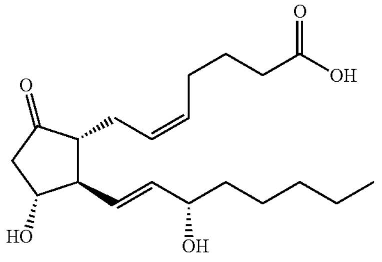

and its long-acting derivative, 16,16-dimethyl-PGE2 (dmPGE2), having the chemical structure (dmPGE2)

Figure 11A:
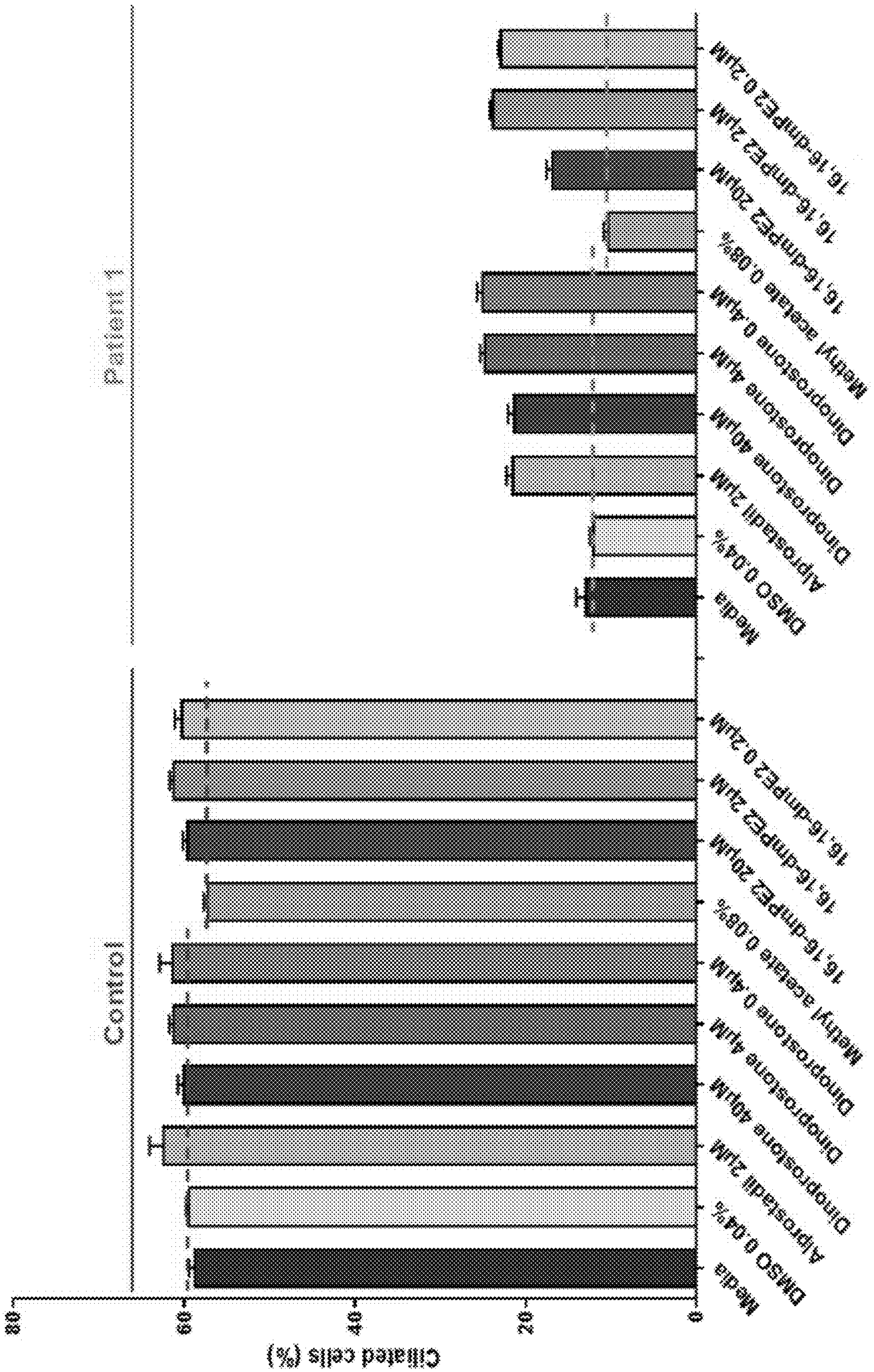
FIG. 11A shows the effect of alprostadil (PGE1), dinoprostone (PGE2), and 16, 16-dimethyl-PGE2 (dmPGE2) on ciliogenesis.

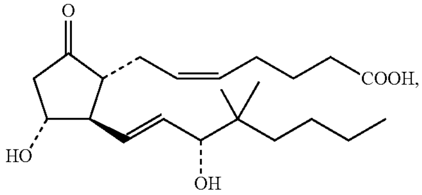

were also tested for their ability to restore ciliogenesis. FIG. 11A shows that PGE2 and dmPGE2 have ciliogenesis restorative effects similar to that of alprostadil in NPHP patient-derived cells, while no significant effect was observed in control normal cells. A slight decrease in restoration of ciliogenesis in NPHP patient-derived cells was observed at the highest concentration (40 μM dinoprostone and 20 μM dmPGE2), which may be due to cytotoxicity.

Figure 11B:
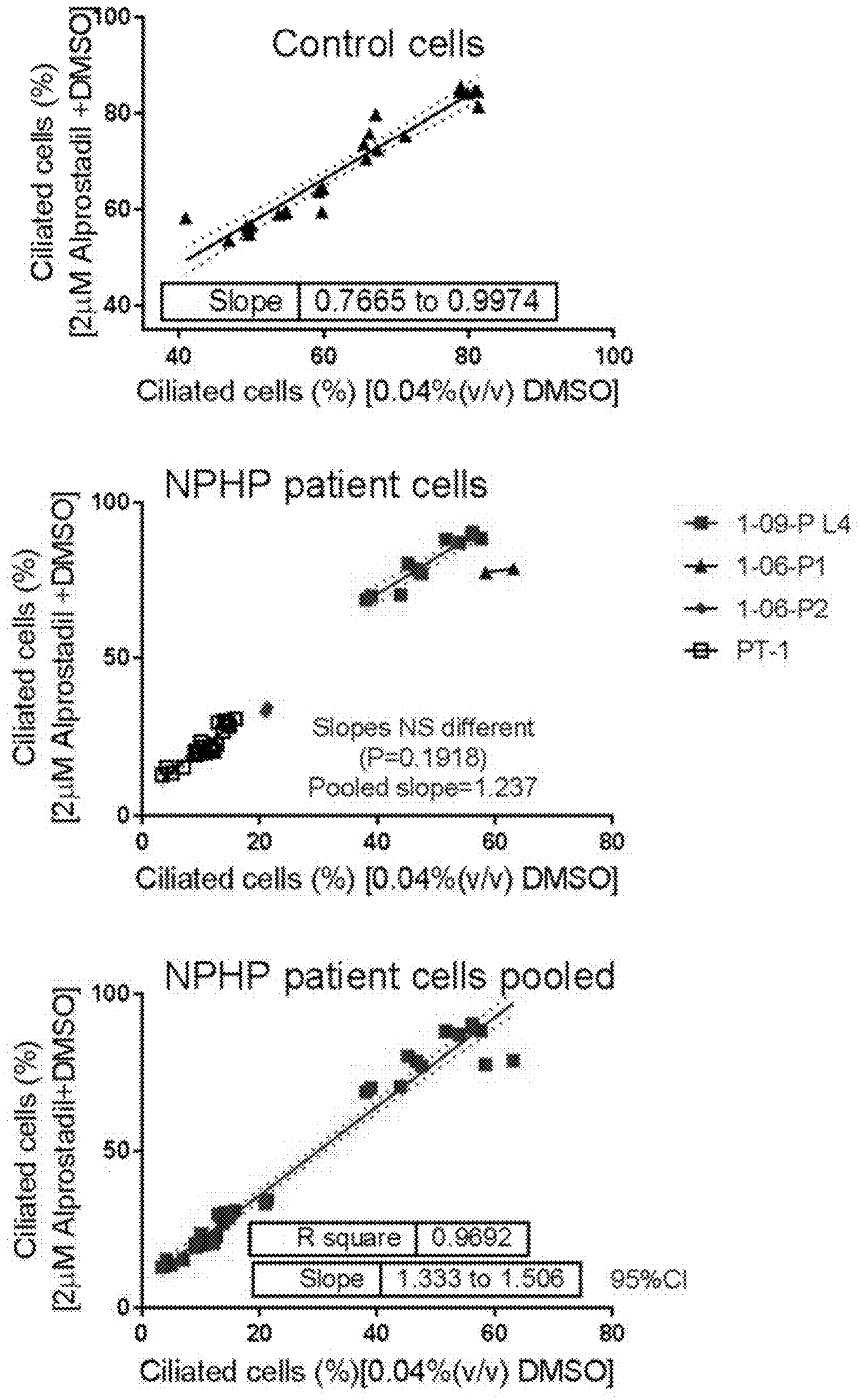
FIG. 11B shows the effect of alprostadil (PGE1) on NPHP1-deleted patient-derived cell lines.

To test the effect of alprostadil (PGE1) on NPHP1-deleted cells, cell lines derived from NPHP1(del) patients, e.g., PT1, 1-03-P, 1-06-P1, 1-06-P2, 1-09-P, 1-10-P, and 1-12-P, were treated with alprostadil (2 μM) or DMSO. FIG. 11B shows alprostadil significantly increases ciliogenesis rate in NPHP1-deleted cells, whereas alprostadil had no significant effect on ciliogenesis rate in normal control cells, suggesting alprostadil is effective in restoring ciliogenesis in NPHP1-deleted patients.

Figure 11C:
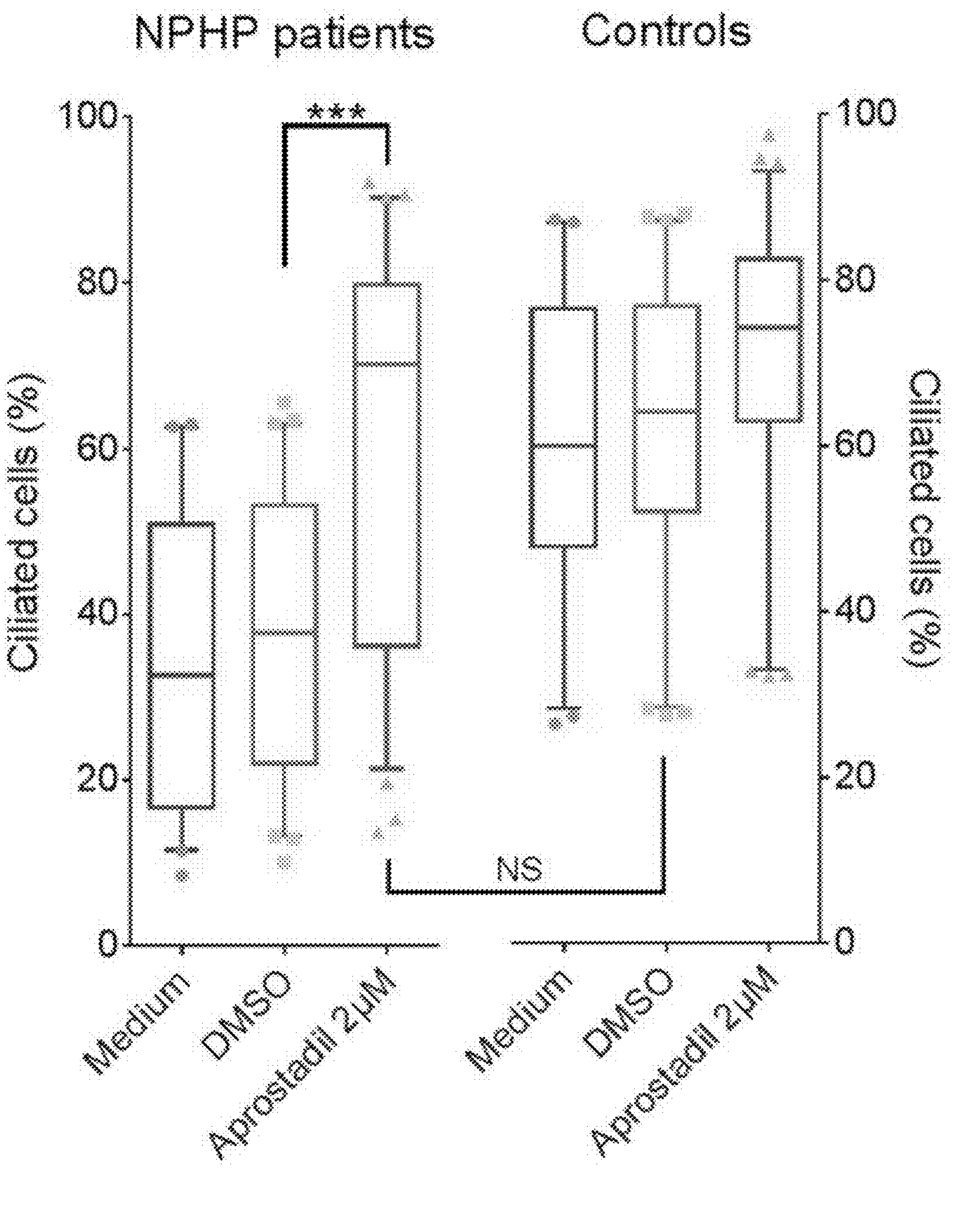
FIG. 11C shows cilio meta-analysis.

Meta-analysis in FIG. 11C shows linear regression analysis of previous data, where the slope reflects the effect of alprostadil on ciliogenesis of control cells and multiple NPHP patient-derived cell lines, each symbol representing an independent experiment and each color representing a patient cell line (named as 1-09-P L4, 1-06-P1, 1-06-P2, PT-1). Linear regression for control normal epithelial cells data shows a slope value between 0.7665 and 0.9974 suggesting the lack of effect of alprostadil on ciliogenesis. In contrast, linear regression for multiple NPHP patient-derived cells shows a pooled slope value of 1.414 or a range of slope values of 1.333 to 1.506, indicating a stimulating effect of alprostadil on ciliogenesis.

Prostaglandins are found in most human tissues and are synthesized from essential fatty acids. Structural differences between various prostaglandins account for varying biological activity. Prostanoids including prostaglandins are abundantly produced in the kidney. The prostanoids originate from the release of arachadonic acid (AA) from membrane phospholipids by phospholipase A2. Arachadonic acid is subjected to bisoxygenase and peroxidase activities of the cyclooxygenases (or prostaglandin G/H synthases) to form prostaglandin G2 (PGG2) and then prostaglandin H2 (PGH2). PGH2 is the substrate for the synthases including PGE2 synthase, PGD2 synthase, prostacyclin synthase, PGF2a synthase (PGF2a can also be synthesized directly from PGE2) and thromboxane synthase to synthesize the individual classes of prostanoids including PGE2. These classes all have discrete receptor subtypes including EP1-4, through which they initiate their actions. The cyclooxygenases 1 and 2 (COX1 and COX2) are the primary targets of non-steroidal anti-inflammatory drugs (NSAIDs), but these may be specific for one isoform or another, selective, or nonselective. Blocking the production of PGH2 via COX inhibition can reduce the levels of all downstream prostanoids.

PGE in Ciliogenesis

PGE2 is the best characterized prostanoid in renal pathophysiology. PGE2 is synthesized by COX1 and COX2 and exported via the Lkt/ABCC4 transporter on the cell membrane. Released PGE2 binds to the EP4 receptor on the cilium, resulting in the activation of GPCRs (Gs) and adenylate cyclase (AC) to increase cAMP, thereby increasing the anterograde IFT and enhancing ciliogenesis.

Cilia formation and elongation require the COX-Lkt/ABCC4-EP4 signaling cascade (in mouse kidney collecting duct cells IMCD3 and in a zebrafish model). cAMP-dependent kinase signaling is known to increase anterograde IFT during ciliogenesis. Lkt/ABCC4-mediated PGE2 signaling affects cAMP level and promotes ciliogenesis via an increase in the anterograde velocity of IFT. PGE2 treatment causes an increase of intracellular cAMP but not $Ca^{2+}$ during ciliogenesis in IMCD3 cells. PGE2 acts in an autocrine and/or paracrine manner, as cells can respond to PGE2 released by either themselves or by their neighbors. In human cancer cells, interaction of PGE2 with EP4 receptor induces Wnt/β-catenin signalling, resulting in COX2 expression, and thereby setting up a positive feedback loop leading to further PGE2 synthesis.

Figure 12:
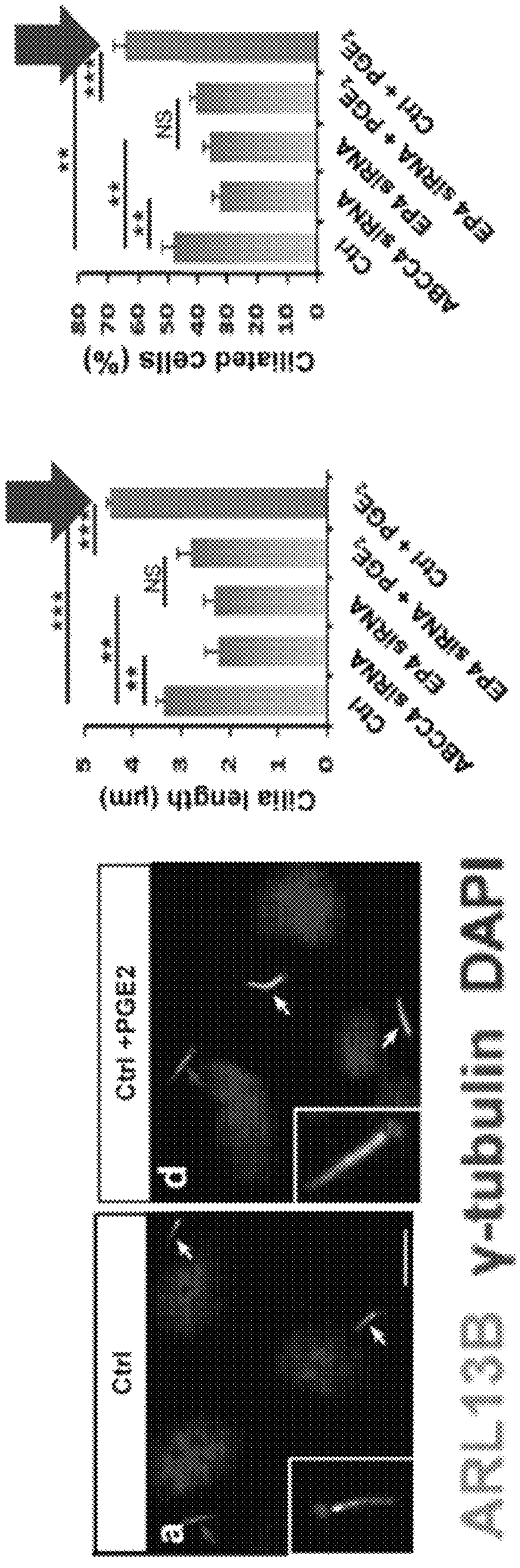
FIG. 12 shows the effect of PGE2 on ciliogenesis.

FIG. 12 shows that addition of exogenous PGE2 increased both cilia length and percentages of ciliated cells in control cells but not in EP4-depleted cells, indicating that EP4 acts downstream of PGE2 signaling during ciliogenesis.

PGE2 is produced by PGE synthase (PGES) and signals by binding to its GPCRs: EP1-4. Activation of EP1 (coupled to $G_q$) increases intracellular $Ca^{2+}$ via PLC. Activation of EP3 (coupled to $G_i$) increases intracellular $Ca^{2+}$ via PLC and/or inhibits cAMP production via adenylate cyclase (AC). Activation of EP2 or EP4 (both coupled to Gs) stimulates cAMP production via AC.

There are about 800 human GPCRs divided into five major phylogenetic families: rhodopsin, secretin, adhesion, glutamate and Frizzled/Taste2. GPCRS are attractive targets for recombinant proteins, small molecule compounds, allosteric ligands or antibodies. 46 GPCRs have served as drug targets for hypertension, pain, ulcers, allergies, alcoholism, obesity, glaucoma, psychotic disorders and HIV. One major impediment, of many, is a general lack of knowledge regarding the association of a putative GPCR with a precise physiological function or disease condition.

Figure 13:
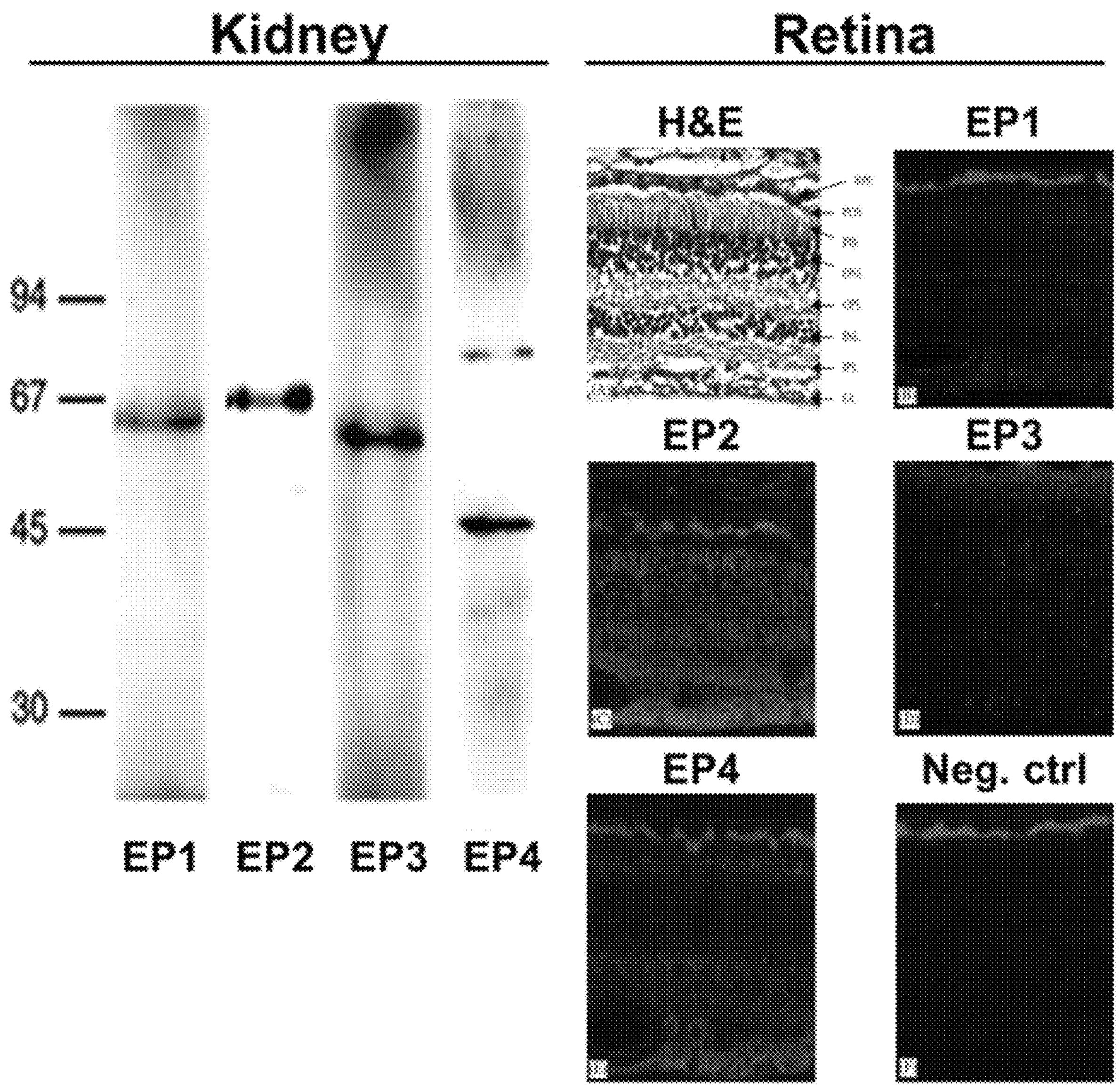
FIG. 13 shows an EP1-4 expression profile in human kidney tissue by western blot and in human retina by immunohistochemistry.

FIG. 13 shows that EP1-4 are expressed in kidney and in retina—both organs being affected in NPHP and NPHP-RC. In the kidney, EP receptors are differentially expressed along the nephron, highlighting distinct functional consequences of activating each EP receptor subtype in the kidney. EP receptors regulate vascular tone in the afferent arteriole, where EP1/EP3 act as vasoconstrictors and EP2/EP4 act as vasodilators. EP1/EP4 regulate proximal tubule transport. EP3 and EP4 regulate thick ascending limb and distal tubule transport. EP4 stimulates renin release from the macula densa. EP2/EP4 vasodilate the vasa recta. EP receptors regulate collecting duct transport whereby EP1 inhibits $Na^+$ reabsorption, EP3 inhibits $H_2O$ reabsorption, and EP4 stimulates $H_2O$ reabsorption.

Figure 14A:
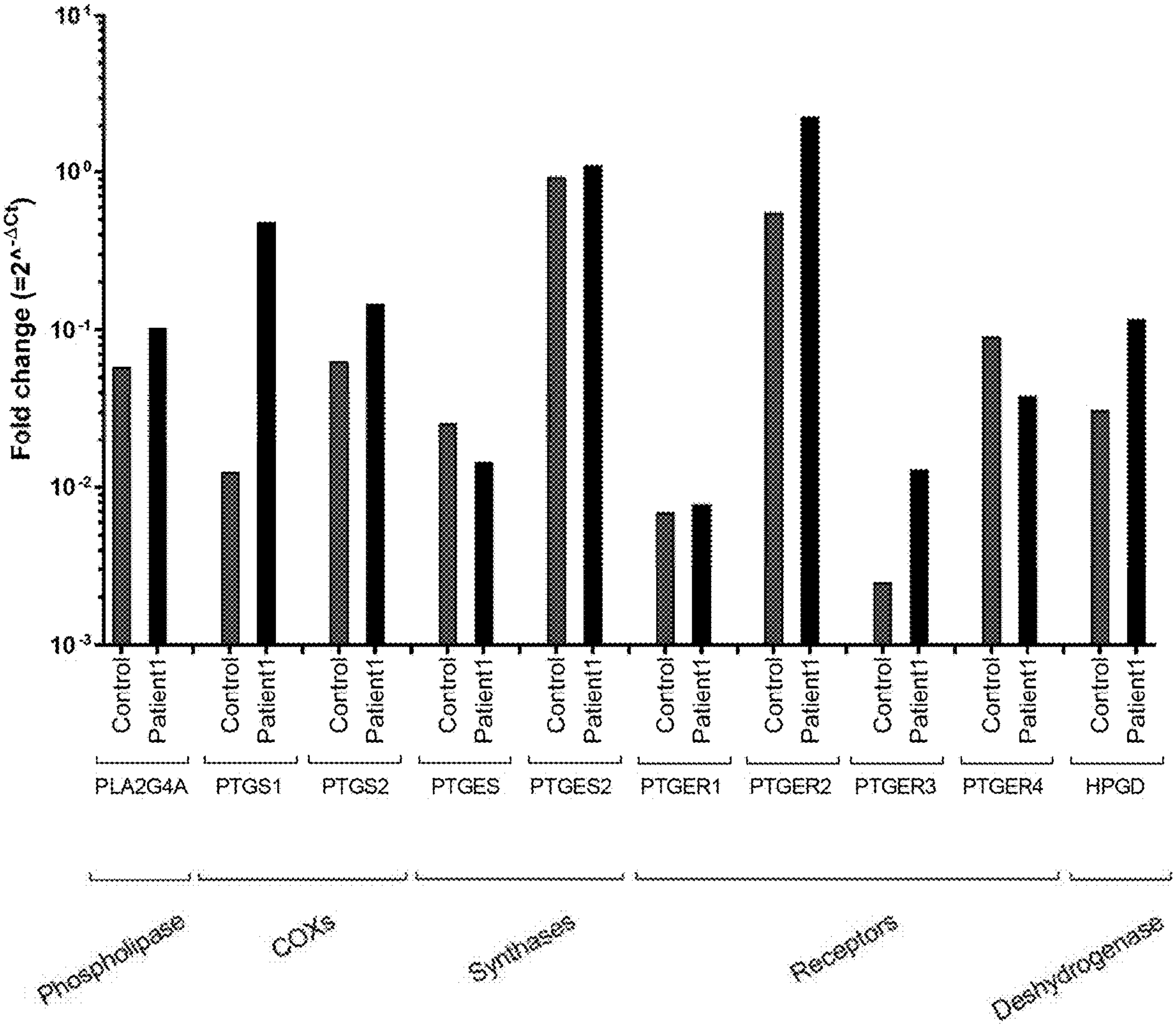
FIG. 14A shows that EP2 and EP4 mRNA are expressed in control and Pt1 derived renal epithelial cells.
Figure 14B:
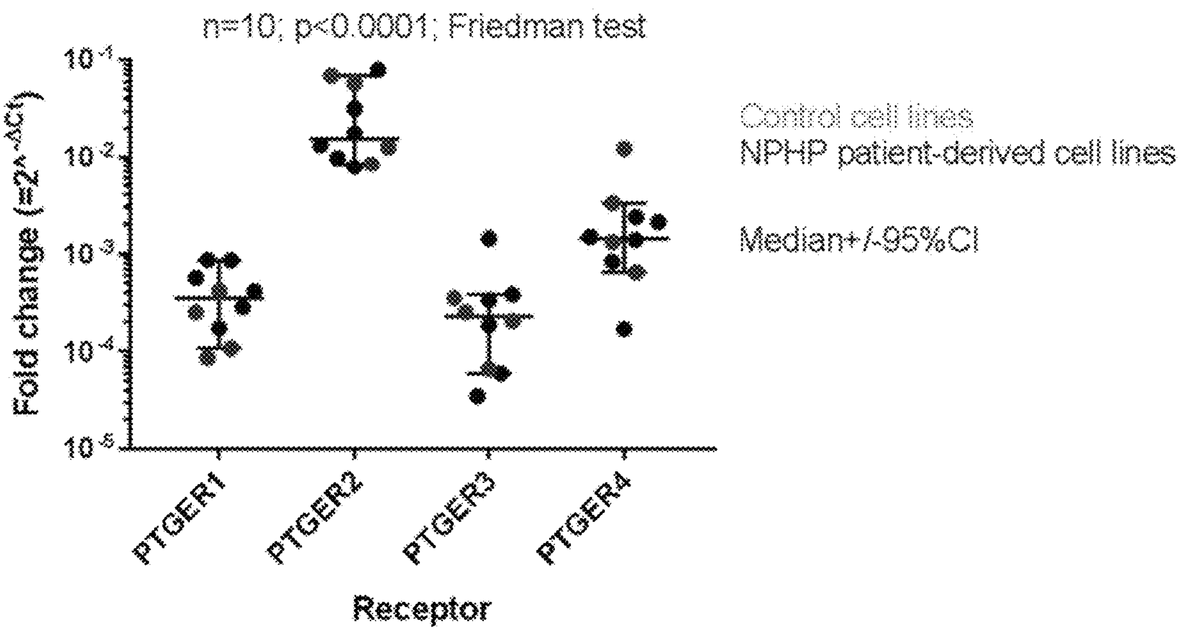
FIG. 14B shows that EP2 is expressed at protein level in control and Pt1-derived renal epithelial cells.
Figure 14C:
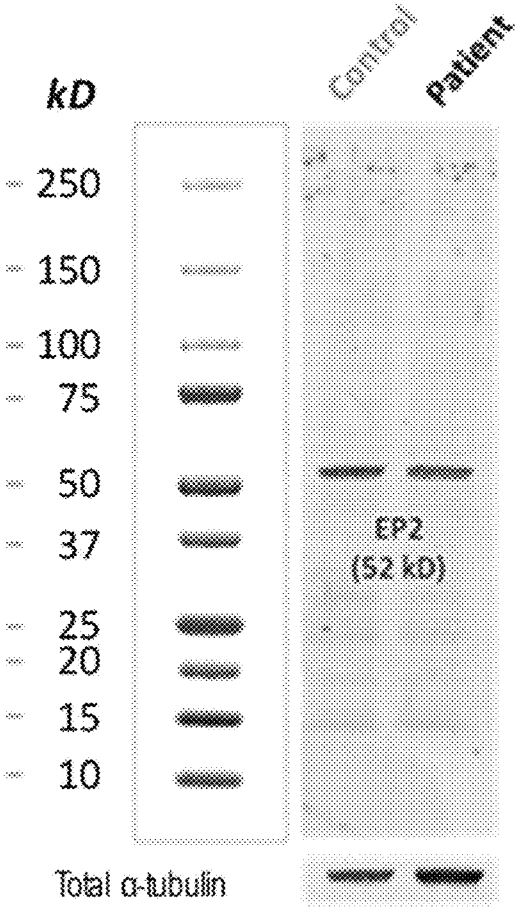
FIG. 14C shows mRNA expression of EP1-4 receptors-encoding genes in multiple control cell lines and in multiple NPHP patients-derived renal epithelial cell lines.

Expression of PG pathway components including EP receptors in URECS was determined by qRT-PCR. FIG. 14A shows that EP2 & EP4 are expressed at mRNA level, and that EP2 is predominantly expressed at mRNA level. FIG. 14B shows EP2 protein expression in URECS.

PGE2 Modulators (EP2)

Selective agonists and antagonists of EP2 receptor are shown in Markovič, T. "Structural features of subtype-selective EP receptor modulators" Drug Discovery Today. 2017; 22(1):57-71, for example, which is incorporated by reference therefor. The first class of agonists comprises ligands that structurally resemble the endogenous ligand PGE2 but incorporate major modifications in the ω-lipophilic chain that contribute to enhanced potency and selectivity. The second class of agonists is a non prostanoid series of pyridyl sulfonamide derivatives, the most potent of which is taprenepag isopropyl (PF 04217329, the prodrug of CP 544326). Taprenepag has a non-prostanoid structure of

CP-544326

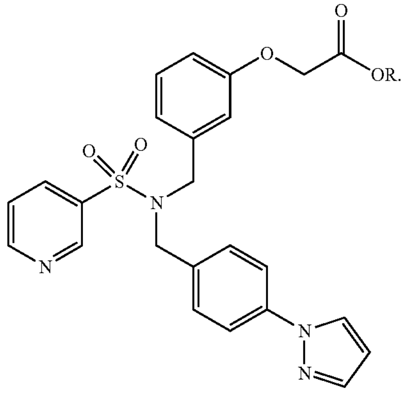

A third class of agonists includes a non-protanoid series of N-phenyl-y-lactam derivatives, including AGN-210669 (simenepag isopropyl) and AGN-210961 (aganepag isopropyl).

PF-04418948, an azetidine-3-carboxylic acid derivative, was the first selective EP2 antagonist, it has an $IC_{50}$ of 16 nM (Kb=1.8 nM), exhibiting >10,000-fold increase in selectivity for the EP2 receptor relative to other prostanoid receptors.

Markovič's FIG. 5 (which is incorporated by reference therefor) shows selective agonists of the EP4 receptor: (a) derivatives based on a functionalised cyclopentane core, (b) derivatives carrying a lactam counterpart of the hydroxycyclopentanone core, and (c) structurally diverse EP4 agonists. The tetrazole feature was introduced into the α-chain in place of the terminal carboxylic acid functionality, with the intention of improving bioavailability, which led to the discovery of L902,688, a sub-nanomolar agonist of the EP4 receptor ($EC_{50}$=0.2 nM). L902,688 has a prostanoid structure of

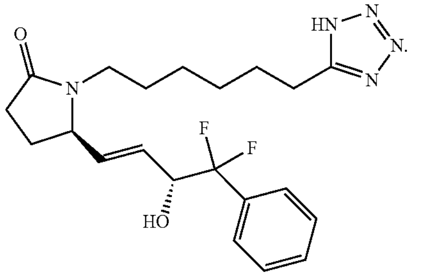 [SMILES: O=C1CC[C@H](/C=C/[C@@H](O)C(F)(F)c2ccccc2)N1CCCCCCc1nnn[nH]1]

The structure of KAG-308

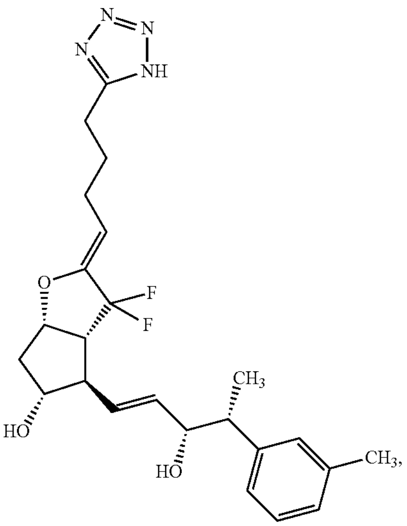 [SMILES: Cc1cccc([C@@H](C)[C@H](O)/C=C/[C@@H]2[C@@H]3[C@H](C[C@H]2O)O/C(=C\CCCc2nnn[nH]2)C3(F)F)c1]

a low nanomolar EP4-agonist, is somewhat unique in the field of EP4 agonists, because it is the only one based on a 7,7-difluoroprostacyclin scaffold.

Markovič's FIG. 6 (which is incorporated by reference therefor) shows selective antagonists of the EP4 receptor and switching in the functional response as a result of minimal structural variation: (a) selective antagonists of the EP4 receptor, and (b) switch of agonism and antagonism at the EP4 receptor. PG-1531, a tri-substituted furan derivative, is a nanomolar EP4 antagonist with an excellent selectivity profile and enhanced aqueous solubility. Through the introduction of minor modifications of the molecule, it is possible to fine-tune the intrinsic activity of the latter at the EP4 receptor (an example is shown in FIG. 17). For example, the intrinsic activity (agonism vs antagonism) has been shown to depend solely on the substitution pattern of the trifluoromethyl substituent on the benzylic group of compounds of FIG. 17 (panel b). A dramatic change of function can be achieved with minimal variation of ligand structure.

FIG. 15 shows PG modulators (agonists and antagonists) tested for their effects on ciliogenesis.

Figure 16A:
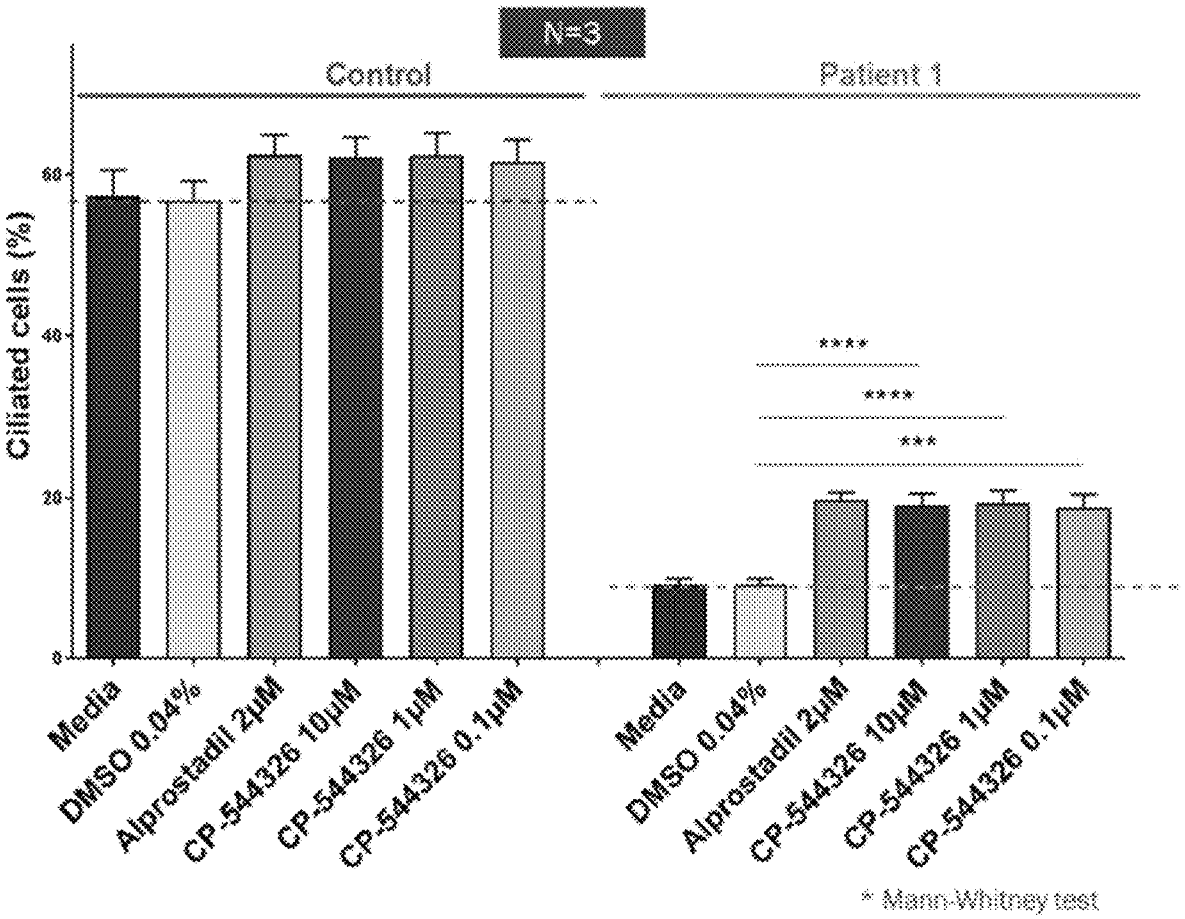
FIG. 16A shows cilio meta-analysis.

FIG. 16A shows that CP-544326, a non-prostanoid EP2 agonist, restores ciliogenesis to a similar level as alprostadil.

Figure 16B:
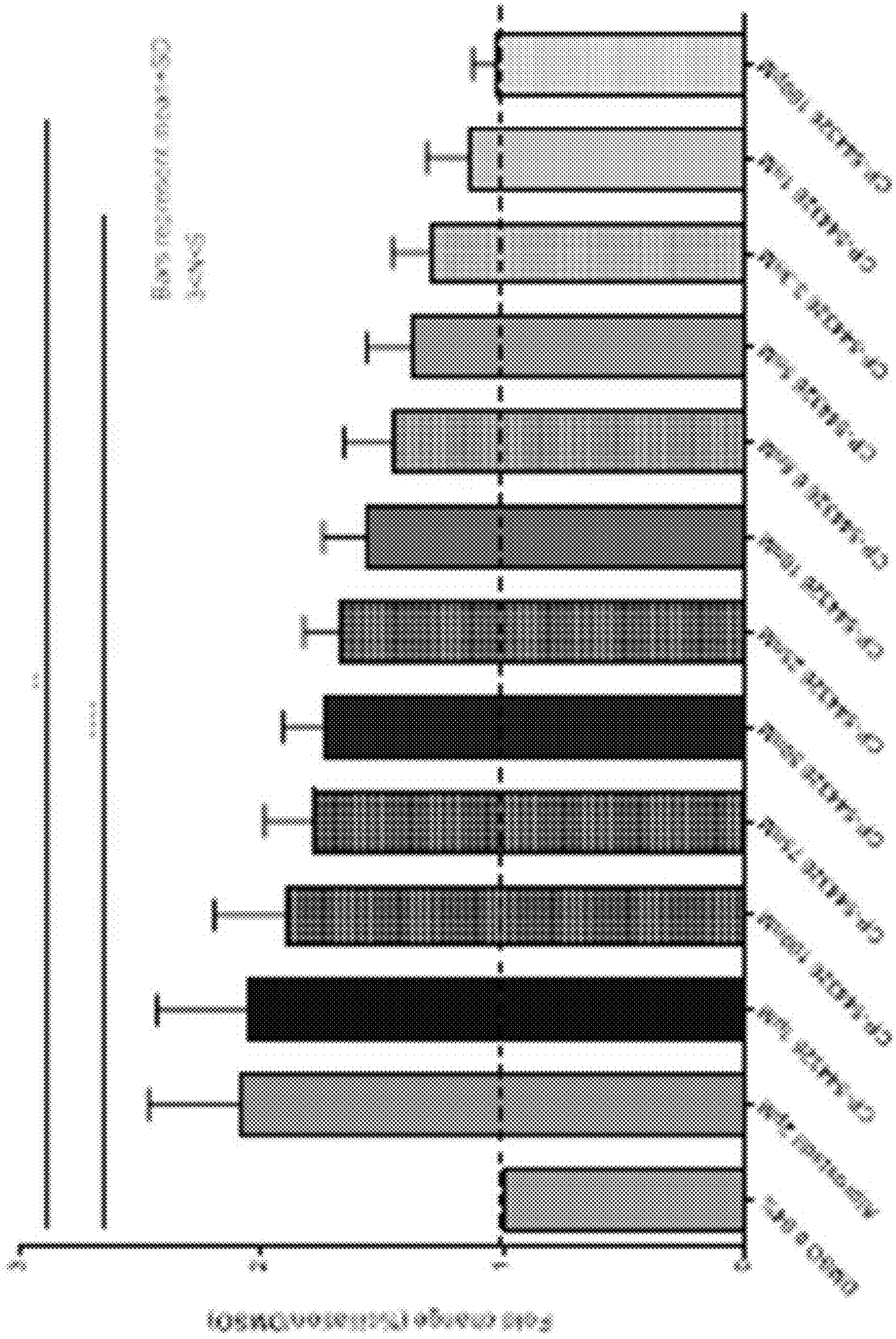
FIG. 16B shows NPHP patient-derived cells treated with CP-544326.
Figure 16C:
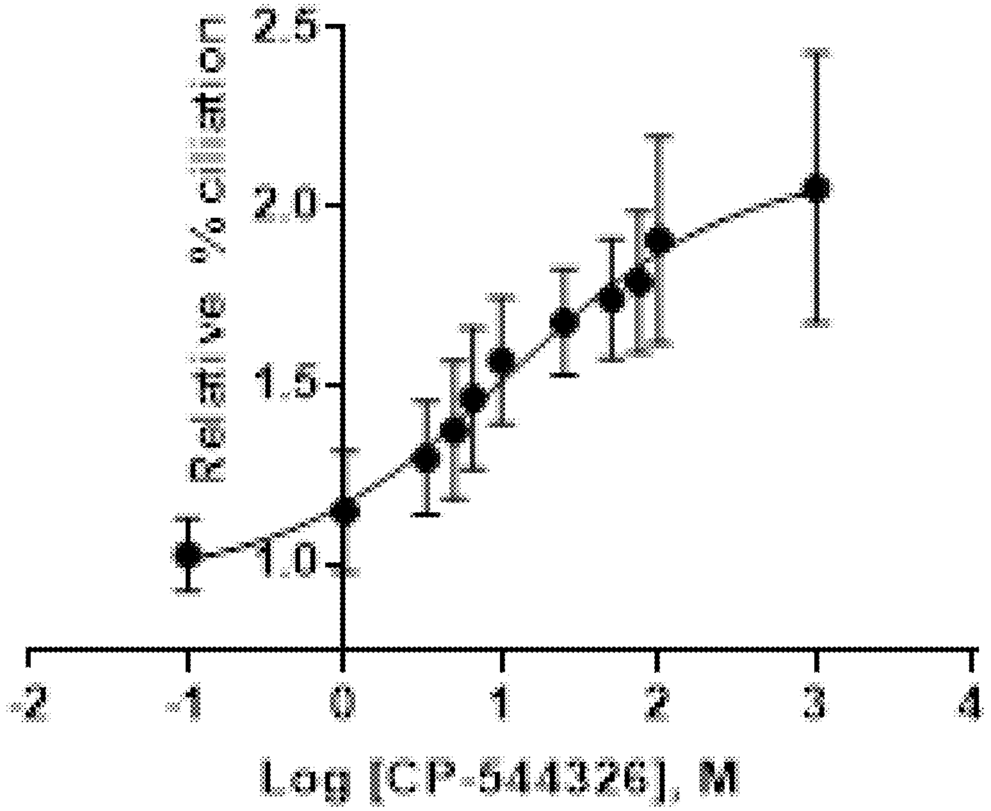
FIG. 16C shows the corresponding semi-log representation.
Figure 17A:
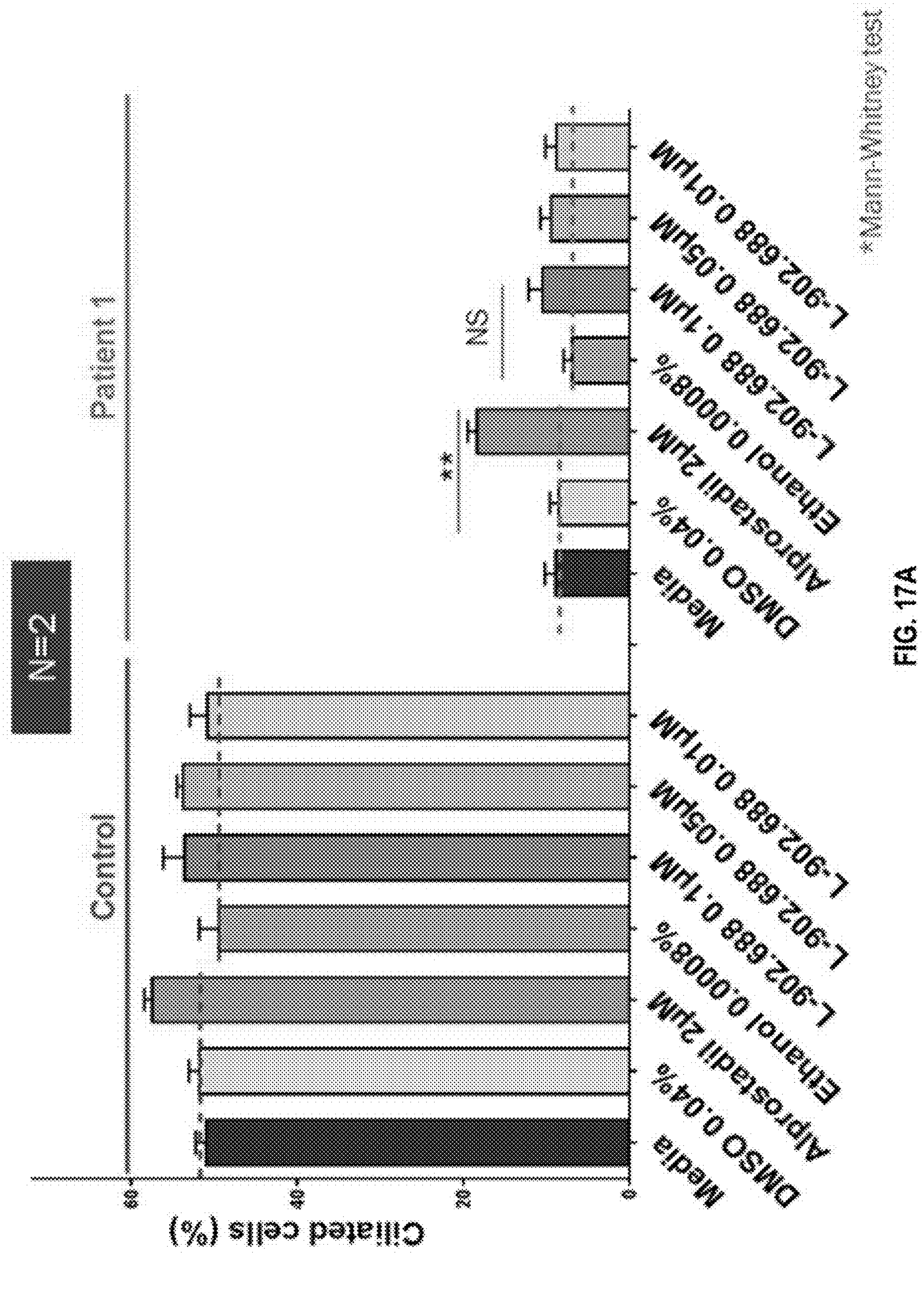
FIG. 17A shows the effect of L-902.688 on ciliogenesis.
Figure 17B:
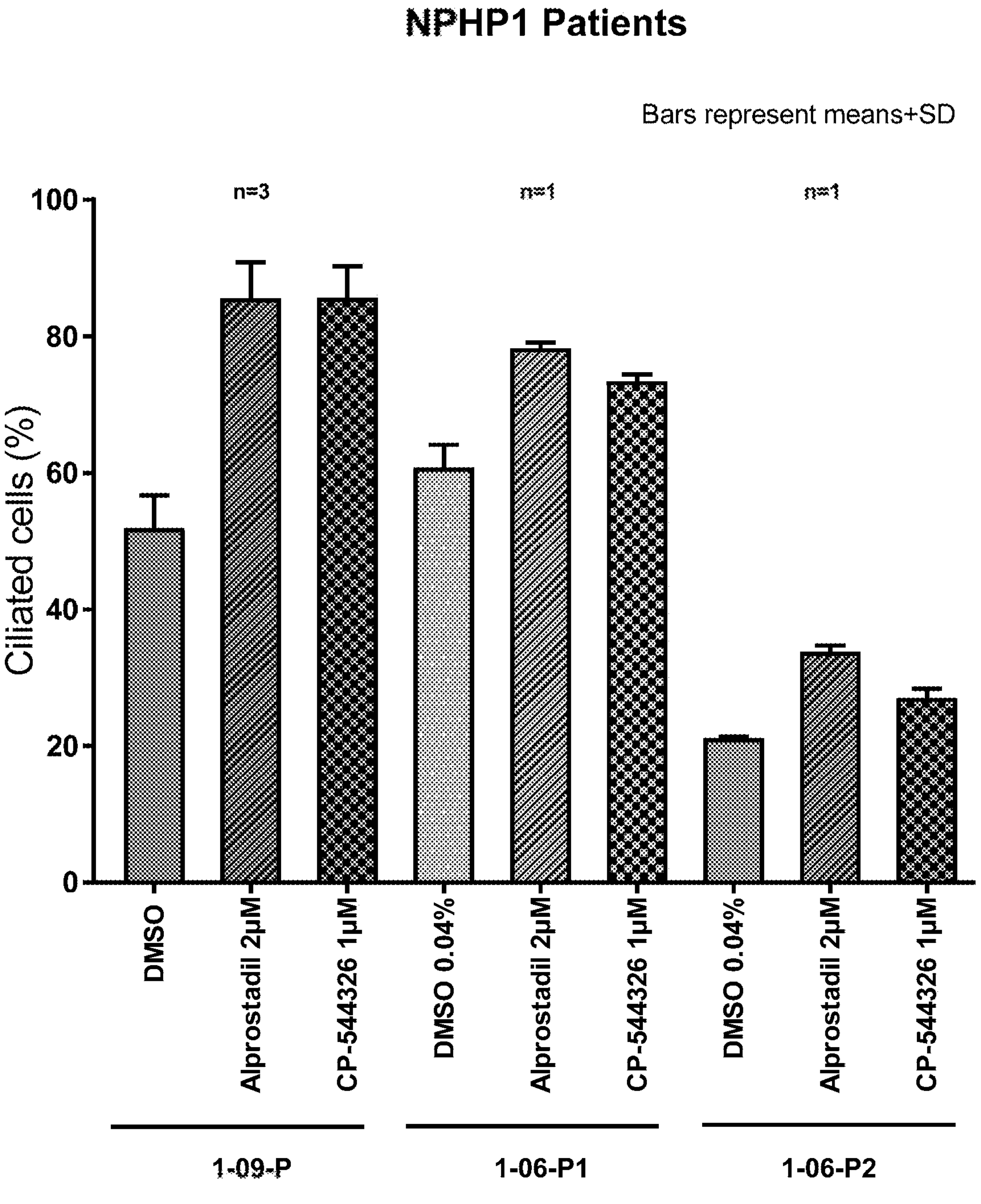
FIG. 17B shows the effect of CP-544326 and alprostadil on ciliogenesis.

FIG. 16B shows that CP-544326 restores ciliogenesis in a dose-dependent manner, compared to DMSO. FIG. 16C is a semi-log representation of the results of FIG. 16B, where CP-544326 titration indicates $EC_{50}$=11 nM for EP2. Restoration of ciliogenesis for non-prostanoid CP-544326 confirms its specificity in mechanism of action. In contrast, FIG. 17A shows that L-902.688, a prostanoid EP4 agonist, does not significantly affect ciliogenesis. These results indicate that EP2 plays a more important role in ciliogenesis than EP4.

Figure 17C:
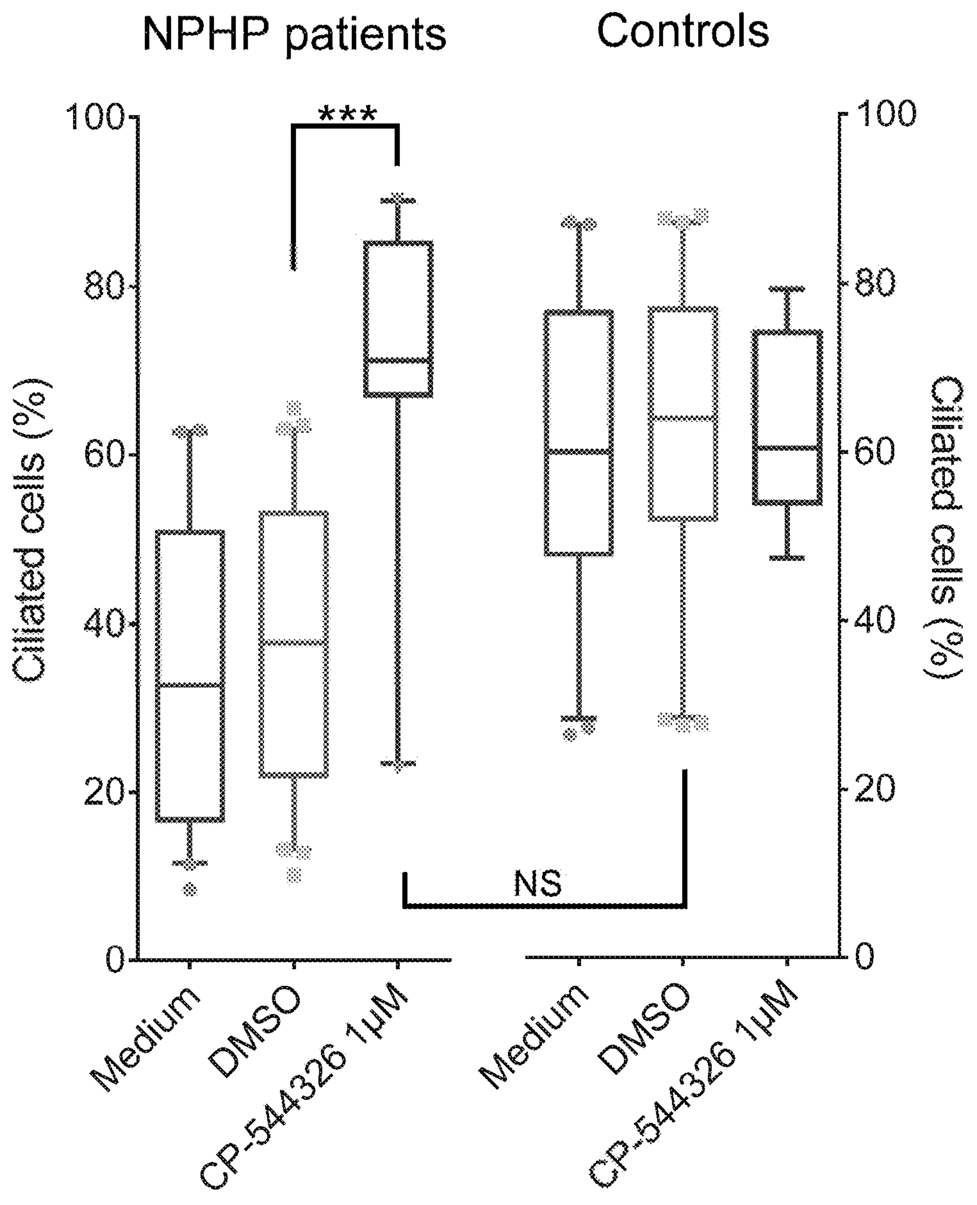
FIG. 17C shows the effects of CP-544326 on patient-derived cells.
Figure 17D:
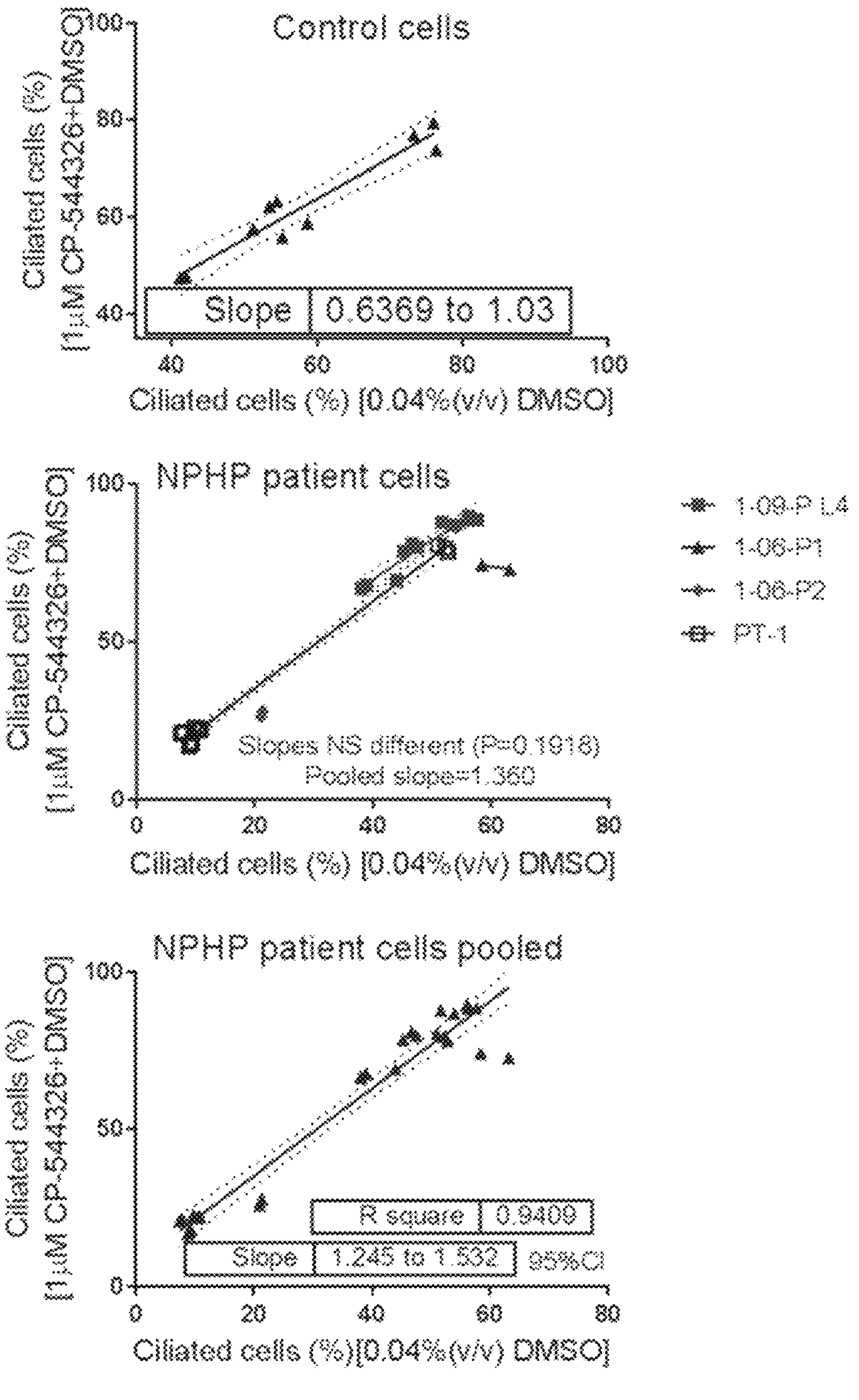
FIG. 17D shows cilio meta-analysis.

FIG. 17C shows, similar to Alprostadil, CP-544326 treatment increases ciliogenesis in multiple cell lines, e.g., 1-09-P, 1-06-P1 and 1-06-P2, derived from NPHP1(del) patients, as compared with that treated with DMSO. Meta-analysis in FIG. 17D shows linear regression analysis of FIG. 17D, where the slope reflects the effect of CP-544326 on ciliogenesis of control cells and multiple NPHP patient-derived cell lines, each symbol representing an independent experiment and each color representing a patient cell line (named as 1-09-P L4, 1-06-P1, 1-06-P2, PT-1). Linear regression for control normal epithelial cells data shows a slope value between 0.6369 and 1.03 suggesting that CP-544326 does not affect ciliogenesis. In contrast, linear regression for multiple NPHP patient-derived cells shows a pooled slope value of 1.36 or a range of slope values of 1.245 to 1.532 indicating a stimulating effect of alprostadil on ciliogenesis.

Differential Display Analysis

Microarray analysis was performed to identify expressed genes responsible for the alprostadil-mediated restoration of ciliogenesis. URECs were cultured in 96-well plates and treated with different concentrations of alprostadil, followed by RNA extraction using RLT or Qiazol method, as summarized in FIG. 18.

Figure 19:
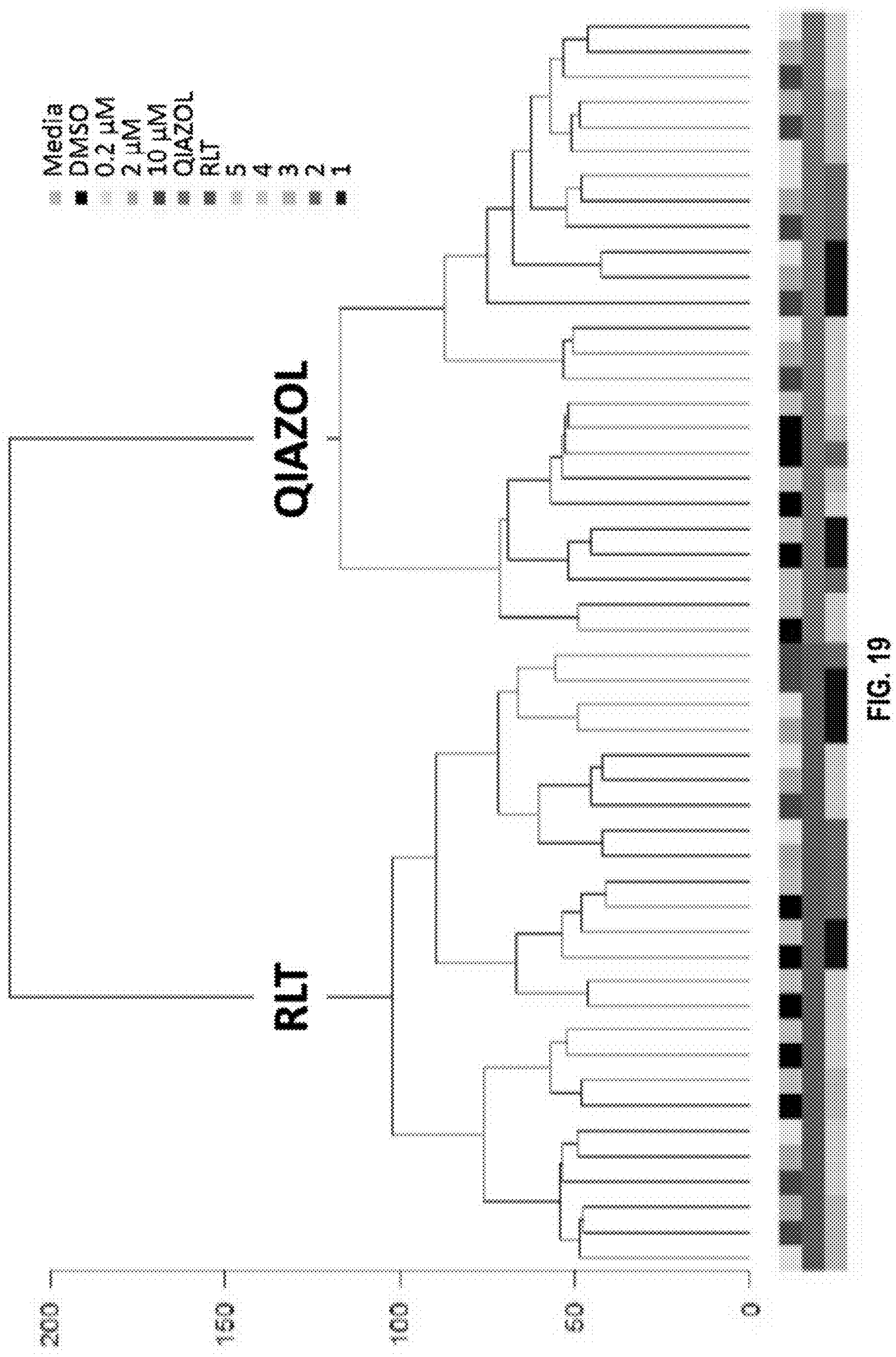
FIG. 19 shows microarray data of samples analyzed by hierarchical clustering.

FIG. 19 shows microarray data of samples analyzed by hierarchical clustering. Data were first clustered by extraction type (Qiazol vs. RLT). Qiazol samples were then clustered by condition, e.g., control versus alprostadil treatment, and RLT samples were then clustered by replicate.

Figure 20:
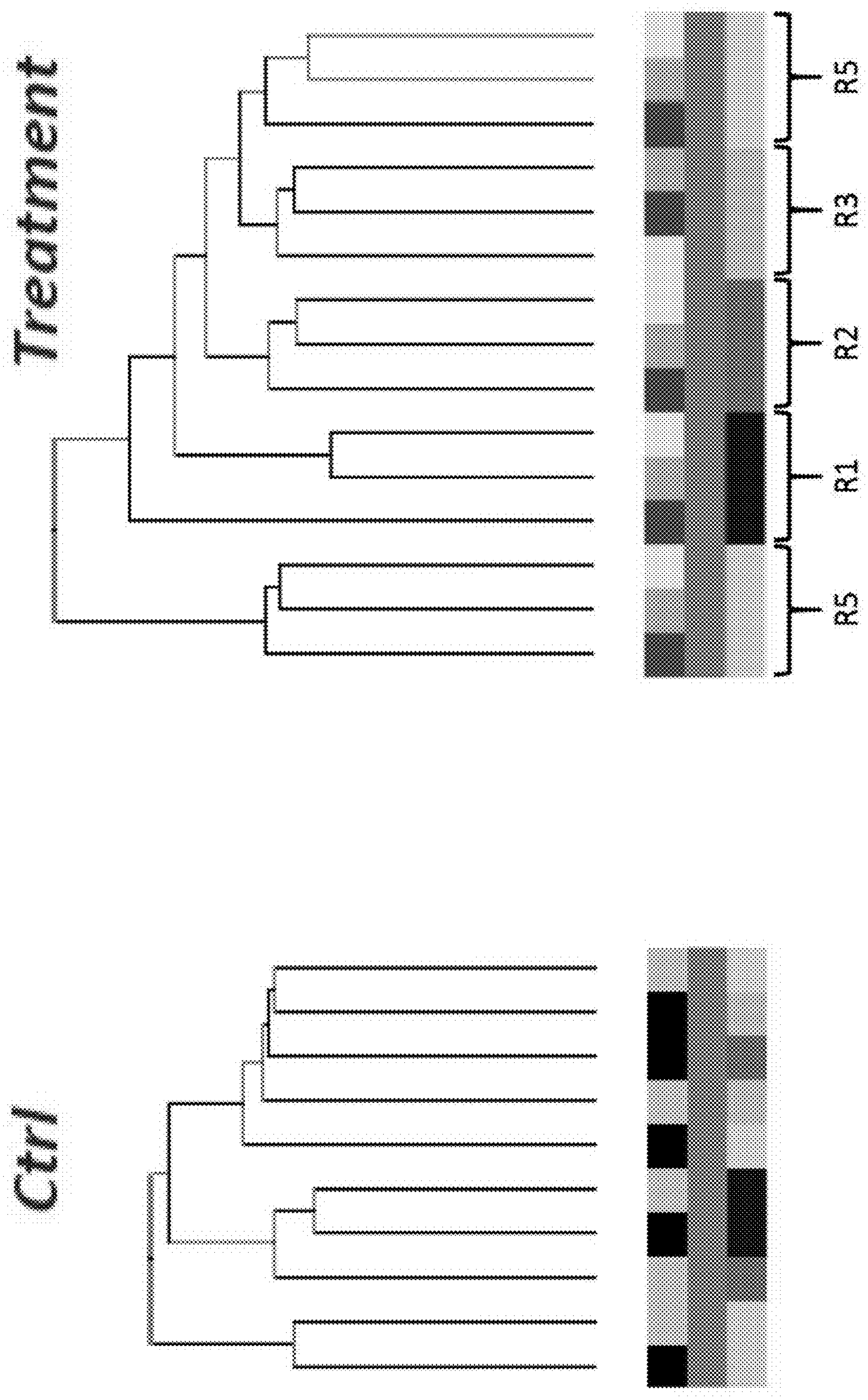
FIG. 20 shows microarray data of samples analyzed by hierarchical clustering.

FIG. 20 shows microarray data of samples analyzed by hierarchical clustering. Data obtained from Qiazol extraction samples were clustered by condition then by replicates, not by doses within treatment or media/DMSO within control.

Figure 21:
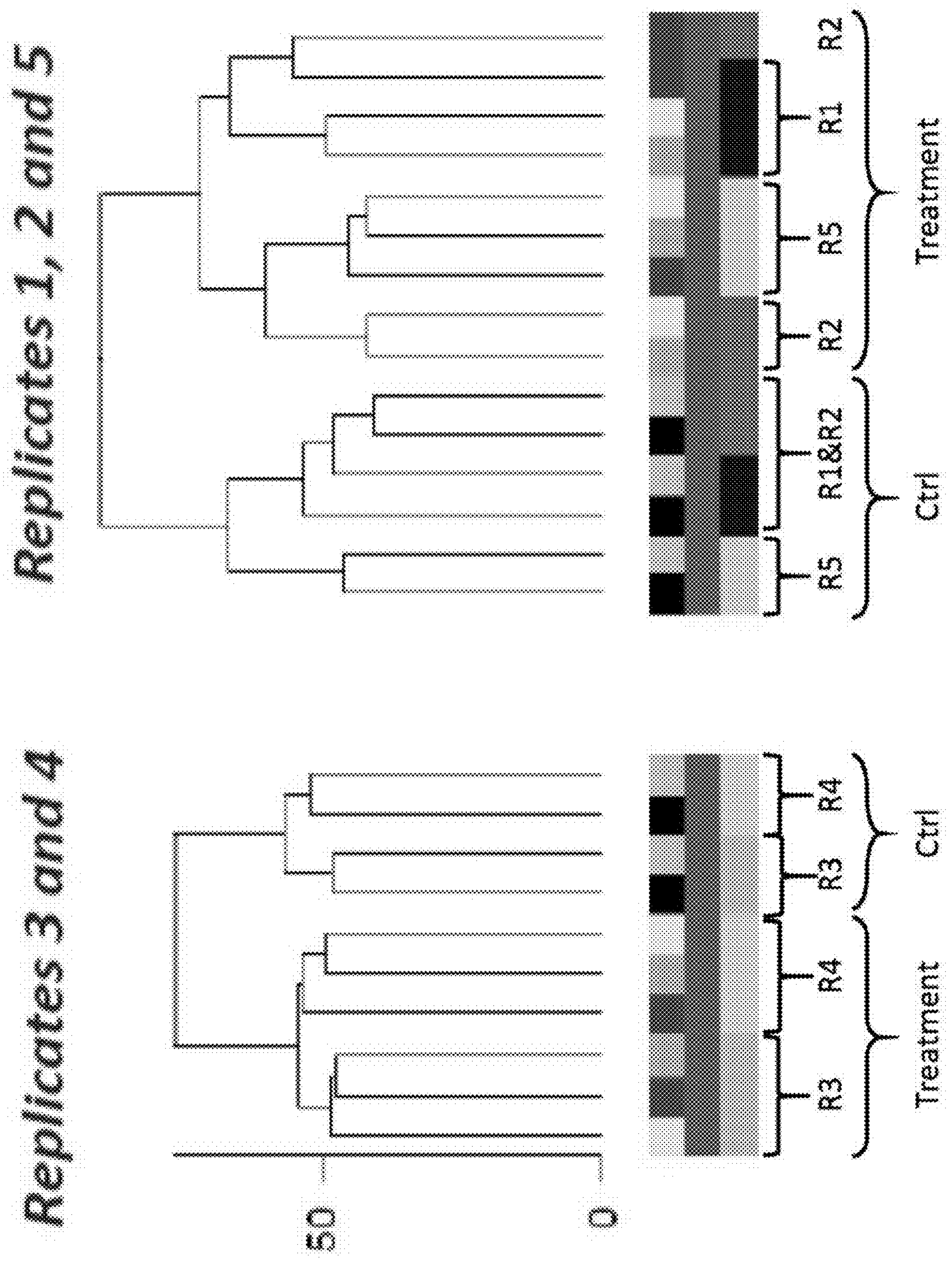
FIG. 21 shows microarray data of samples analyzed by hierarchical clustering.

FIG. 21 shows microarray data of samples analyzed by hierarchical clustering. Data obtained from RLT extraction samples were clustered by replicates then by condition (control vs. alprostadil treatment), not by doses within treatment or media/DMSO within control.

For microarray data obtained from RLT extraction samples, there was no significant difference between DMSO and media, e.g., only four differentially expressed genes without regulated exons/patterns. FIG. 22 shows, however, comparing control (DMSO) vs alprostadil treatment (0.2 μM, 2 μM and 10 μM), almost the same number of expressed and regulated genes across the three alprostadil concentration comparisons. The top three regulated genes are also almost the same and share same signaling pathway, e.g., down-regulation of cell adhesion and extracellular matrix.

Figure 26:
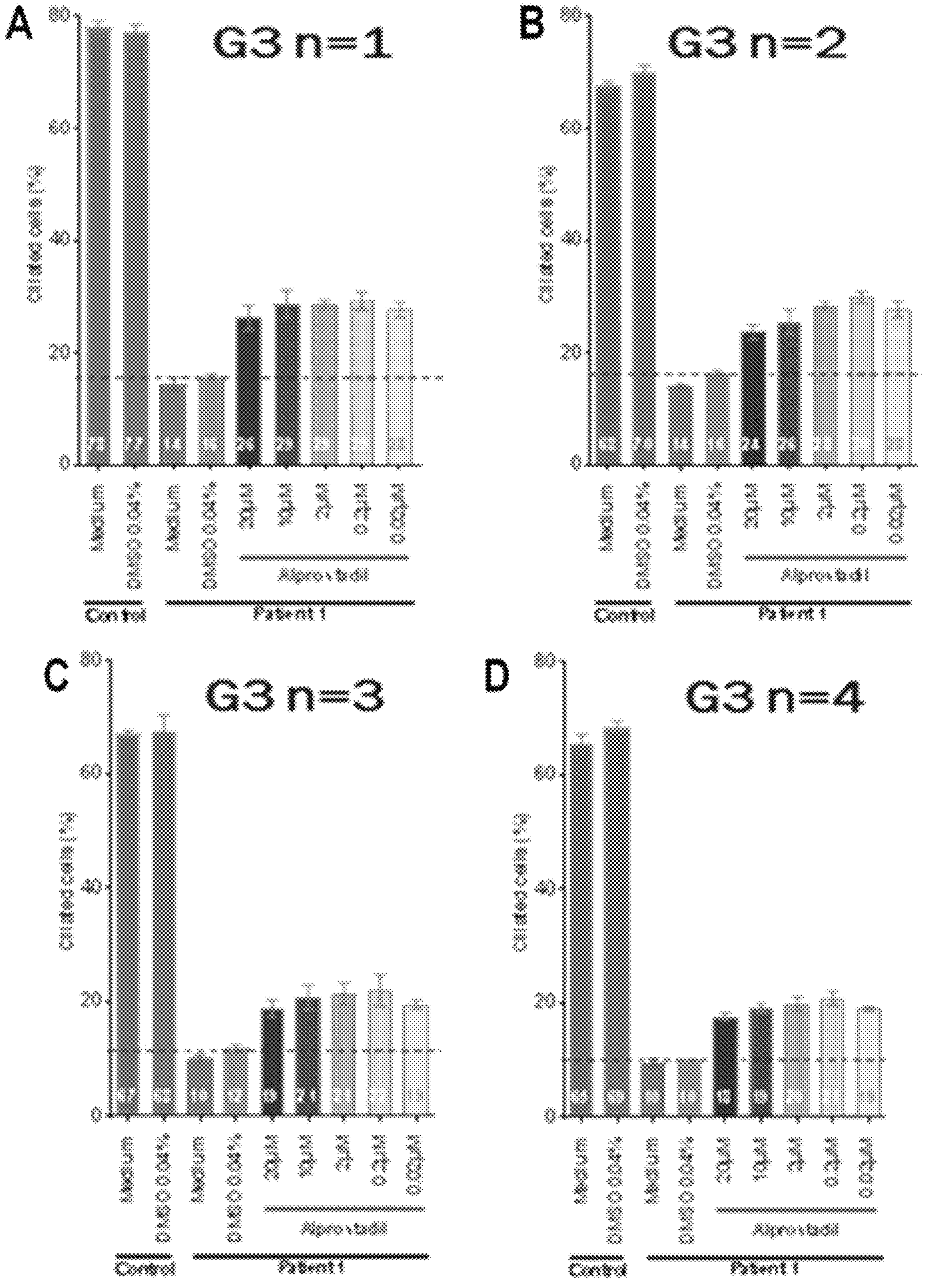
FIG. 26 shows (A-E) phenotypic analysis on the effect of alprostadil on ciliogenesis.
Figure 26:
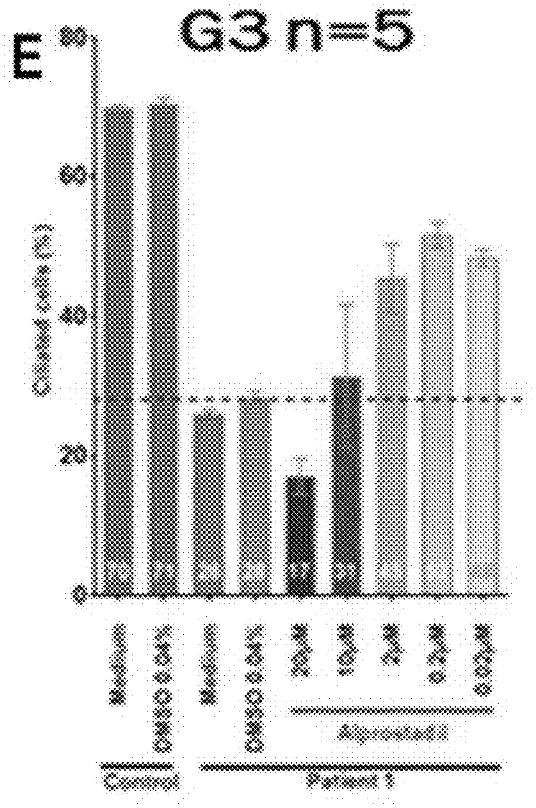

For microarray data obtained from Qiazol extraction samples, there was no significant difference between DMSO and media, e.g., 33 differentially expressed genes without regulated exons/patterns. However, as shown in FIG. 26, comparing control (DMSO) vs. alprostadil treatment (0.2 μM, 2 μM and 10 μM), there were almost the same number of expressed and regulated genes across the three alprostadil concentration comparisons. The top three regulated genes are also almost the same and share same signaling pathway, e.g., down-regulation of cell adhesion and extracellular matrix, and up-regulation of interferon signaling.

Figure 24A:
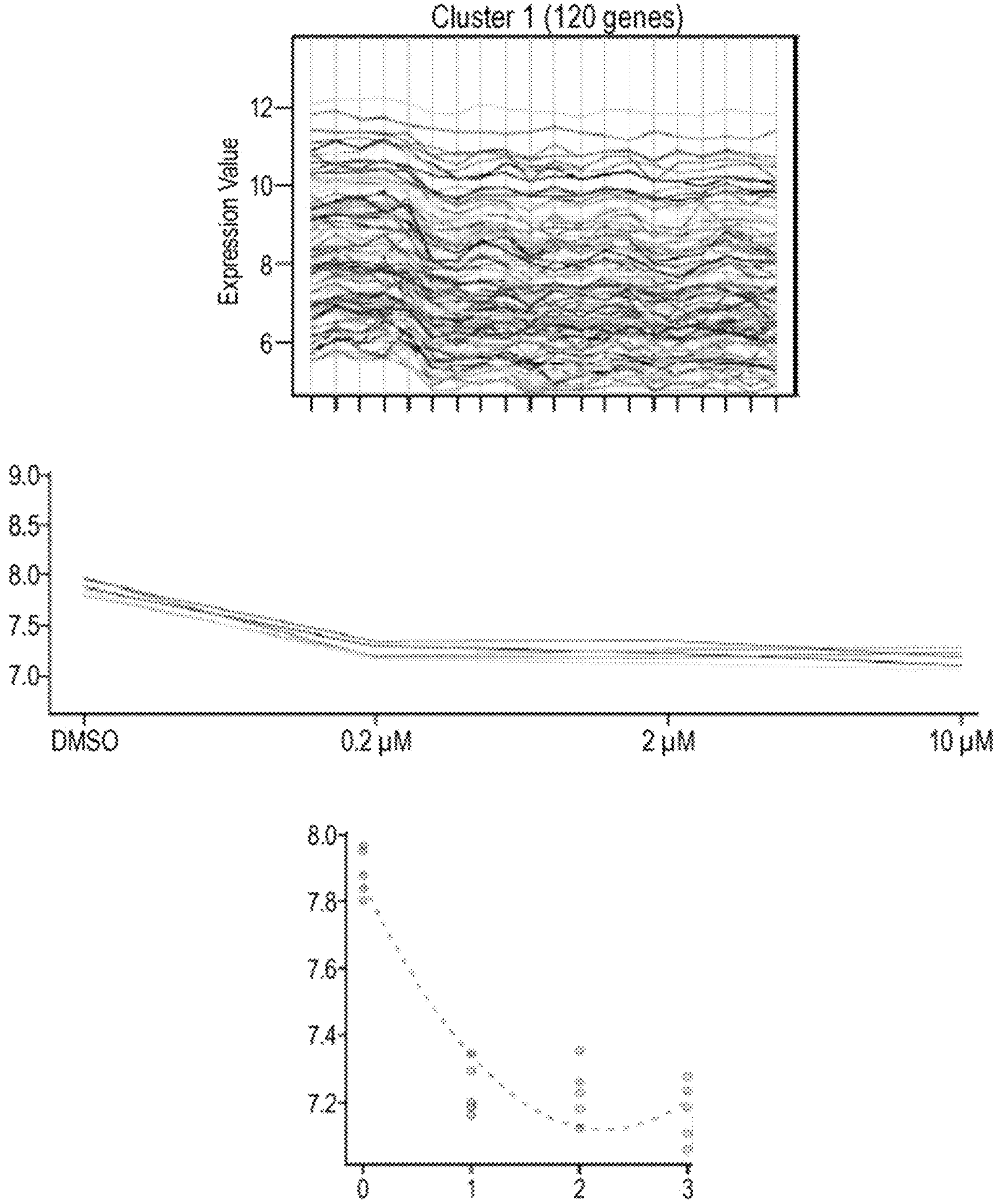

In addition, FIGS. 24A and 24B show two clusters were defined gathering a total of 310 genes, i.e., "cluster 1"=120 down-regulated genes and "cluster 2"=190 up-regulated genes. This indicates that no significant difference between microarray data obtained from various doses was detected.

Further, pathway analysis by crossing microarray data of patient with or without alprostadil treatment and with that of RNAseq of control vs patient revealed that alprostadil could reverse alteration in gene expression observed in NPHP patient-derived cells compared to control cells.

Multi-Omics Analysis

Figure 25:
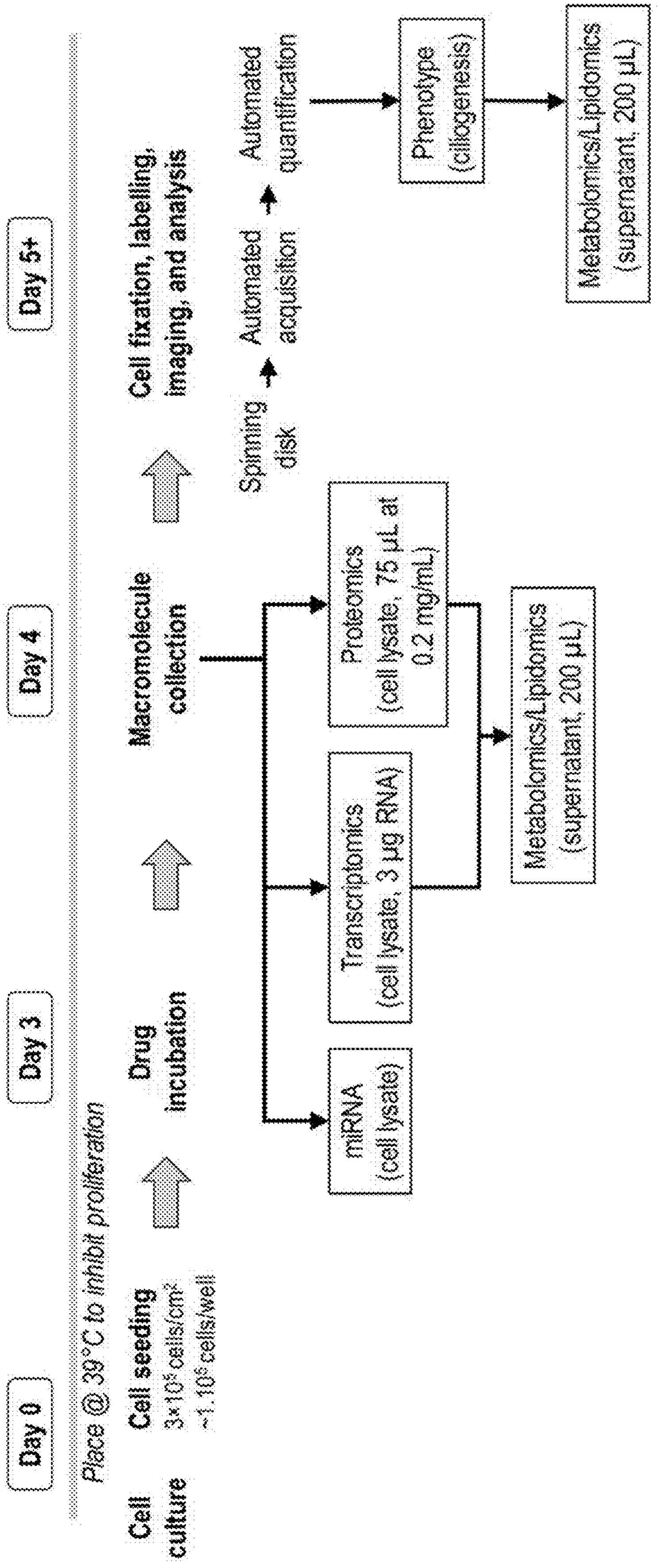
FIG. 25 shows a process of multi-omics analysis of drug effect on ciliogenesis.

FIG. 25 shows a process of multi-omics analysis of drug effect on ciliogenesis. FIGS. 26A-26E show, for example, phenotypic analysis on the effect of alprostadil on ciliogenesis, e.g., % ciliated cells, in five independent experiments. These results show that alprostadil partially restores ciliogenesis in n=1-5, with similar fold ratio without dose-dependent response.

FIG. 27 shows the summary of drugged and druggable genes identified from protein differential expression analysis of multi-omics data (NPHP patient-derived cells in DMSO 0.04% versus NPHP patient-derived cells treated with Alprostadil 2 μM), from which drugged genes are named.

Figure 28A:
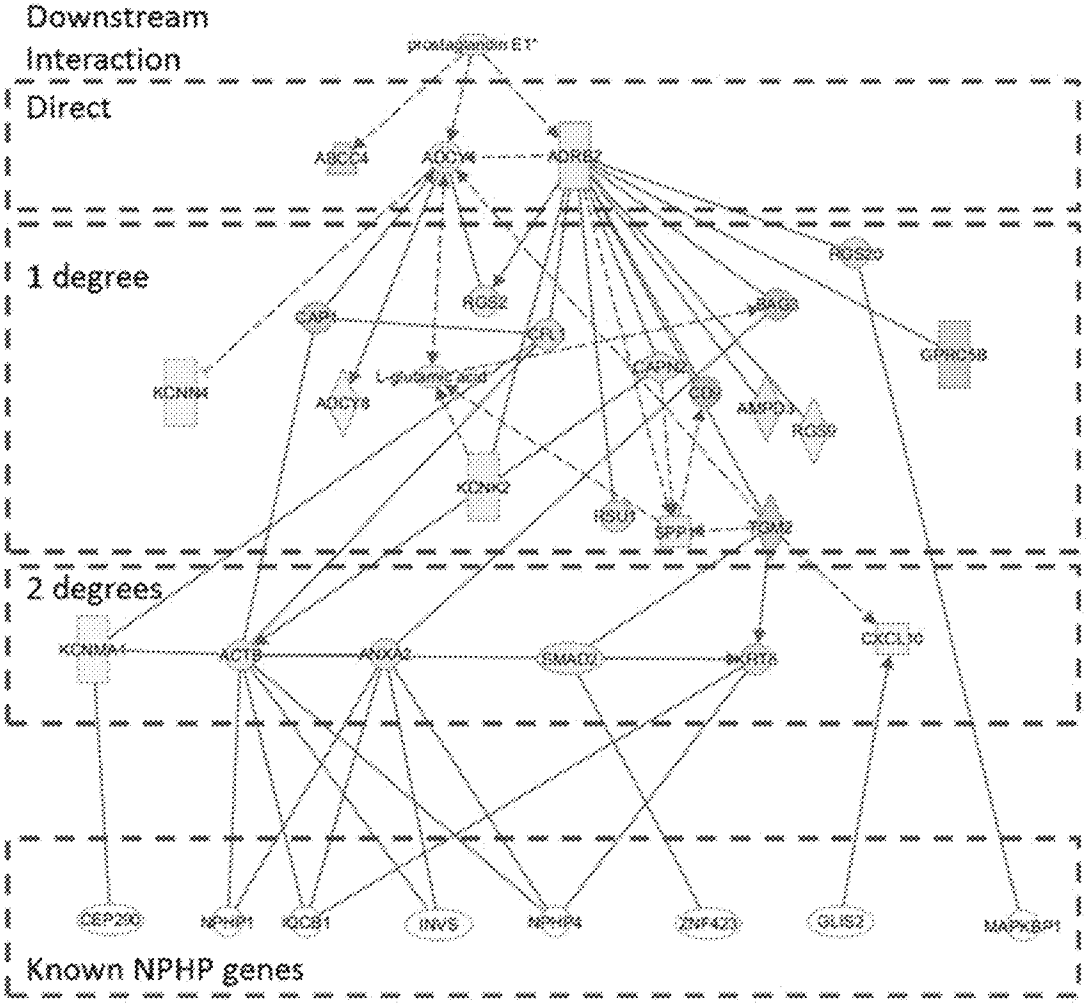
FIGS. 28A-C show pathways analysis from multi-omics data, and associated target opportunities for (A) prostaglandin E1 (alprostadil) downstream interactions, (B) NPHP1 upstream interactions and (C) NPHP1-20 genes-associated direct interactions.
Figure 28B:
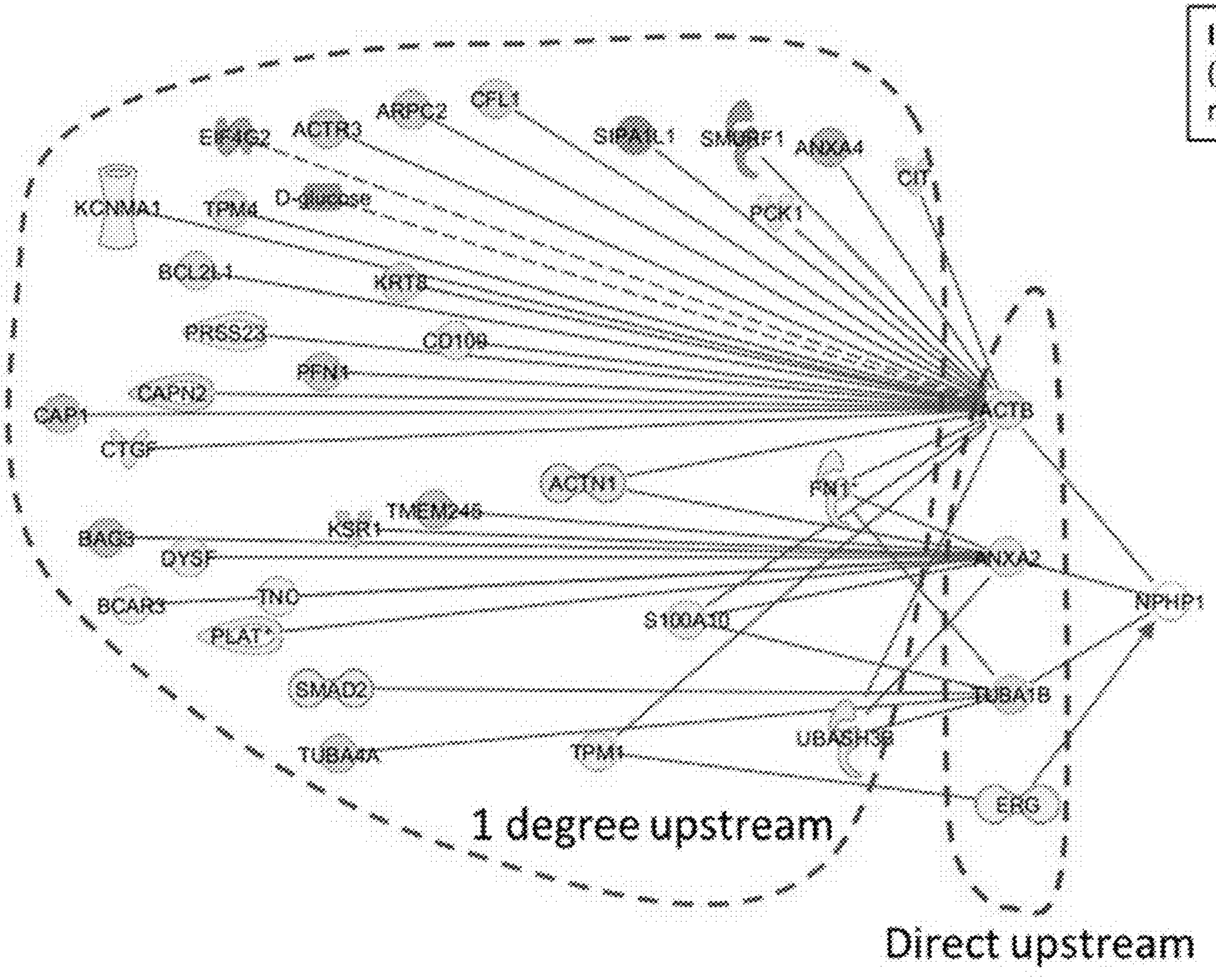
Figure 28C:
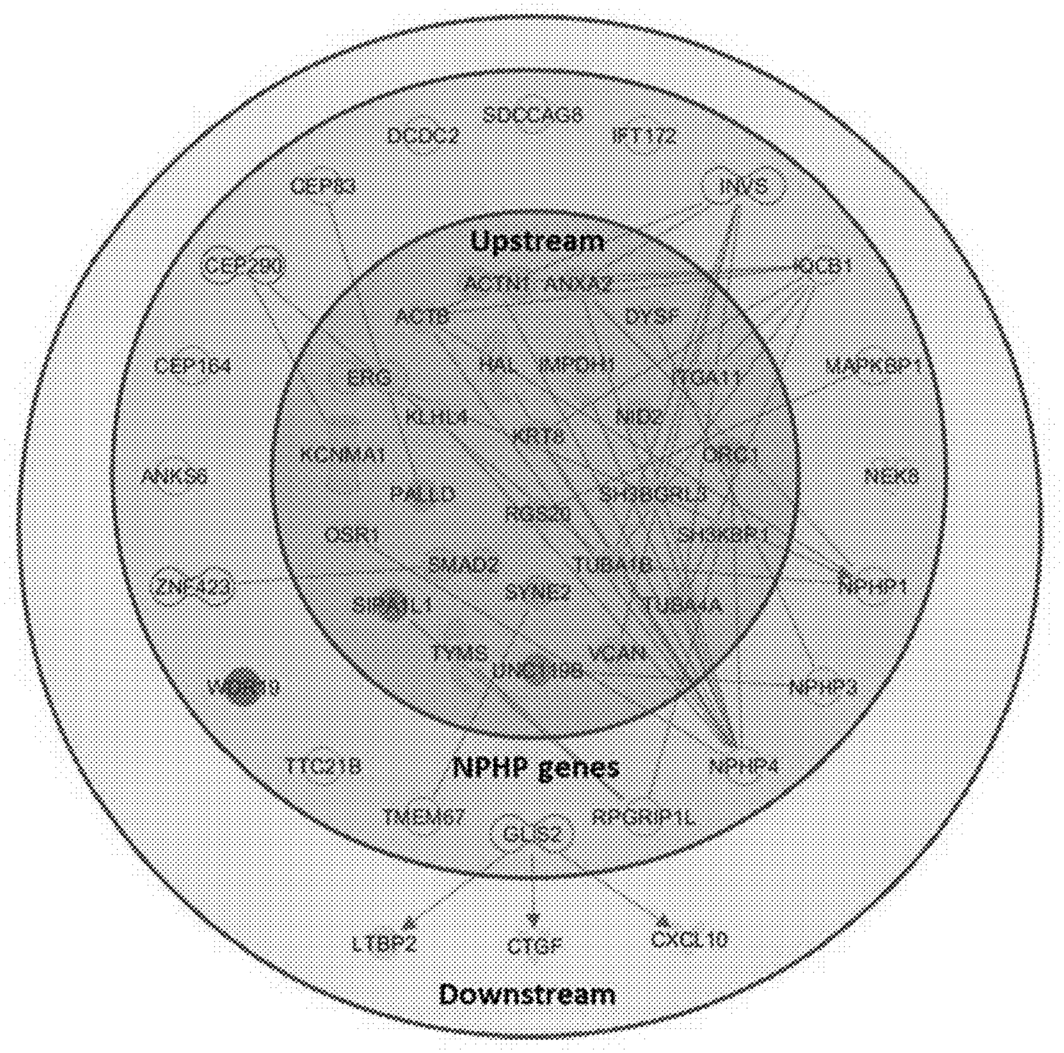

FIG. 28 (A-C) shows pathways analysis (using Ingenuity Pathway Analysis) from multi-omics data, and associated target opportunities for (A) prostaglandin E1 (alprostadil) downstream interactions, (B) NPHP1 upstream interactions and (C) NPHP1-20 genes-associated direct interactions.

In vivo model FIG. 29 shows results from a zebrafish NPHP4 morpholino (MO) model, in which wild-type zebrafish embryos at the one-cell stage were injected with morpholino (e.g., NPHP4 ATG MO), which blocks the start site of NPHP4 mRNA from ribosome binding. The morpholino specifically inhibits the translation of NPHP4 mRNA. Zebrafish NPHP4 MO exhibits classical ciliopathy-related phenotype including body curvature, pronephric cysts, laterality (heart looping) defects, and dilations of cloaca (obstruction).

Figure 30:
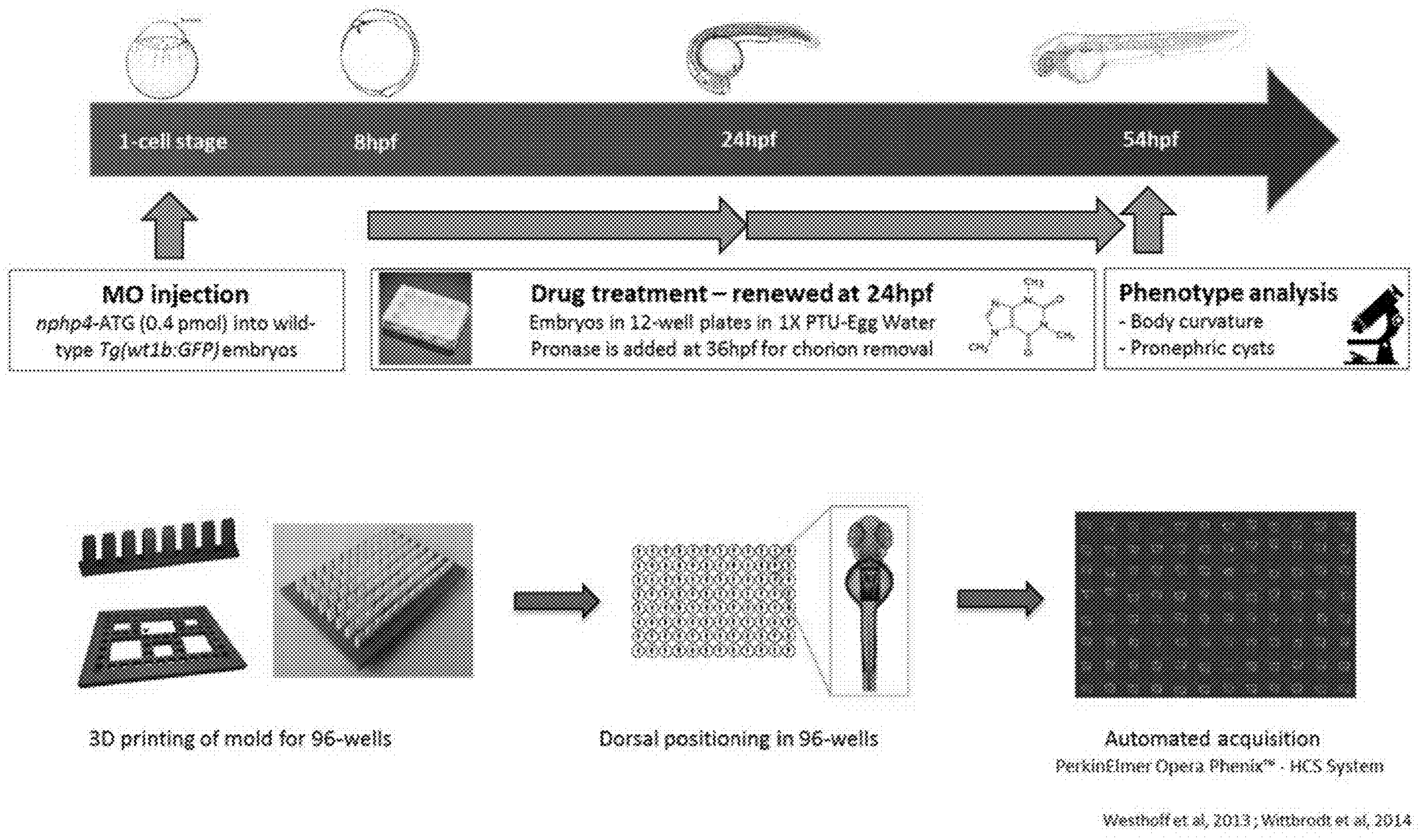
FIG. 30 shows protocols of drug treatment in zebrafish NPHP4 MO model.

FIG. 30 is a schematic showing protocols of drug treatment (alprostadil: 0.5 μM and 5 μM) in zebrafish NPHP4 MO model. Briefly, wild-type Tg(wt1b:GFP) transgenic zebrafish embryos were injected with morpholino (e.g., nphp4 ATG MO) at one-cell stage. At 8 hours post-fertilization (hpf), injected embryos were treated with drug or vehicle in PTU-egg water (1 mL in 12-well plates). At 24 hpf, drug treatment was renewed, and pronase was added at 36 hpf for chorion removal. At 54 hpf, zebrafish embryos were examined for phenotype, notably body curvature and pronephric cysts at glomeruli (labelled by Tg(wt1b:GFP) transgene), using suitable means, e.g., a stereoscope and PerkinElmer Opera Phenix HCS system, respectively.

FIG. 31, panel A shows that DMSO (0.04%) did not induce lethality, body curvature or pronephric cysts in wild-type zebrafish embryos. In addition, zebrafish injected with control morpholino, which does not affect NPHP4 expression, also did not exhibit body curvature (FIG. 31, panel B) or pronephric cysts (FIG. 31, panel C). In contrast, zebrafish injected with NPHP4 MO exhibit classical, ciliopathy-related phenotypes including, for example, body curvature (FIG. 31, panel B) and pronephric cysts (FIG. 31, panel C), in a dose-dependent manner.

Figure 32:
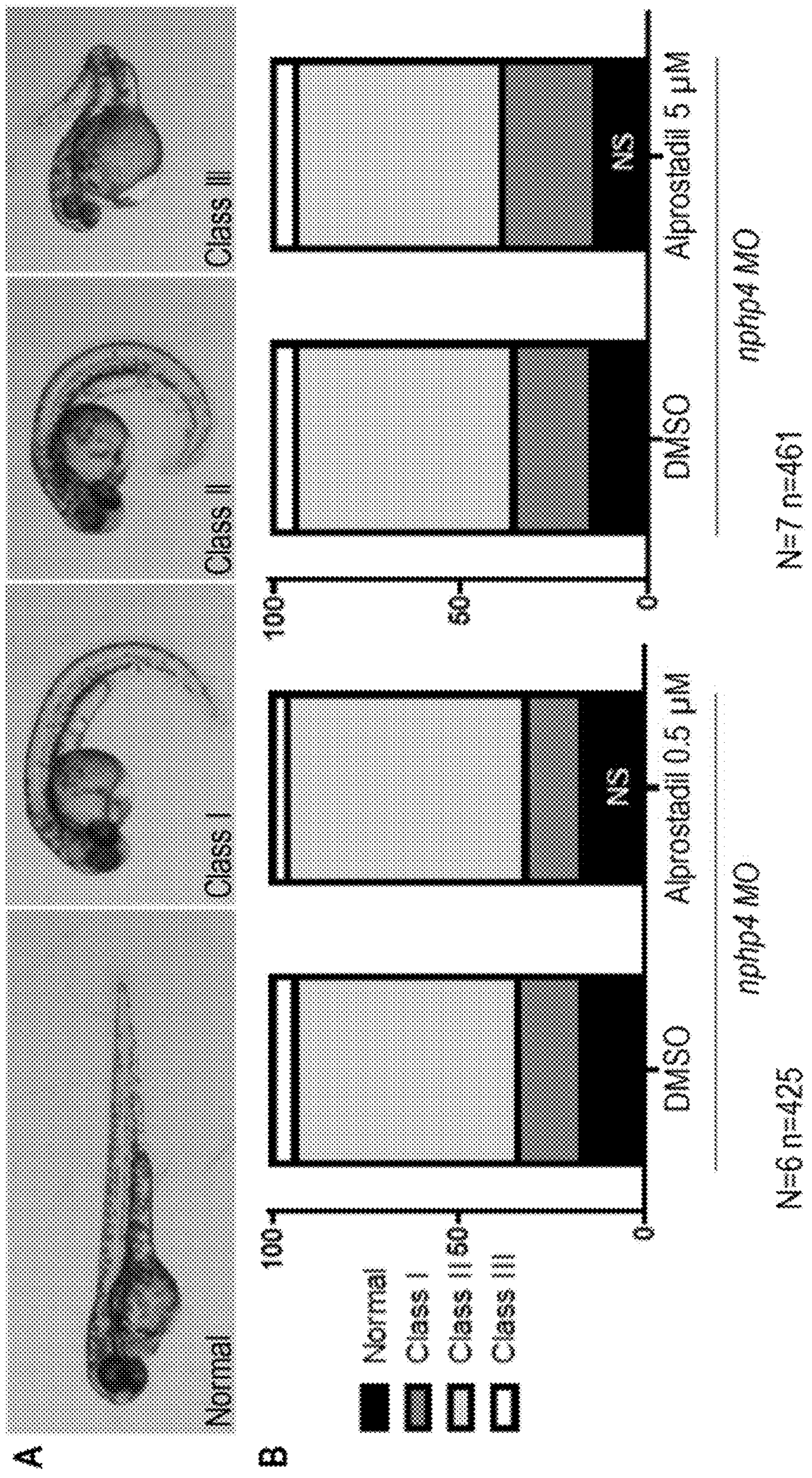
FIG. 32 shows (A) representative body axis curvatures of zebrafish; and (B, C) the effect of alprostadil on body axis curvatures of zebrafish.
Figure 32:
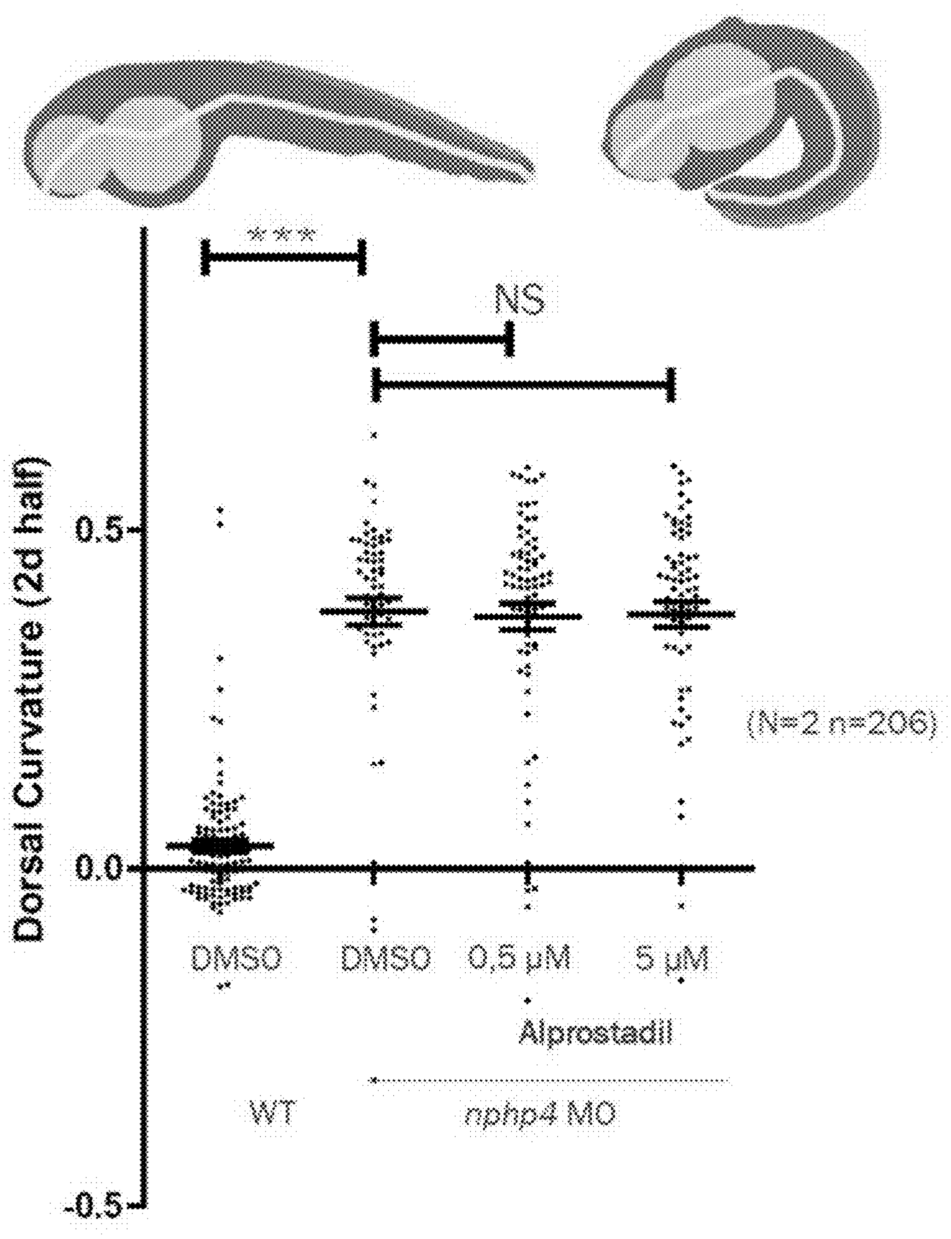
Figure 35:
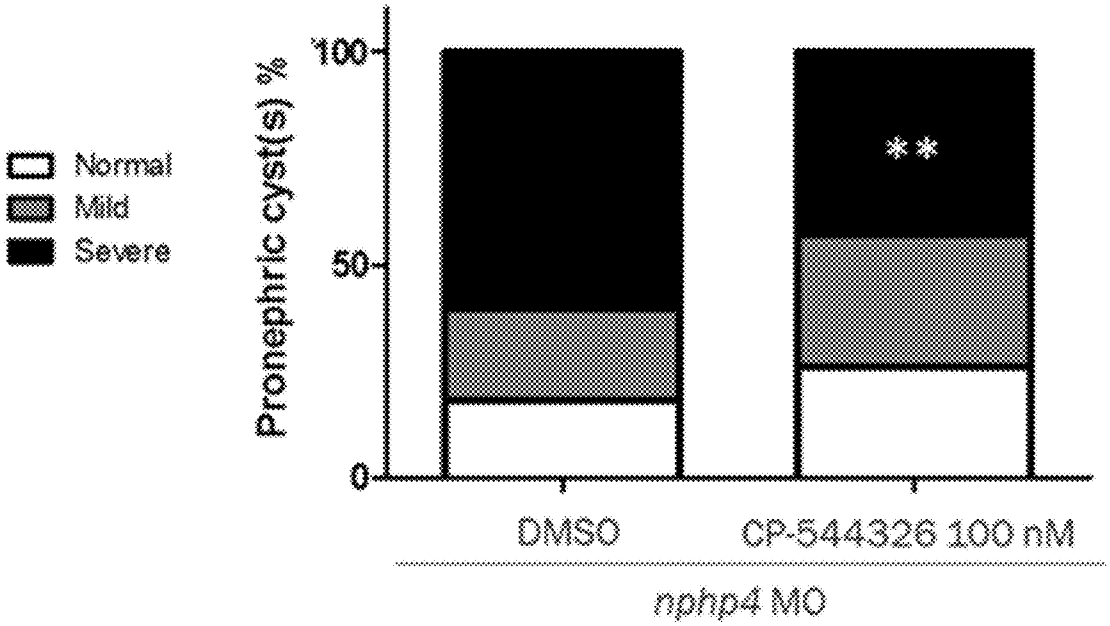
FIG. 35 shows the effect of CP-544326 on pronephric cysts of zebrafish.

FIG. 32, panel A shows representative body axis curvature of zebrafish in four categories: normal, class I, class II and class III. FIG. 35, panel B shows that alprostadil treatment (0.5 μM and 5 μM) did not significantly affect body axis curvature of zebrafish NPHP4 MO, compared to that of DMSO treatment ($p>0.05$, Fischer's exact test). Similarly, using body curvature as an automated quantified parameter, FIG. 32, panel C shows that alprostadil treatment (0.5 μM and 5 μM) did not significantly affect dorsal curvature of zebrafish NPHP4 MO, compared to that of DMSO treatment.

Figure 33:
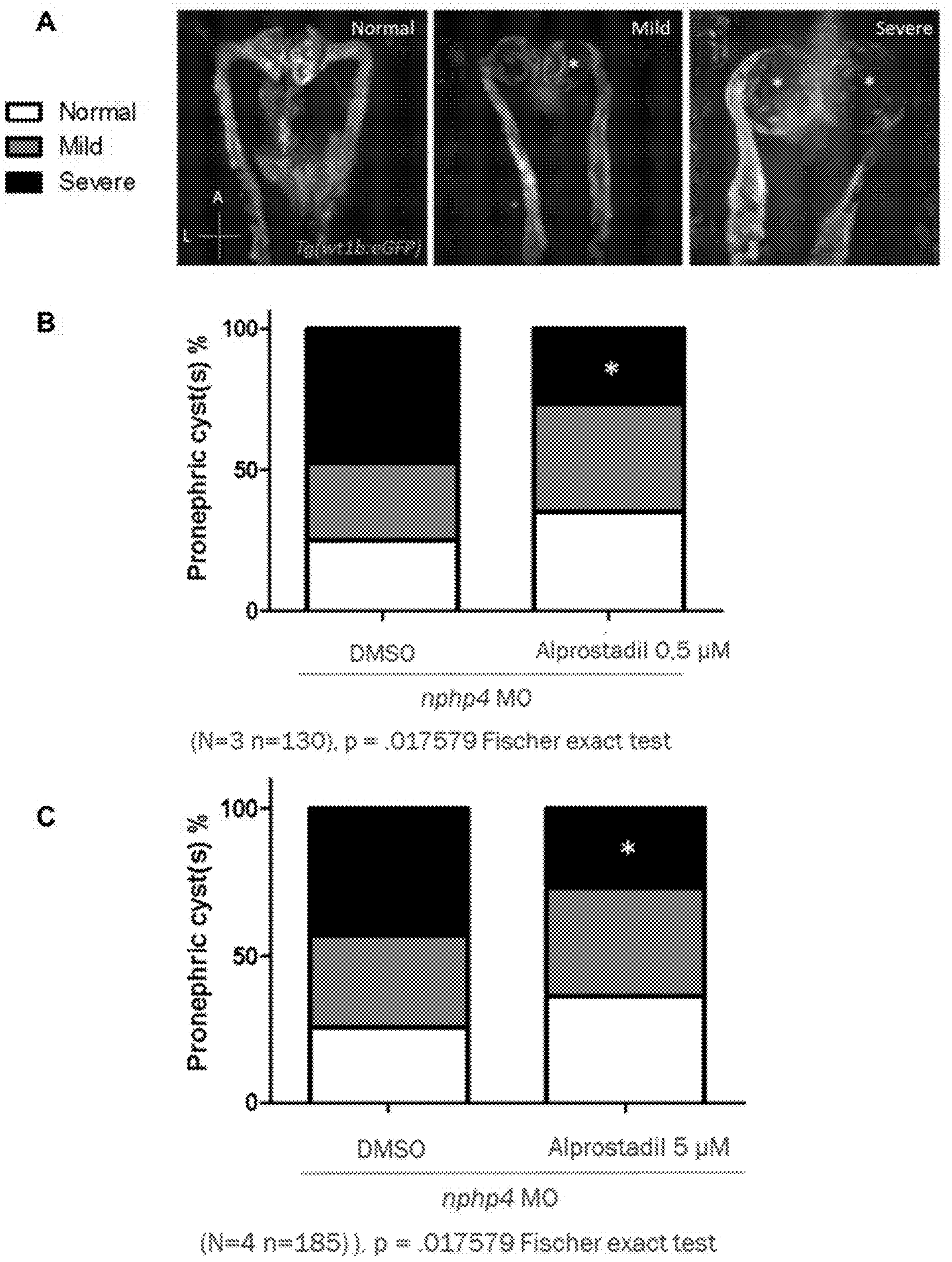
FIG. 33 shows (A) representative pronephric cysts of zebrafish; and (B, C) the effect of alprostadil on pronephric cysts of zebrafish.

FIG. 33, panel A shows representative pronephric cysts of zebrafish: normal, mild and severe. FIG. 33, panel B shows that alprostadil treatment (0.5 μM) significantly reduced the percentage of severe pronephric cysts of nphp4 MO-injected embryos, compared to that of DMSO treatment ($p<0.05$, Fischer's exact test). Similarly, FIG. 33, panel C shows that alprostadil treatment (5 μM) significantly reduced the percentage of severe pronephric cysts of nphp4 MO-injected embryos, compared to that of DMSO treatment.

Figure 34:
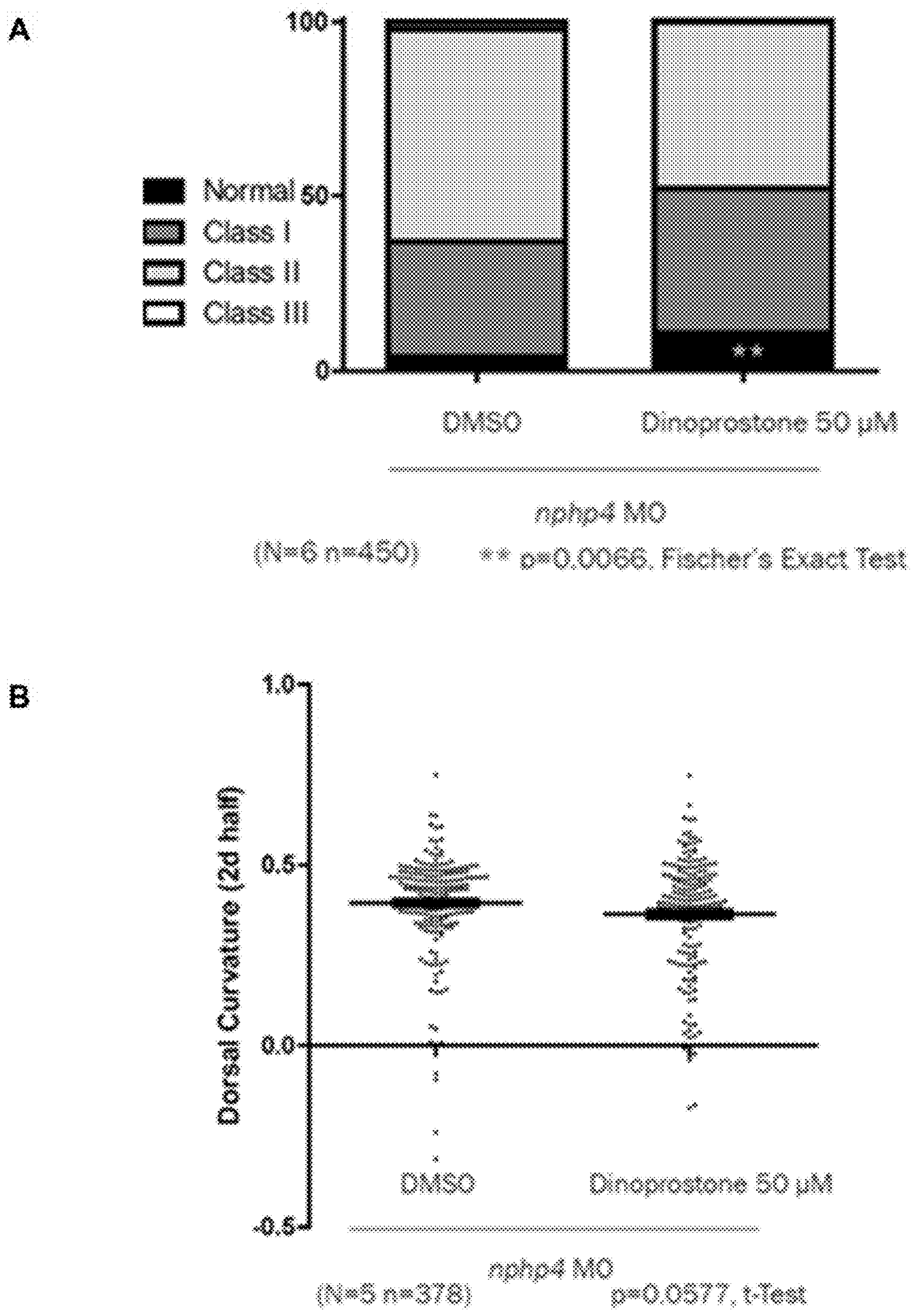
FIG. 34 shows (A, B) the effect of dinoprostone on body axis curvatures of zebrafish; and (C) the effect of dinoprostone on pronephric cysts of zebrafish.
Figure 34:
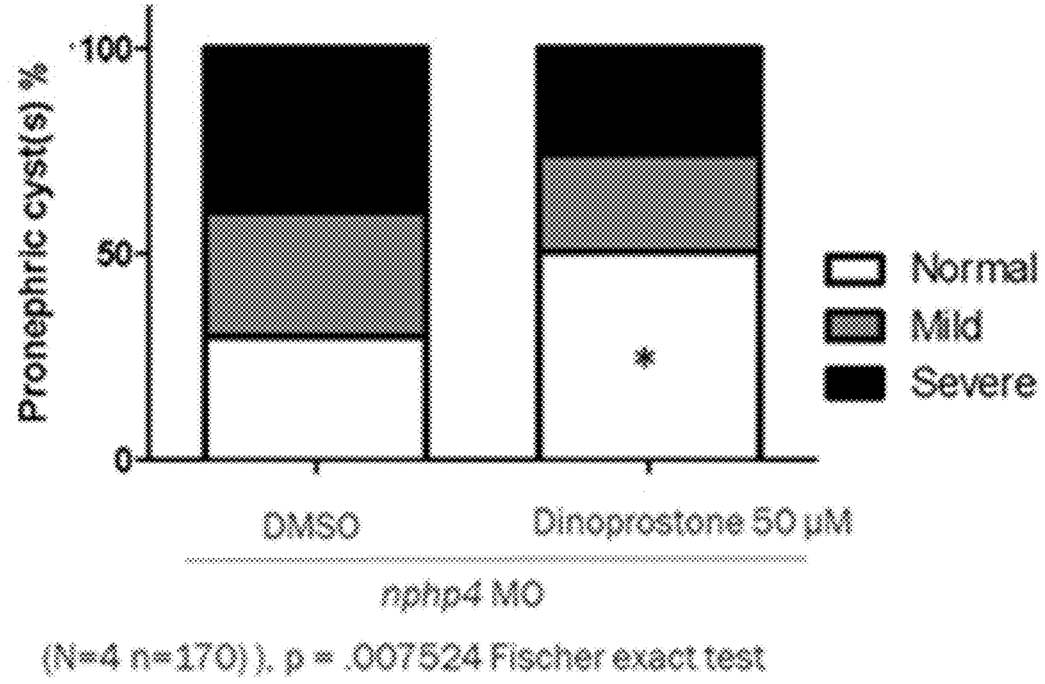

To test the effect of dinoprostone (PGE2) on ciliopathy, zebrafish NPHP4 MO were treated with dinoprostone (50 μM) or DMSO. FIG. 34, panel A shows that dinoprostone treatment significantly increases % normal body axis curvature of zebrafish NPHP4 MO, compared to that of DMSO treatment ($p=0.0066$, Fischer's exact test). FIG. 34, panel B shows, however, dinoprostone treatment did not significantly affect dorsal curvature of zebrafish NPHP4 MO, compared to that of DMSO treatment ($p=0.0577$, t-test). FIG. 34, panel C shows dinoprostone treatment significantly reduced % severe and mild pronephric cysts and increased % normal pronephric cysts of zebrafish NPHP4 MO, compared to that of DMSO treatment ($p<0.008$, Fischer's exact test).

To test the effect of the selective EP2 agonist, CP-544326, zebrafish NPHP4 MO were treated with CP-544326 (100 nM) or DMSO. FIG. 35 shows that CP-544326 treatment significantly reduces % severe pronephric cysts and increases % mild and normal pronephric cysts of zebrafish NPHP4 MO, as compared with that of DMSO treatment ($p<0.01$, Fischer's exact test).

Figure 37A:
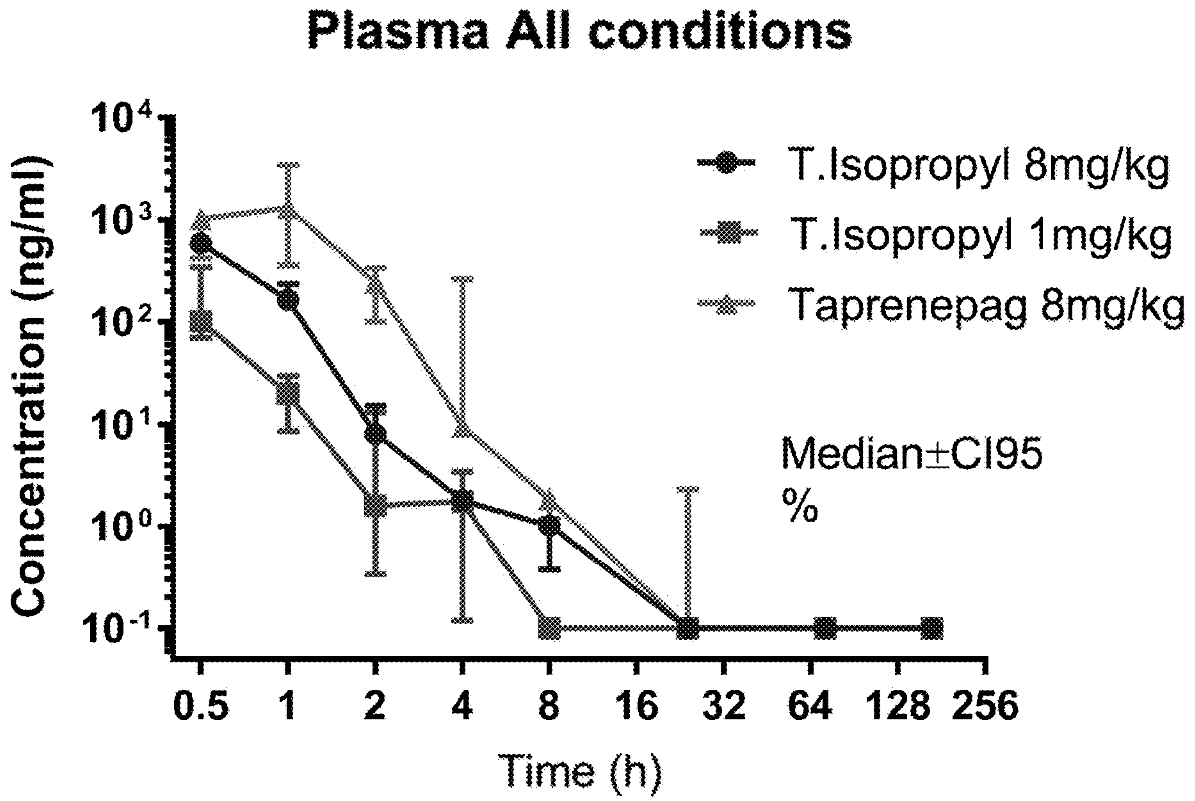
FIGS. 37A-37E show pharmacokinetics study results.
Figure 37B:
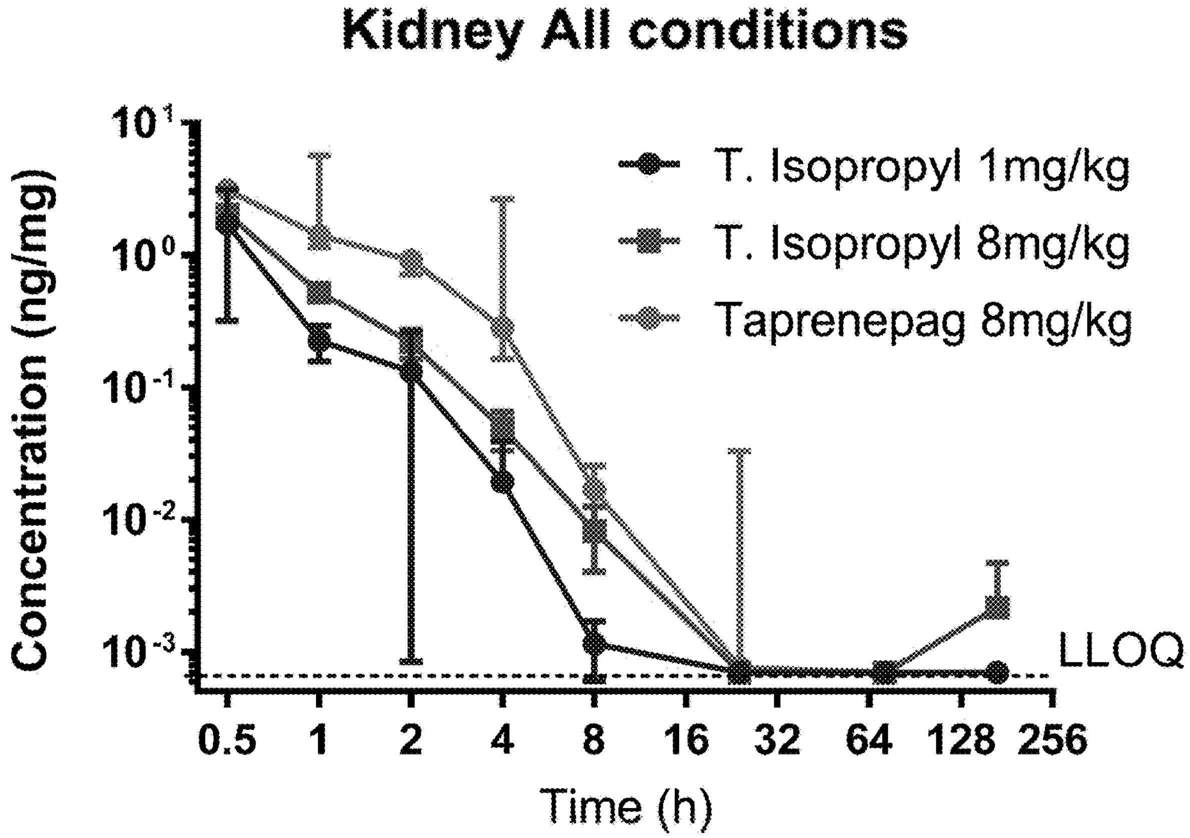
Figure 37C:
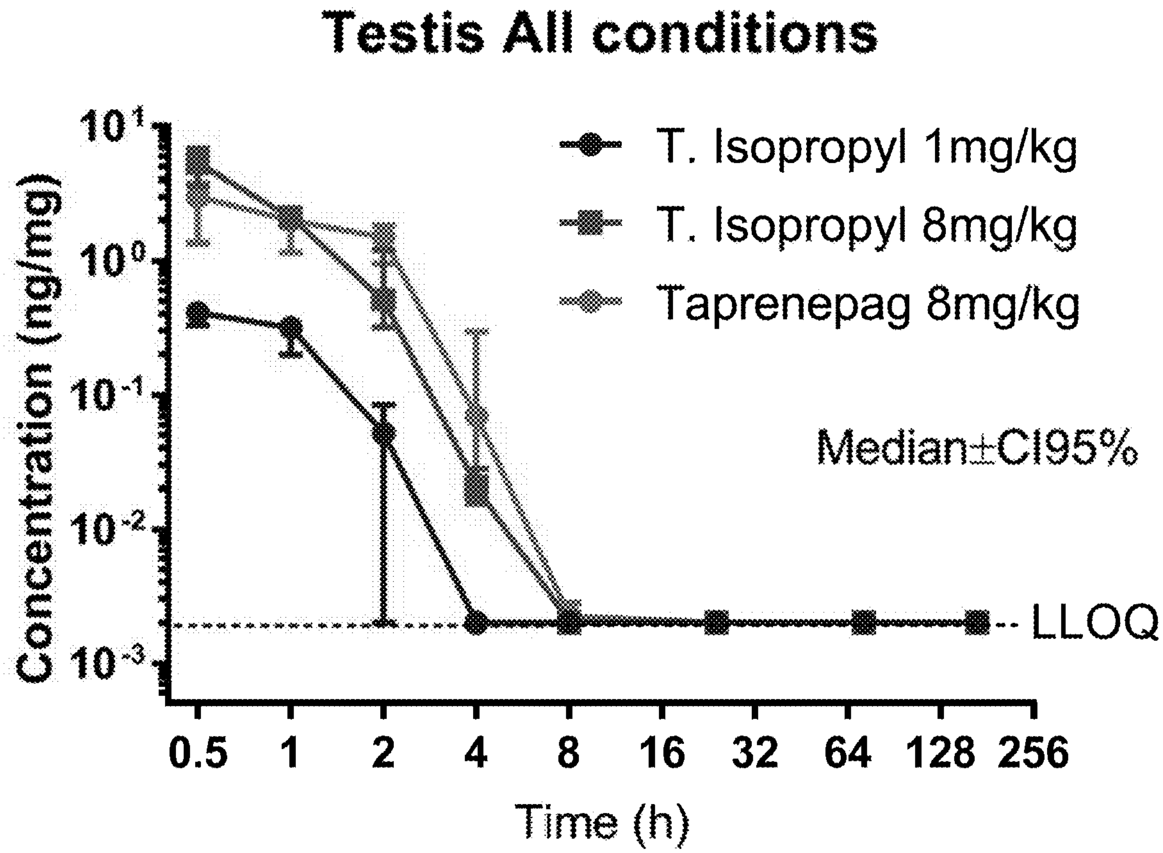
Figure 37D:
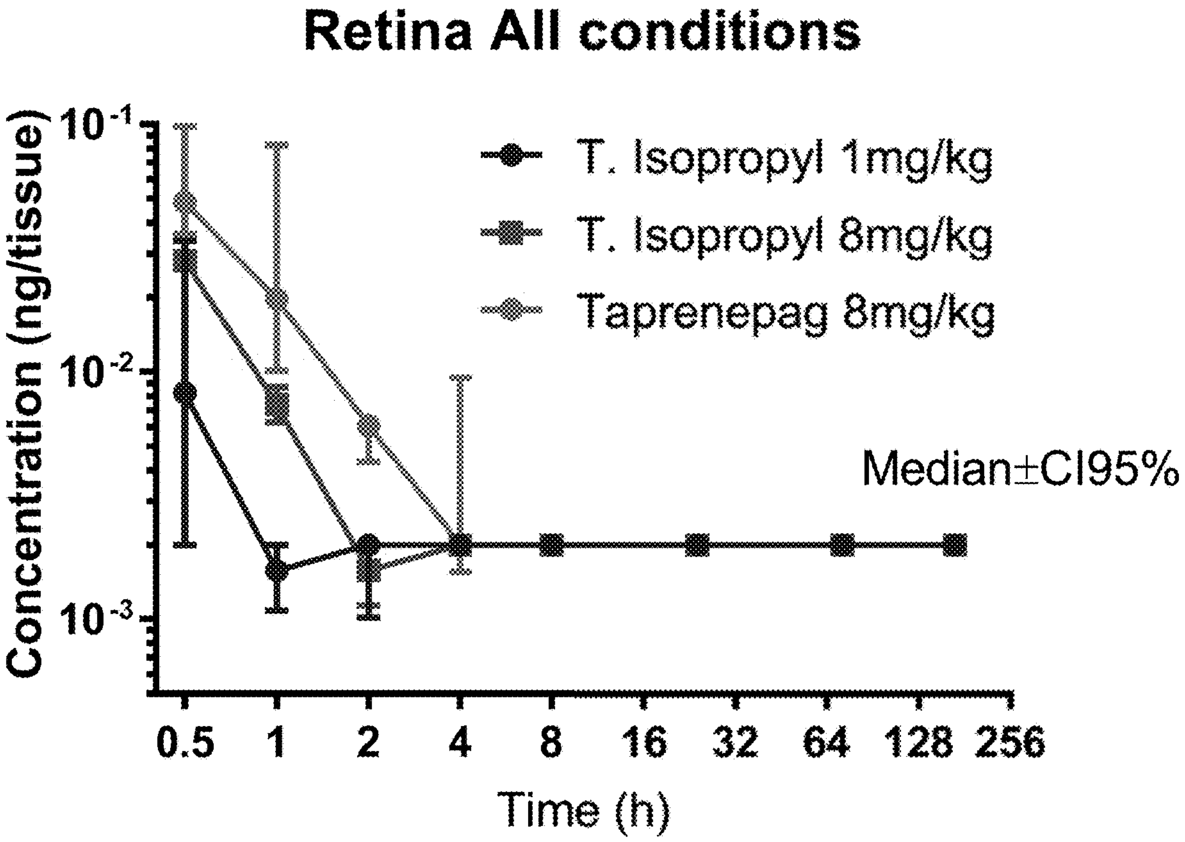
Figure 37E:
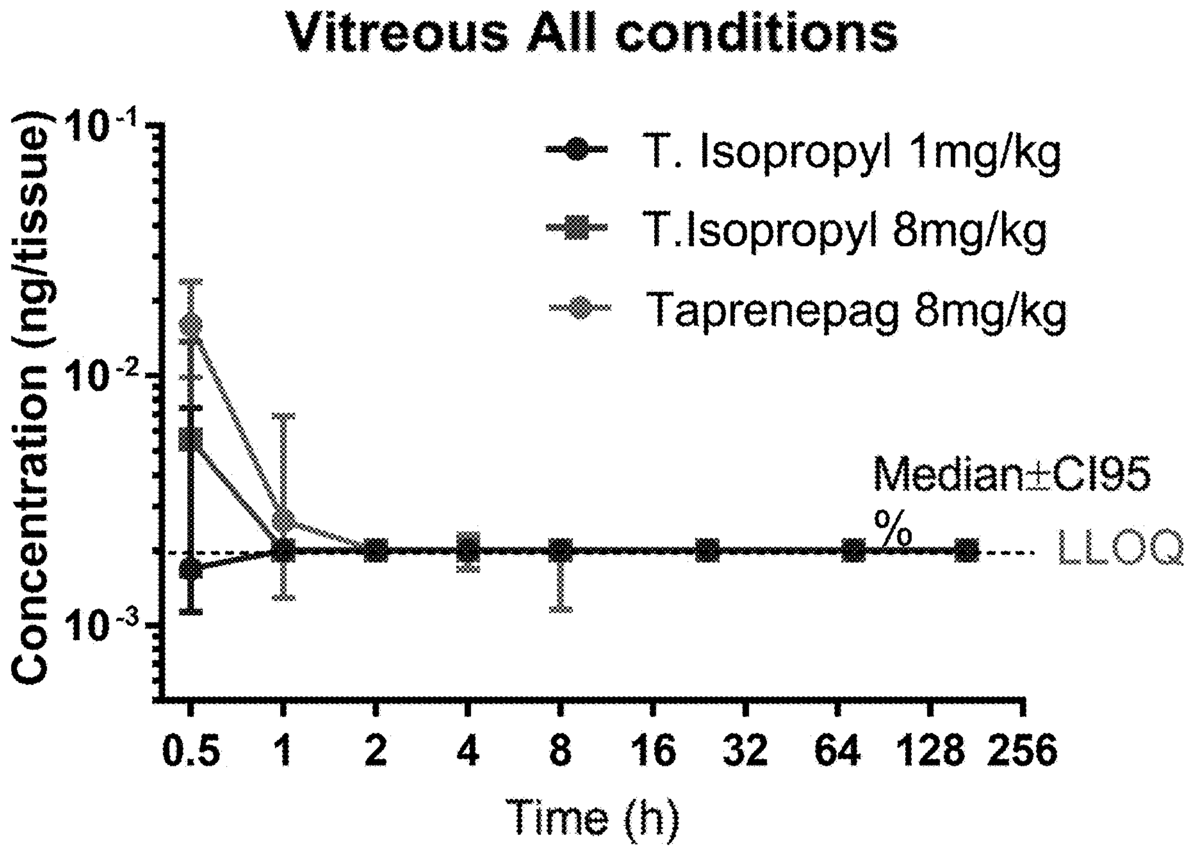

To examine the stability of taprenepag isopropyl (PF 04217329, the prodrug of CP-544326) and taprenepag (CP-544326) in vivo, a pharmacokinetics (PK) study was performed in wild type C57BL/6J mice. FIG. 36 shows the PK study design. After intraperitoneal injections of taprenepag isopropyl (1 mg/kg or 8 mg/kg) or taprenepag (8 mg/kg), the concentrations of these compounds in various organs were determined at different time points. The results show, in general, taprenepag is more stable than taprenepag isopropyl in plasma (FIG. 37A), kidney (FIG. 37B), testis (FIG. 37C), retina (FIG. 37D), and vitreous humor (FIG. 37E).

Homozygous deletion of NPHP1 is the most common cause of juvenile nephronophthisis 1. Homozygous or compound heterozygous mutations in NPHP1 are also associated with, for example, Joubert syndrome 4 (brain abnormalities) and Senior-Løken syndrome 1 (retinopathy). NPHP1 KO animals were generated to test whether taprenepag can be used to treat these diseases. To establish a CRISPR/Cas9-engineered $Nphp1^{-/-}$ mouse model, single guide RNAs were injected in C57BL/6J embryos, and generated a 76 bp deletion encompassing the ATG in exon 1 of Nphp1. To characterize the natural history of $Nphp1^{-/-}$ mouse model, histochemical staining of kidney and retina sections was performed from $Nphp1^{+/+}$ and $Nphp1^{-/-}$ mice. $Nphp1^{-/-}$ mouse model does not exhibit a renal phenotype. In contrast, P14-aged $Nphp1^{-/-}$ mice start to exhibit decreasing thickness of photoreceptors layers (e.g., inner segment (IS), outer segment (OS) and outer nuclear layer (ONL)), until they were sacrificed at P28, indicating a rapid retinal degeneration in this model corresponding to a ciliopathy-related manifestation.

Figure 38A:
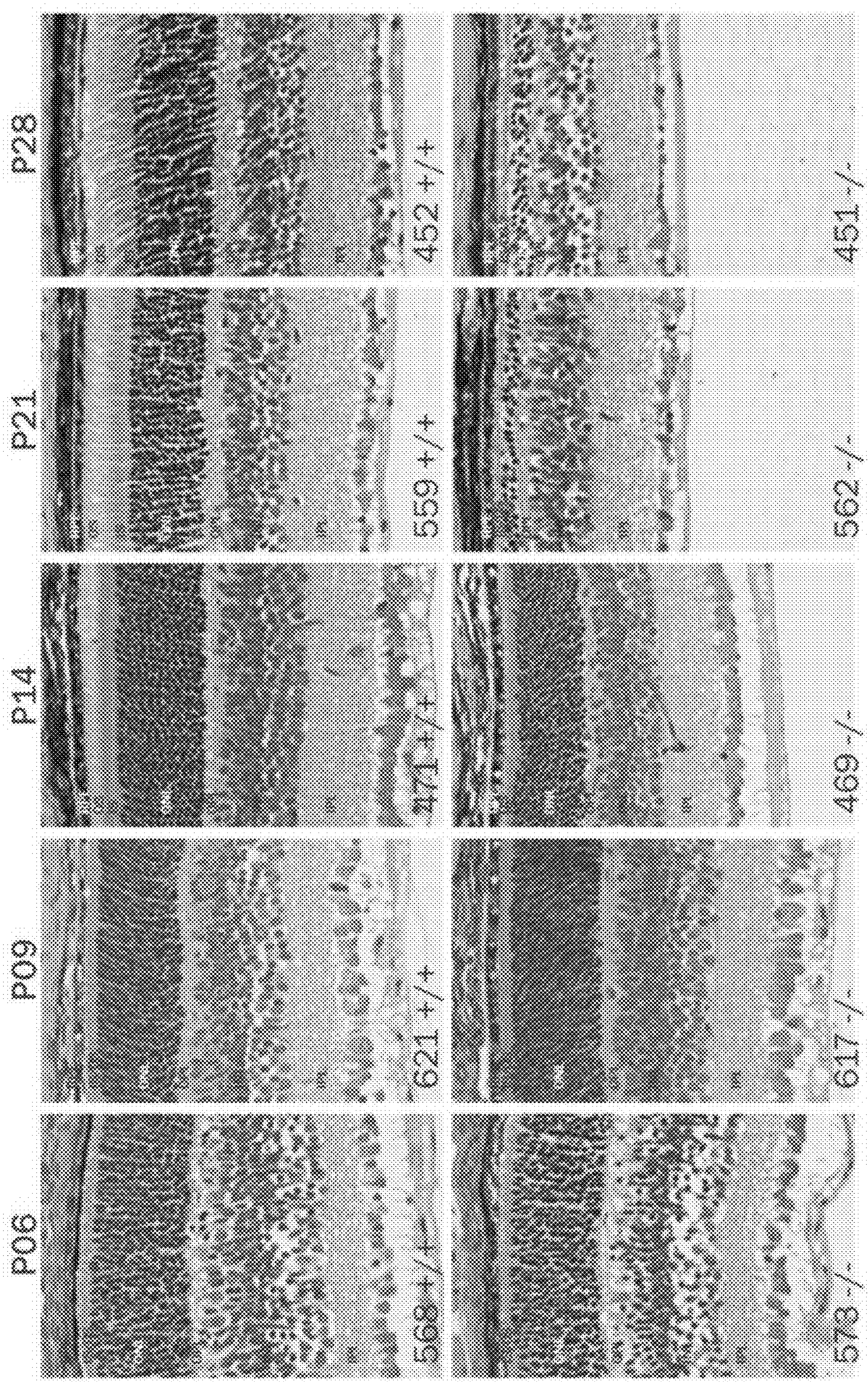
FIG. 38A shows periodic acid-Schiff staining of retina, in wt and Nphp1$^{-/-}$ mice.
Figure 38B:
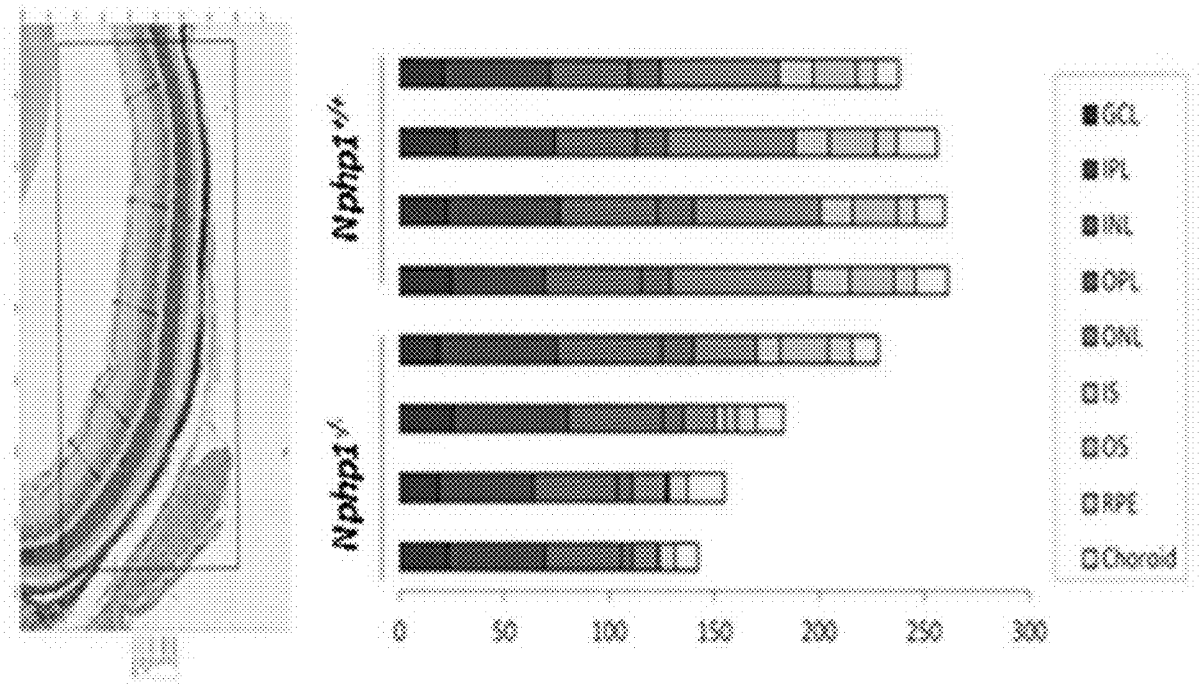
FIG. 38B shows semi-automated quantification method of retina layers thickness.
Figure 38C:
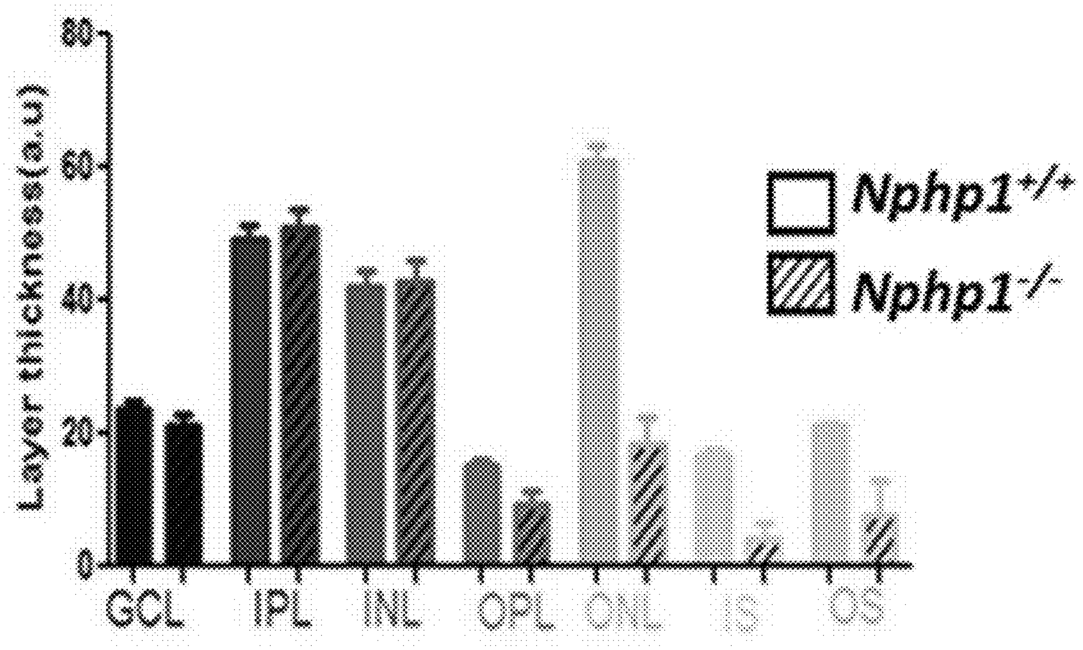
FIG. 38C shows the quantification of the retina layers thickness in Nphp1$^{-/-}$ mice, as compared with the wt mice.

To evaluate the retinal degeneration, a semi-automated tool was developed to provide detection and quantitative thickness measurements of each retinal layers at five distant plans manually marked on the retinal section (FIG. 38B). Semi-automated quantification analysis confirms a clear decrease in thickness of photoreceptors layers ONL, IS and OS (FIG. 38C).

Figure 39A:
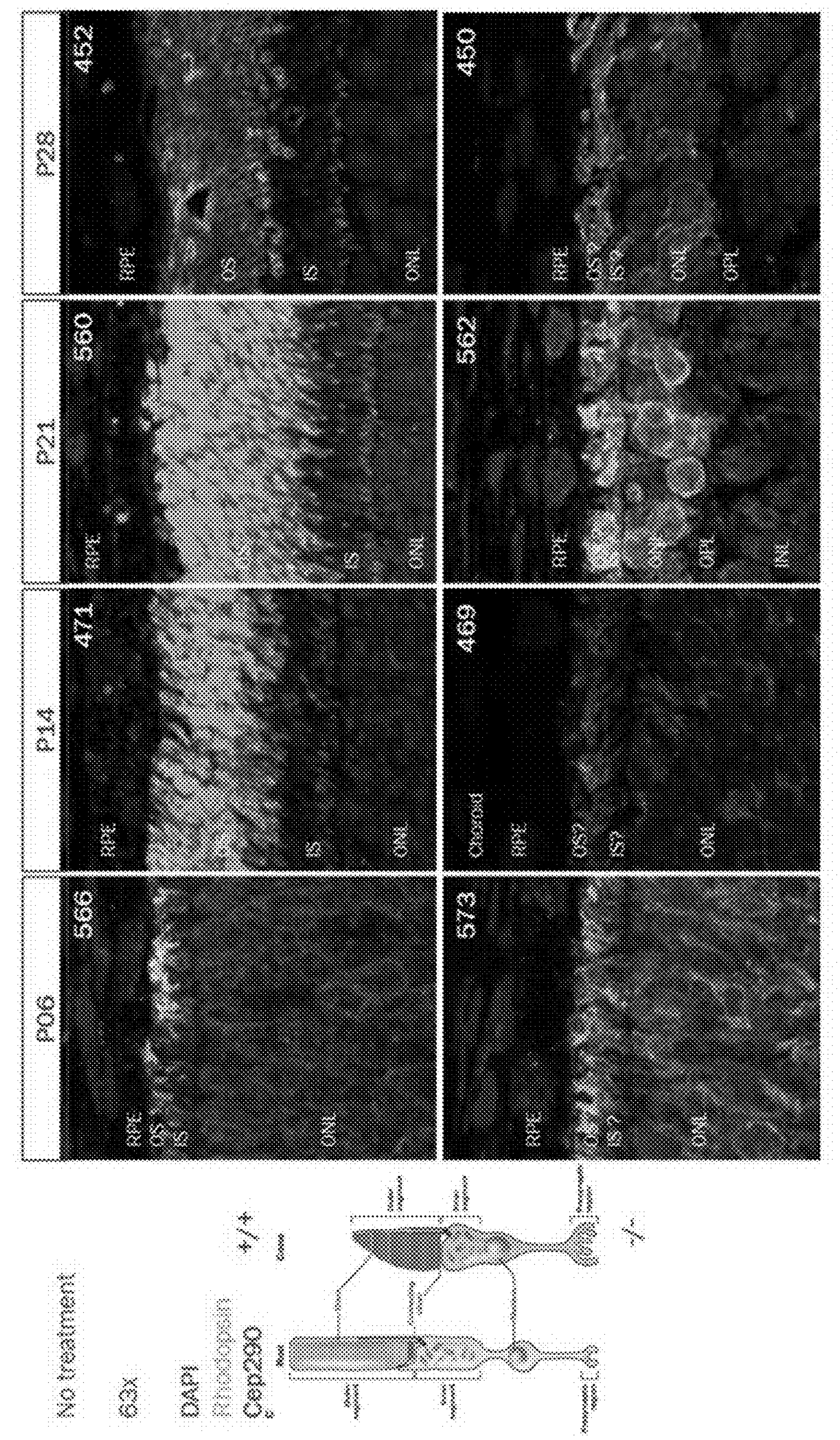
FIGS. 39A and B show immunohistostaining in wt and Nphp1$^{-/-}$ mice retina of Cep290 as ciliary marker and rhodopsin and PNA (peanut agglutinin lectin) as photoreceptor markers of outer segment (OS), and inner/outer segments, respectively.
Figure 39B:
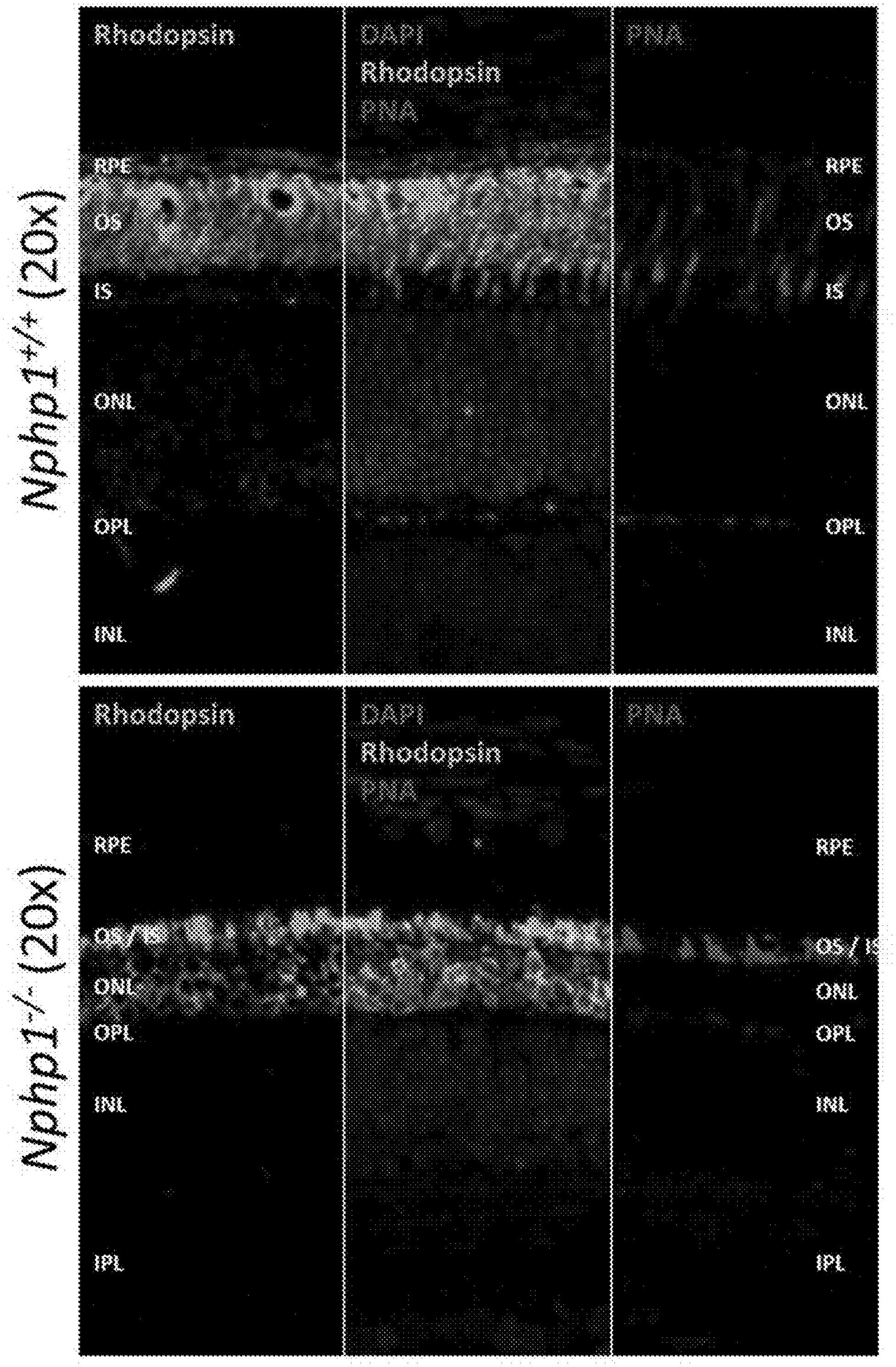

To assess the effect of Nphp1 deletion on the structural organization of photoreceptors in this model, immunohistochemistry (IH) analysis was performed on retina sections from $Nphp1^{+/+}$ and $Nphp1^{-/-}$ mice (FIGS. 39A and B). Tissues were fixed and fluorescence-labeled with DAPI (for nuclei staining), anti-rhodopsin antibody (for OS staining), and anti-Cep290 antibody (for connecting cilia staining) or PNA (for OS and IS staining), detected using immunofluorescence microscopy. FIG. 39A shows that $Nphp1^{-/-}$ mouse model exhibits a well-organized photoreceptor structure, with localization of rhodopsin along the OS, bounded by Cep290 punctiform distribution at the connecting cilia. This indicates that the connecting cilium is functional to allow the rhodopsin transport from the IS to the photosensitive OS. In contrast, $Nphp1^{-/-}$ mice fail to form connecting cilia, and exhibit a clear rhodopsin mislocalization in IS and OS, suggesting that the transport of rhodopsin requires the correct formation/maintenance of connecting cilium. Concordantly, FIG. 39B shows that $Nphp1^{-/-}$ mice exhibit a clear rhodopsin mislocalization in IS/OS, and ONL as well, in contrast with $Nphp1^{+/+}$ mice.

Figure 40:
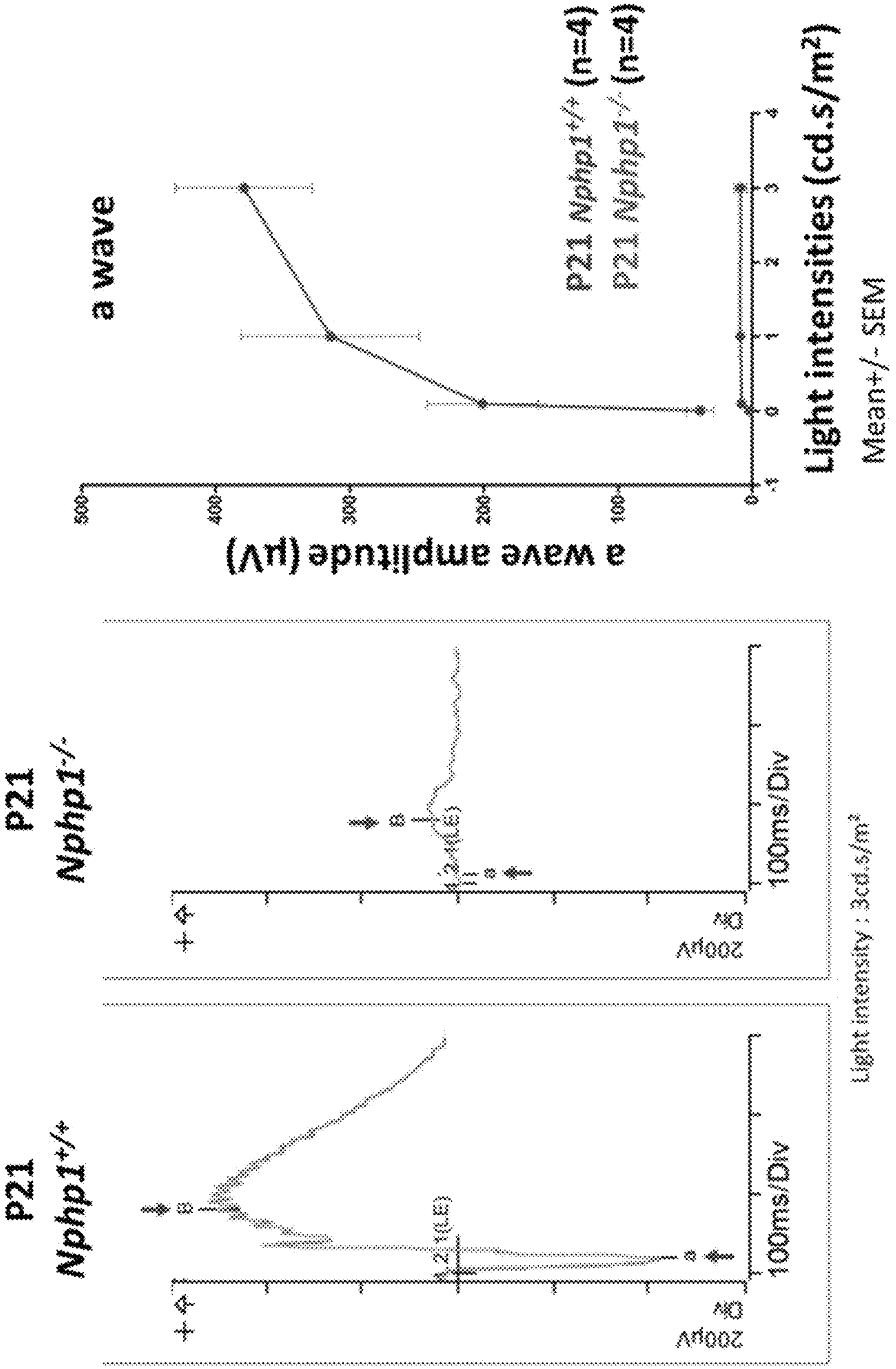
FIG. 40 shows electroretinogram of Nphp1$^{-/-}$ mice, as compared with the wt mice.
Figure 41:
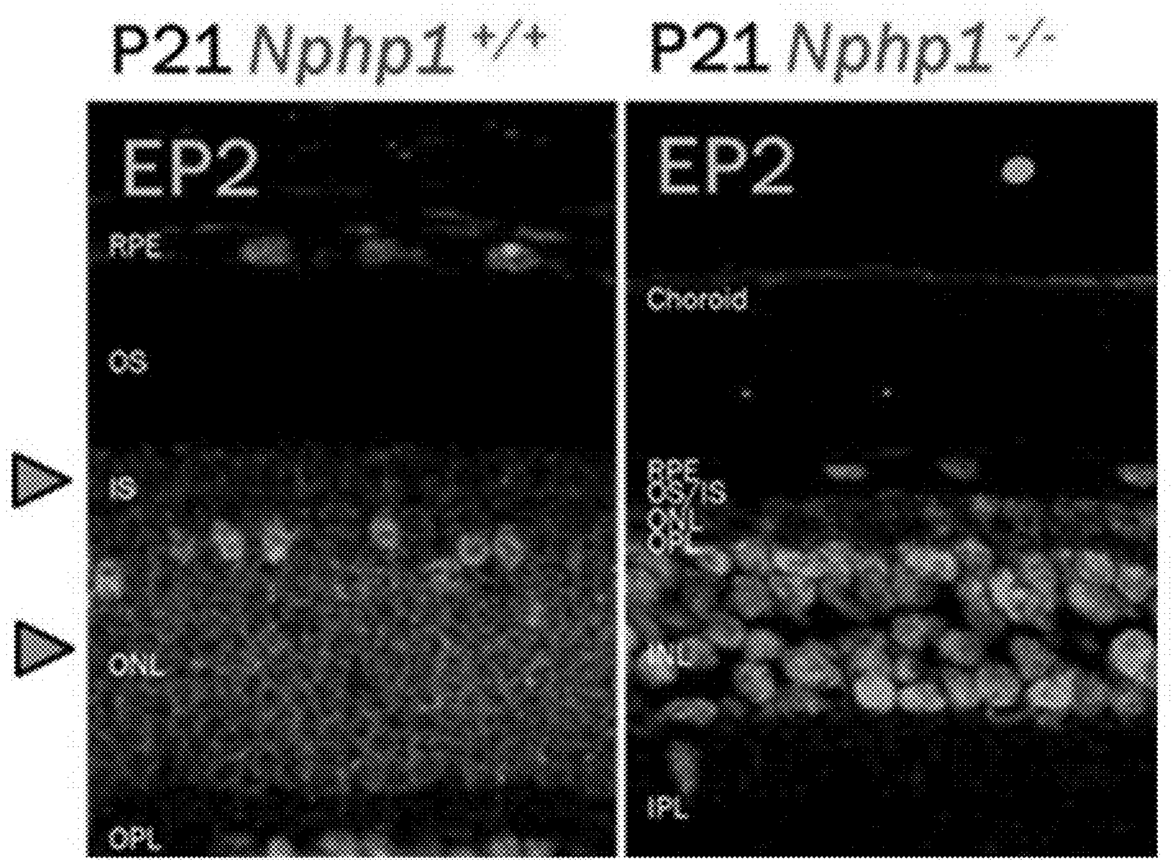
FIG. 41 shows expression of EP2 receptor in wt and Nphp1$^{-/-}$ mice.

To assess the effect of Nphp1 deletion on the functionality of photoreceptors, electroretinogram (ERG) was performed on $Nphp1^{+/+}$ and $Nphp1^{-/-}$ mice, under light stimuli of different intensities (FIGS. 40A-C). FIGS. 40A and B show ERG a- and b-waves recorded from the same animals at P21, for a given light intensity. In contrast with $Nphp1^{+/+}$ mice, $Nphp1^{-/-}$ mice display drastically lower ERG amplitudes at a given intensity of light stimulus. FIG. 40C is a magnification of ERG a-waves under light stimuli of different intensities, as a-waves reflect photoreceptor function.

Before testing the effect of CP-544326 on ciliopathy-related phenotypes, expression of the potential target EP2 was studied by immunohistochemistry. Fluorescence microscopy reveals that EP2 is well expressed at protein level in photoreceptors layers IS and ONL of P21-aged $Nphp1^{+/+}$ and $Nphp1^{-/-}$ mice, although OS/IS/ONL boundaries were difficult to discriminate in $Nphp1^{-/-}$ mice.

Figure 42:
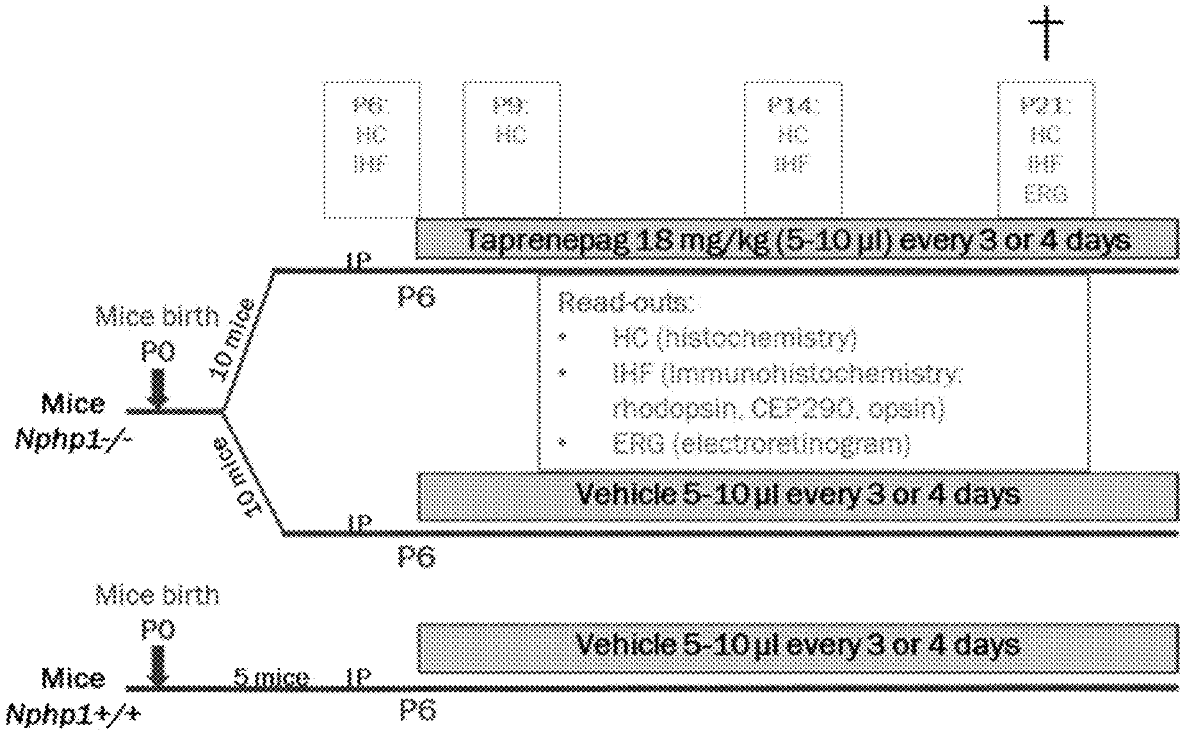
FIG. 42 shows a study design in accordance with one embodiment of the present disclosure.

FIG. 42 shows the experimental design to assess the effect of CP-544326 on the retinal degeneration occurring in the $Nphp1^{-/-}$ mouse model. Briefly, animals were injected (i.p.) either with vehicle or CP-544326 in vehicle (18 mg/kg), every 3 or 4 days, from P6 until P21. Phenotypic read-outs encompass structural and functional parameters described as previously for the characterization of $Nphp1^{-/-}$ mouse model.

Figure 43:
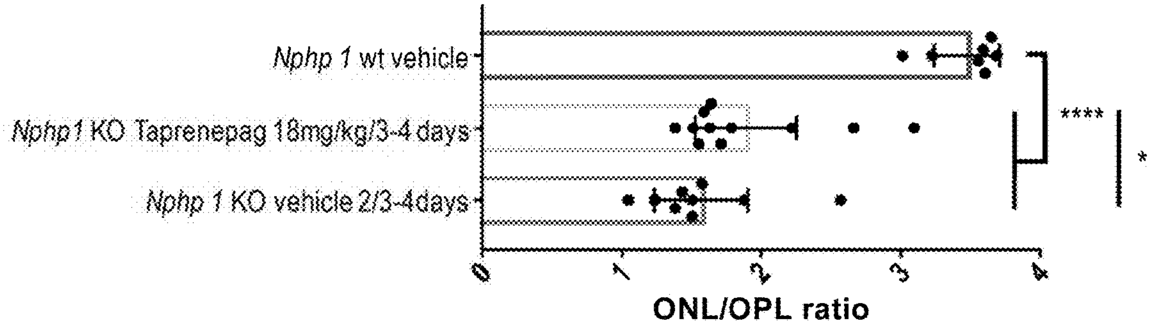
FIG. 43 shows the effect of CP-544326 on ONL/OPL retina layers thicknesses ratio, in Nphp1$^{-/-}$ mice.
Figure 44:
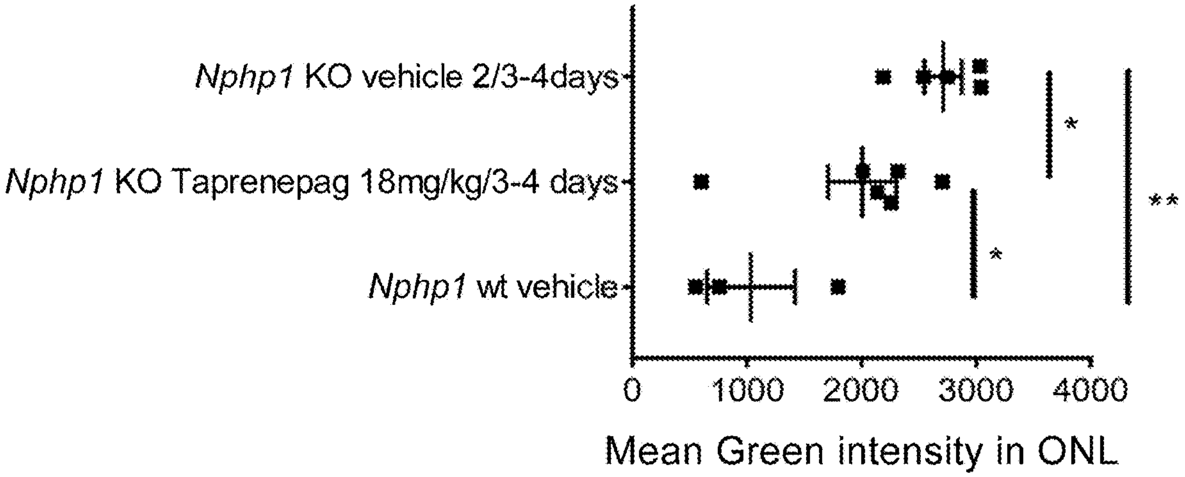
FIG. 44 shows the effect of CP-544326 on green-labeled rhodopsin mislocalization in ONL, in Nphp1$^{-/-}$ mice.

FIG. 43 shows the effect of CP-544326 on the photoreceptor layer ONL thickness represented by ONL/OPL ratio, calculated from the semi-automated quantification of retina layers on IHC sections. CP-544326 treatment (18 mg/kg) significantly prevents the decrease of ONL/OPL ratio in $Nphp1^{-/-}$ mice, as compared with that of vehicle treatment ($p<0.05$, Mann-Whitney test). Similarly, CP-544326 treatment (18 mg/kg) significantly prevented rhodopsin mislocalization in $Nphp1^{-/-}$ mice, represented as the parameter "Mean Green intensity in ONL" quantified in a semi-automatic manner" on IHC sections by fluorescence microscopy ($p<0.05$, unpaired t-test) (FIG. 44).

Figure 45:
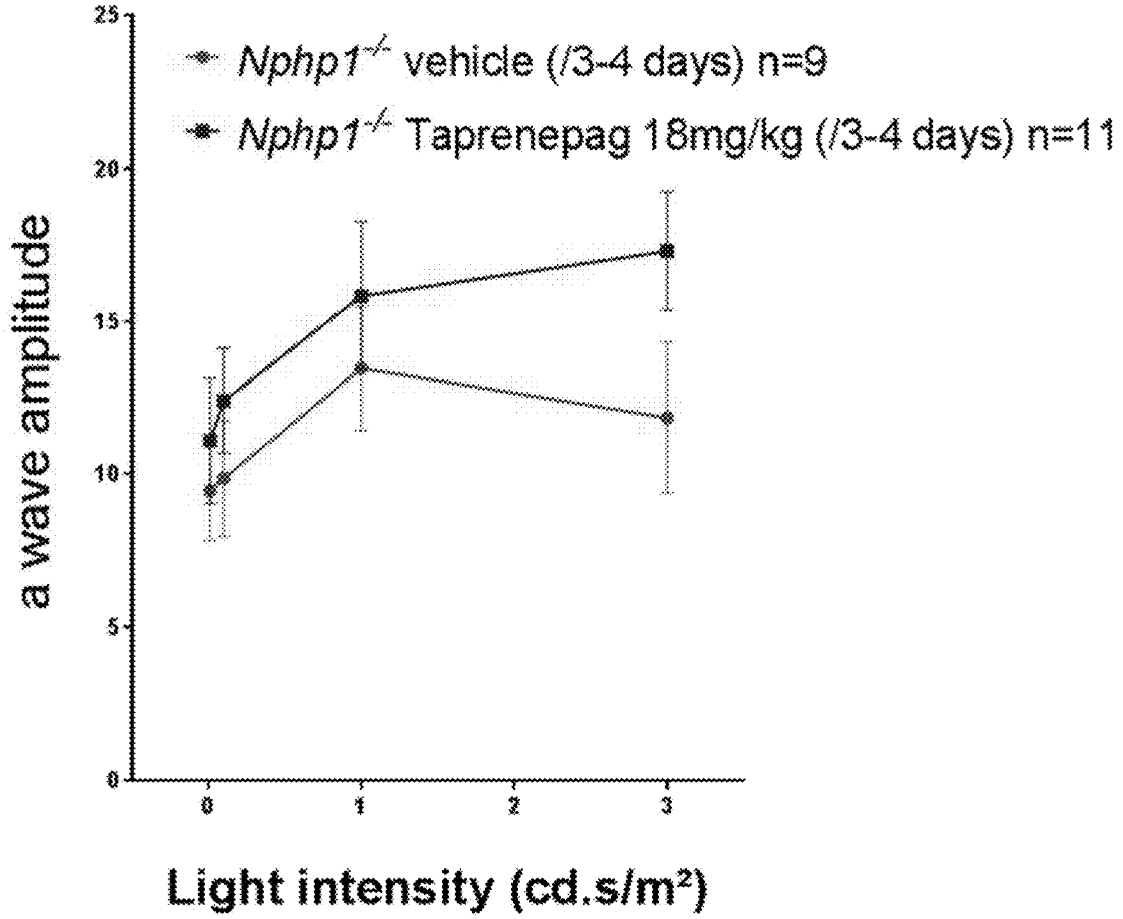
FIG. 45 shows the effect of CP-544326 on electroretinogram of Nphp1$^{-/-}$ mice.

To assess the effect of CP-544326 on the photoreceptors responsiveness, electroretinogram (ERG) was performed on $Nphp1^{+/+}$ and $Nphp1^{-/-}$ mice, treated with CP-544326 (18 mg/kg) or vehicle, under light stimuli of different intensities. The magnification of ERG a-waves (FIG. 45) shows that CP-544326 (18 mg/kg) triggers a slight improvement in the amplitude of photoreceptor response, as compared with that of vehicle-treated $Nphp1^{-/-}$ mice.

All references cited in this specification are herein incorporated by reference as though each reference was specifically and individually indicated to be incorporated by reference. It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A method of treating nephronophthisis (NPHP) in a subject having NPHP, the method comprising:

administering to the subject, prior to the development of end-stage renal disease (ESRD), a therapeutically effective amount of at least one non-prostanoid agonist that selectively targets E-type prostaglandin receptor 2 (EP2) and is capable of restoring ciliogenesis.

2. The method of claim 1, wherein the NPHP results from a homozygous deletion of the NPHP1 locus.

3. The method of claim 1, wherein the NPHP results from a heterozygous deletion of the NPHP1 locus and a heterozygous or homozygous loss of function at a second locus.

4. The method of claim 1, wherein the NPHP results from a heterozygous deletion in one allele of NPHP1 and a loss of function mutation in the second allele.

5. The method of claim 1, wherein the NPHP results from a loss of function mutation in one allele of NPHP1 and different loss of function mutation in the second allele.

6. The method of claim 1, wherein the at least one non-prostanoid agonist is selected from the group consisting of: CP-544326 (taprenepag), PF 04217329 (taprenepag isopropyl), AGN-210669 (simenepag isopropyl), AGN-210961 (aganepag isopropyl), DE-117 (omidenepag isopropyl), CP-533536 (evatanepag), and any combination thereof.

7. The method of claim 1, wherein the NPHP results from one or more NPHP1, NPHP4, NPHP6/CEP290 alleles and other pathogenic or loss of function variants.

8. The method of claim 1, wherein the non-prostanoid agonist comprises CP-544326 (taprenepag), or a prodrug thereof, or both.

9. The method of claim 1, wherein the effective amount is between 100 pM and 5 pM.

10. The method of claim 1, wherein the non-prostanoid agonist comprises PF 04217329 (taprenepag isopropyl).

11. The method of claim 1, wherein the non-prostanoid agonist comprises CP-544326 (taprenepag), or PF 04217329 (taprenepag isopropyl), or both.

12. The method of claim 1, wherein the non-prostanoid agonist comprises a pyridyl sulfonamide derivative.

13. The method of claim 12, wherein the pyridyl sulfonamide derivative comprises CP-544326 (taprenepag), PF 04217329 (taprenepag isopropyl), DE-117 (omidenepag isopropyl), or CP-533536 (evatanepag), or any combination thereof.

14. The method of claim 1, wherein the non-prostanoid agonist comprises a N-phenyl-y-lactam derivative.

15. The method of claim 14, wherein the N-phenyl-y-lactam derivative comprises AGN-210669 (simenepag isopropyl), or AGN-210961 (aganepag isopropyl), or both.

16. The method of claim 1, wherein the method further comprises administering to the subject a therapeutically effective amount of at least one prostanoid agonist.

17. The method of claim 16, wherein the prostanoid agonist comprises prostaglandin E1 (PGE1), prostaglandin E2 (PGE2), or 16,16-dimethyl-PGE2 (dmPGE2), or any combination thereof.

18. The method of claim 1, wherein NPHP results from a NPHP6/CEP290 allele.

* * * * *